(12) United States Patent
Schenk

(10) Patent No.: US 6,962,707 B2
(45) Date of Patent: *Nov. 8, 2005

(54) PREVENTION AND TREATMENT OF AMYLOIDOGENIC DISEASE

(75) Inventor: Dale B. Schenk, Burlingame, CA (US)

(73) Assignee: Neuralab Limited (BM)

(*) Notice: Subject to any disclaimer, the term of this patent is extended or adjusted under 35 U.S.C. 154(b) by 73 days.

This patent is subject to a terminal disclaimer.

(21) Appl. No.: 10/884,892

(22) Filed: Jul. 1, 2004

(65) Prior Publication Data

US 2005/0053614 A1 Mar. 10, 2005

Related U.S. Application Data

(63) Continuation of application No. 09/201,430, filed on Nov. 30, 1998, now Pat. No. 6,787,523.
(60) Provisional application No. 60/080,970, filed on Apr. 7, 1998, and provisional application No. 60/067,740, filed on Dec. 2, 1997.

(51) Int. Cl.[7] .............................................. A61K 39/385
(52) U.S. Cl. ..................... 424/193.1; 424/185.1; 424/1.57; 424/9.1; 424/9.2; 514/2; 514/21; 436/86; 530/300; 530/403; 530/350
(58) Field of Search ..................... 424/193.1, 185.1, 424/1.57, 9.1, 9.2; 514/2, 21; 436/86; 530/300, 403, 350

(56) References Cited

U.S. PATENT DOCUMENTS

| | | | |
|---|---|---|---|
| 4,666,829 A | 5/1987 | Glenner et al. |
| 4,713,366 A | 12/1987 | Stevens |
| 5,004,697 A | 4/1991 | Pardridge |
| 5,057,540 A | 10/1991 | Kensil et al. |
| 5,187,153 A | 2/1993 | Cordell et al. |
| 5,192,753 A | 3/1993 | McGeer et al. |
| 5,208,036 A | 5/1993 | Eppstein et al. |
| 5,220,013 A | 6/1993 | Ponte et al. |
| 5,231,000 A | 7/1993 | Majocha et al. |
| 5,231,170 A | 7/1993 | Averback |
| 5,270,165 A | 12/1993 | Van Nostrand et al. |
| 5,387,742 A | 2/1995 | Cordell |
| 5,434,170 A | 7/1995 | Andrulis, Jr. |
| 5,441,870 A | 8/1995 | Seubert et al. |
| 5,464,823 A | 11/1995 | Lehrer et al. |
| 5,571,499 A | 11/1996 | Hafler et al. |
| 5,571,500 A | 11/1996 | Hafler et al. |
| 5,583,112 A | 12/1996 | Kensil et al. |
| 5,585,100 A | 12/1996 | Mond et al. |
| 5,593,846 A | 1/1997 | Schenk et al. |
| 5,605,811 A | 2/1997 | Seubert et al. |
| 5,612,486 A | 3/1997 | McConlogue et al. |
| 5,622,701 A | 4/1997 | Berg |
| 5,641,473 A | 6/1997 | Hafler et al. |
| 5,641,474 A | 6/1997 | Hafler et al. |
| 5,645,820 A | 7/1997 | Hafler et al. |
| 5,679,348 A | 10/1997 | Nesburn et al. |
| 5,688,651 A | 11/1997 | Solomon |
| 5,721,130 A | 2/1998 | Seubert et al. |
| 5,733,547 A | 3/1998 | Weiner et al. |
| 5,736,142 A | 4/1998 | Sette et al. |
| 5,744,368 A | 4/1998 | Goldgaber et al. |
| 5,750,349 A | 5/1998 | Suzuki et al. |
| 5,750,361 A | 5/1998 | Prusiner et al. |
| 5,753,624 A | 5/1998 | McMichael et al. |
| 5,776,468 A | 7/1998 | Hauser et al. |
| 5,780,587 A | 7/1998 | Potter |
| 5,786,180 A | 7/1998 | Konig et al. |
| 5,817,626 A | 10/1998 | Findeis et al. |
| 5,824,322 A | 10/1998 | Balasubramanian |
| 5,837,473 A | 11/1998 | Maggio et al. |
| 5,837,672 A | 11/1998 | Schenk et al. |
| 5,846,533 A | 12/1998 | Prusiner et al. |
| 5,849,298 A | 12/1998 | Weiner et al. |
| 5,851,996 A | 12/1998 | Kline |
| 5,854,204 A | 12/1998 | Findeis et al. |
| 5,854,215 A | 12/1998 | Findeis et al. |
| 5,869,054 A | 2/1999 | Weiner et al. |
| 5,869,093 A | 2/1999 | Weiner et al. |
| 5,877,399 A | 3/1999 | Hsiao et al. |
| 5,935,927 A | 8/1999 | Vitek et al. |
| 5,955,079 A | 9/1999 | Mond et al. |
| 5,955,317 A | 9/1999 | Suzuki et al. |
| 5,958,883 A | 9/1999 | Snow |
| 5,985,242 A | 11/1999 | Findeis et al. |

(Continued)

FOREIGN PATENT DOCUMENTS

| | | |
|---|---|---|
| EP | 451 700 A1 | 10/1991 |
| EP | 276 723 B1 | 12/1993 |
| EP | 613 007 A2 | 8/1994 |
| EP | 666 080 A1 | 8/1995 |
| EP | 359 783 B1 | 11/1995 |
| EP | 683 234 A1 | 11/1995 |

(Continued)

OTHER PUBLICATIONS

U.S. Appl. No. 60/254,465, Holtzman et al., filed Dec. 8, 2000.

U.S. Appl. No. 60/254,498, Holtzman et al., filed Dec. 8, 2000.

U.S. Appl. No. 09/724,842, filed Nov. 28, 2000, Chalifour et al.

(Continued)

Primary Examiner—Laurie Scheiner
(74) Attorney, Agent, or Firm—Townsend and Townsend and Crew LLP

(57) ABSTRACT

The invention provides compositions and methods for treatment of amyloidogenic diseases. Such methods entail administering an agent that induces a beneficial immune response against an amyloid deposit in the patient. The methods are particularly useful for prophylactic and therapeutic treatment of Alzheimer's disease. In such methods, a suitable agent is Aβ peptide or an antibody thereto.

42 Claims, 13 Drawing Sheets

U.S. PATENT DOCUMENTS

| | | |
|---|---|---|
| 5,989,566 A | 11/1999 | Cobb et al. |
| 6,057,367 A | 5/2000 | Stamler et al. |
| 6,114,133 A | 9/2000 | Seubert et al. |
| 6,150,091 A | 11/2000 | Pandolfo et al. |
| 6,262,335 B1 | 7/2001 | Hsiao et al. |
| 6,284,221 B1 | 9/2001 | Schenk et al. |
| 6,284,533 B1 | 9/2001 | Thomas |
| 6,294,171 B2 | 9/2001 | McMichael |
| 6,303,567 B1 | 10/2001 | Findeis et al. |
| 6,399,314 B1 | 6/2002 | Krishnamurthy |
| 6,417,178 B1 | 7/2002 | Klunk et al. |
| 6,562,341 B2 | 5/2003 | Prusiner et al. |
| 6,713,450 B2 | 3/2004 | Frangione et al. |
| 2002/0077288 A1 | 6/2001 | Frangione |
| 2001/0018053 A1 | 8/2001 | McMichael |
| 2001/0021769 A1 | 9/2001 | Prusiner |
| 2002/0009445 A1 | 1/2002 | Du et al. |
| 2002/0086847 A1 | 7/2002 | Chain |
| 2002/0094335 A1 | 7/2002 | Chalifour et al. |
| 2001/0102261 | 8/2002 | Raso |
| 2002/0132268 A1 | 9/2002 | Chang et al. |
| 2002/0133001 A1 | 9/2002 | Gefter et al. |
| 2002/0136718 A1 | 9/2002 | Raso |
| 2002/0160394 A1 | 10/2002 | Wu |
| 2002/0162129 A1 | 10/2002 | Lannfelt |
| 2002/0168377 A1 | 11/2002 | Schaetzl |
| 2002/0187157 A1 | 12/2002 | Jensen et al. |
| 2003/0068316 A1 | 4/2003 | Klein et al. |
| 2003/0068325 A1 | 4/2003 | Wang |
| 2003/0073655 A1 | 4/2003 | Chain |
| 2003/0165496 A1 | 9/2003 | Basi et al. |
| 2003/0166558 A1 | 9/2003 | Frangione et al. |
| 2002/0197258 A1 | 12/2003 | Ghanbari et al. |
| 2004/0043418 A1 | 3/2004 | Holtzman et al. |

FOREIGN PATENT DOCUMENTS

| | | | |
|---|---|---|---|
| EP | | 440 619 B1 | 1/1996 |
| EP | | 526 511 B1 | 5/1997 |
| EP | | 782 859 A1 | 7/1997 |
| EP | | 783 104 A1 | 7/1997 |
| EP | | 594 607 B1 | 8/1997 |
| EP | | 845 270 A1 | 6/1998 |
| EP | | 863 211 A1 | 9/1998 |
| EP | | 868 918 A2 | 10/1998 |
| EP | | 652 962 B1 | 12/1998 |
| EP | | 911 036 A2 | 4/1999 |
| EP | | 561 087 B1 | 8/1999 |
| EP | | 639 081 B1 | 11/1999 |
| EP | | 506 785 B1 | 3/2000 |
| EP | | 1 172 378 A1 | 1/2002 |
| GB | | 2 220 211 A | 1/1990 |
| GB | | 2 335 192 A | 9/1999 |
| WO | WO 88/10120 A1 | | 12/1988 |
| WO | WO 89/01343 A1 | | 2/1989 |
| WO | WO 89/03687 A1 | | 5/1989 |
| WO | WO 89/06242 A1 | | 7/1989 |
| WO | WO 89/06689 A1 | | 7/1989 |
| WO | WO 90/12870 A1 | | 11/1990 |
| WO | WO 90/12871 A1 | | 11/1990 |
| WO | WO 91/08760 A1 | | 6/1991 |
| WO | WO 91/12816 A1 | | 9/1991 |
| WO | WO 91/16819 A1 | | 11/1991 |
| WO | WO 91/19810 A1 | | 12/1991 |
| WO | WO 92/06187 A1 | | 4/1992 |
| WO | WO 92/06708 A1 | | 4/1992 |
| WO | WO 92/13069 A1 | | 8/1992 |
| WO | WO 93/02189 A1 | | 2/1993 |
| WO | WO 93/04194 A1 | | 3/1993 |
| WO | WO 93/14200 A1 | | 7/1993 |
| WO | WO 93/15760 A1 | | 8/1993 |
| WO | WO 93/16724 A1 | | 9/1993 |
| WO | WO 93/21950 A1 | | 11/1993 |
| WO | WO 94/01772 A1 | | 1/1994 |
| WO | WO 94/03615 A1 | | 2/1994 |
| WO | WO 94/28412 A1 | | 12/1994 |
| WO | WO 95/04151 A2 | | 2/1995 |
| WO | WO 95/05853 A1 | | 3/1995 |
| WO | WO 95/11008 A2 | | 4/1995 |
| WO | WO 95/11311 A1 | | 4/1995 |
| WO | WO 95/11994 A1 | | 5/1995 |
| WO | WO 95/12815 A1 | | 5/1995 |
| WO | WO 95/31996 A1 | | 11/1995 |
| WO | WO 96/18900 A1 | | 6/1996 |
| WO | WO 96/25435 A1 | | 8/1996 |
| WO | WO 96/28471 A1 | | 9/1996 |
| WO | WO 96/39176 A1 | | 12/1996 |
| WO | WO 97/10505 A1 | | 3/1997 |
| WO | WO 97/17613 A1 | | 5/1997 |
| WO | WO 97/21728 A1 | | 6/1997 |
| WO | WO 98/07850 A2 | | 2/1998 |
| WO | WO 98/44955 A1 | | 10/1998 |
| WO | WO 99/00150 A2 | | 1/1999 |
| WO | WO 99/06066 A2 | | 2/1999 |
| WO | WO 99/27911 A1 | | 6/1999 |
| WO | WO 99/27944 A1 | | 6/1999 |
| WO | WO 99/27949 A1 | | 6/1999 |
| WO | WO 99/06545 A2 | | 11/1999 |
| WO | WO 99/58564 A1 | | 11/1999 |
| WO | WO 99/60021 A2 | | 11/1999 |
| WO | WO 99/60024 A1 | | 11/1999 |
| WO | WO 01/62284 A2 | | 3/2000 |
| WO | WO 00/43039 A1 | | 7/2000 |
| WO | WO 00/43049 A1 | | 7/2000 |
| WO | WO 00/72870 A1 | | 12/2000 |
| WO | WO 00/72876 A2 | | 12/2000 |
| WO | WO 00/72876 A3 | | 12/2000 |
| WO | WO 00/72880 A3 | | 12/2000 |
| WO | WO 00/72880 A2 | | 12/2000 |
| WO | WO 00/77178 A1 | | 12/2000 |
| WO | WO 02/03911 A2 | | 4/2001 |
| WO | WO 01/39796 A2 | | 6/2001 |
| WO | WO 01/42306 A2 | | 6/2001 |
| WO | WO 01/62801 A2 | | 8/2001 |
| WO | WO 01/77167 A2 | | 10/2001 |
| WO | WO 01/90182 A2 | | 11/2001 |
| WO | WO 02/34777 A1 | | 5/2002 |
| WO | WO 02/34878 A2 | | 5/2002 |
| WO | WO 03/020212 A2 | | 3/2003 |
| WO | WO 03/074081 A1 | | 9/2003 |
| WO | WO 03/104437 A2 | | 12/2003 |

OTHER PUBLICATIONS

U.S. Appl. No. 60/184,601, Holtzman et al., filed Feb. 24, 2000.

U.S. Appl. No. 60/169,687, Chain, filed Dec. 8, 1999.

U.S. Appl. No. 60/168,594, Chalifour et al., filed Nov. 29, 1999.

U.S. Appl. No. 09/441,140, filed Nov. 16, 1999, Solomon et al.

U.S. Appl. No. 60/186,295, Rasmussen et al., filed Mar. 1, 2000.

Aguzzi et al., "Prion research: the next frontiers," *Nature*, 389:795–798 (1997).

Akiyama et al., "Inflammation and Alzheimer's disease," *Neurobiology of Aging*, 21:383–421 (2000).

Akiyama et al., "Occurrence of the Diffuse Amyloid β–Protein (Aβ) Deposits With Numerous Aβ–Containing Gilal Cells in the Cerebral Cortex of Patients With Alzheimer's Disease," *Gila*, 25:324–331 (1999).

Andersen et al., "Do nonsteroidal anti–inflammatory drugs decrease the risk for Alzheimer's disease?", *Neurology*, 45:1441–1445 (1995).

Associated Press, "Immune cells may promote Alzehimer's, a study finds," *The Boston Globe* (Apr. 13, 1995).

Bard et al., "Peripherally administered antibodies against amyloid β–peptide enter the central nervous system and reduce pathology in a mouse model of Alzheimer disease," *Nature Medicine*, 6(8):916–919 (2000).

Barrow et al., "Solution Conformations and aggregational Properties of Synthetic Amyloid Beta–Peptides of Alzheimer's Disease. Analysis of Circular Dichroism Spectra," *J. Mol. Biol.*, 225(4): 1075–1093 (1992).

Bauer et al., "Interleukin–6 and α–2–macroglobulin indicate an acute–phase state in Alzheimer's disease cortices," *FEBS Letters*, 285(1):111–114 (1991).

Beasley, "Alzheimer's traced to proteins caused by aging," Reuters, Apr. 20, 2001 7:56 PM ET.

Benjamini and Leskowitz, from *IMMUNOLOGY A Short Course*, Second Edition, Chapter 4, Antibody Structure, pp. 49–65, 1991, published by Wiley–Liss, Inc., New York, New York.

Bercovici et al., "Chronic Intravenous Injections of Antigen Induce and Maintain Tolerance in T Cell Receptor–Transgenic Mice," *Eur. J. Immunol.*, 29:345–354 (1999).

Bickel et al., "Site Protected, Cationized Monoclonal Antibody Against Beta Amyloid as a Potential Diagnostic Imaging Technique for Alzheimer's Diseases," *Soc. for Neuroscience Abstracts*. 18:764 (1992).

Blass, "Immunologic Treatment of Alzheimer's Disease," *New England J. Medicine*, 341(22):1694 1999.

Bodmer et al., "Transforming Growth Factor–Beta Bound to Soluble Derivatives of the Beta Amyloid Precursor Protein of Alzheimer's Disease," *Biochem. Biophys. Res. Comm.*, 171(2):890–897 (1990).

Borchelt et al., "Accelerated Amyloid Deposition in the Brains of Transgenic Mice Coexpressing Mutant Presenilin 1 and Amyloid Precursor Proteins," *Neuron*, 19: 939–945 (1997).

Bork, P., "Powers and Pitfalls in Sequence Analysis: The 70% Hurdle," *Genome Research*, 10:398–400 (2000).

Bork et al., "Go hunting in sequence databases but watch out for the traps," *Trends in Genetics*, 12(10):425–427 (1996).

Boris–Lawrie et al., "Recent advances in retrovirus vector technology," *Cur. Opin. Genetic Develop.*, 3: 102–109 (1993).

Brenner, S. E., "Errors in genome annotation," *Trends in Genetics*, 15(4):132–133 (1999).

Brice et al., "Absence of the amyloid precursor protein gene mutation (APP717 : Val–>lle) in 85 cases of early onset Alzheimer's disease," *J. Neurology, Neurosurg. Psychiatry*, 56:112–115 (1993).

Cameron, "Recent Advances in Transgenic Technology," *Molecular Biotechnology*, 7:253–265 (1997).

Caputo et al., "Therapeutic approaches targeted at the amyloid proteins in Alzheimer's disease," *Clin. Neuropharm.*, 15:414A–414B (1992).

Castillo et al., "Amylin / Islet Amyloid Polypeptide: Biochemistry, Physiology, Patho–Physiology," *Diabete & Metabolisme (Paris)*, 21:3–25 (1995).

Center for Biologics Evaluation and Research, U.S. Food and Drug Administration, Thimerosal in Vaccines (Mercury in Plasma–Derived Products), web site contents found at: http://www.fda.gov/cber/vaccine/thimerosal.htm, last updated May 16, 2002.

Chao et al., "Transforming Growth Factor–β Protects human Neurons Against β–Amyloid–Induced Injury," *Soc. Neurosci. Abstracts*, 19:513–7 (1993).

Chapman, "Model behavior," *Nature*, 408:915–916 (2000).

Check, "Battle of the Mind," *Nature*, 422:370–372 (Mar. 2003).

Chemical Abstract database, Abstract of "Injection of Newborn Mice with Seven Chemical Adjuvants to Help Determine Their Safety in Use in Biologicals," Chemical Abstract database. (Publication date unknown).

Chen et al., "Neurodegenerative Alzheimer–like pathology in PDAPP 717V→F transgenic mice," *Progress in Brain Research*, Van Leeuwen et al. Eds, 117:327–337 (1998).

Chen et al., "An Antibody to β Amyloid Precursor Protein Inhibits Cell–substratum Adhesion in Many Mammalian Cell Types," *Neuroscience Letters*, 125:223–226 (1991).

Chen et al., "A learning deficit related to age and beta–amyloid plaques in a mouse model of Alzheimer's disease," *Nature*, 408(6815):975–9 (2000).

Chung et al., "Uptake, Degradation, and Release of Fibrillar and Soluble Forms of Alzheimer's Amyloid β–Peptide by Microglial Cells," *J. Biol. Chem.*, 274(45):32301–32308 (1999).

Coloma et al., "Transport Across the Primate Blood–Brain Barrier of a Genetically Engineered Chimeric Monoclonal Antibody to the Human Insulin Receptor," *Pharm. Res.*, 17:266–274 (2000).

Conway et al., "Acceleration of oligomerization, not fibrilization, is a shared property of both α–synuclein mutations linked to early–onset Parkinson's disease: Implications for pathogenesis and therapy," *PNAS*, 97(2):571–576 (2000).

Cordell, B., "β–Amyloid formation as a potential therapeutic target for Alzheimer's disease," *Ann. Rev. Pharmacol. Toxicol.*, 34:69–89 (1994).

Costa et al., "Immunoassay for transthyretin variants associated with amyloid neuropathy," *Scand. J. Immunol.*, 38:177–182 (1993).

Daly, et al., "Detection of the membrane–retained carboxy–terminal tail containing polypeptides of the amyloid precursor protein in tissue from Alzheimer's Disease brain," *Life Sci.*, 63:2121–2131 (1998).

Das et al., "Amyloid–β Immunization Effectively Reduces Amyloid Deposition in FcRy Knock–Out–Mice," *J. Neuroscience*, 23(24):8532–8538 (2003).

Demattos et al., "Peripheral Anti Aβ Antibody Alters CNS And Plasma Aβ Clearance and Decreases Brain Aβ Burden in a Mouse Model of Alzheimer's Disease," *Proc. Natl. Acad. Sci. USA,10,1073/pnas*.151261398 (2001).

Dialog/Derwent, Abstract of WPI Acc No: 1997–054436/ 199706: Stable vaccine compsns.—comprise a macrocyclic lactone, a milbemycin, an avemectin, an antigen, a dispersing agent, an adjuvant, a water sol. organic solvent and saline or water, Derwent File 351: Derwent WPI database. (Publication date unknown).

Dickson et al., "Neuroimmunology of Alzheimer's disease: a conference report," *Neurobiology of Aging*, 13(6):793–798 (1992), abstract only.

Diomede et al., "Activation effects of a prion protein fragment [PrP–(106–126)] on human leucocytes," *Biochem. J.*, 320:563–570 (1996).

Dodart, "Immunotherapy for Alzheimer's disease: will vaccination work?" *Trends in Molecular Medicine*, 9(3):85–87 (2003).

Doerks et al., "Protein annotation: detective work for function prediction," *Trends in Genetics*, 14(6):248–250 (1998).

Du et al., "Reduced levels of amyloid beta–peptide antibody in Alzheimer disease," *Neurology*, 57(5):801–5 (2001).

Duff et al., "Mouse model made," *Nature*, 373: 476–477 (1995).

Dumery et al., "β–Amyloid protein aggregation: its implication in the physiopathology of Alzheimer's disease," *Pathol. Biol.*, 49:72–85 (2001).

Eck et al., *Goodman and Gilman's The pharmacological basis of therapeutics*, Chapter 5, pp. 77–101 (1996).

Elan, "Elan and AHP Provide an Update on the Phase 2A Clinical Trial of AN–1792," Press Release. (Jan. 18, 2002).

Elan, "Elan and Wyeth Provide Update on Status of Alzheimer's Collaboration," Press Release (Mar. 1, 2002).

Elizan et al., "Antineurofilament antibodies in a postencephalitic and idiopathic Parkinson's disease," *J. Neurol. Sciences*, 59:341–347 (1983).

Esiri, "Is an effective immune Intervention for Alzheimer's disease in prospect?", *Trends in Pharm. Sci.*, 22:2–3 (2001).

Felsenstein et al., "Processing of the β–amyloid precursor protein carrying the familial, Dutch–type, and a novel recombinant C–terminal mutation," *Neuroscience Letters*, 152:185–189 (1993).

Felsenstein et al., "Transgenic Rat and In–Vitro Studies of β–Amyloid Precursor Protein Processing;" *Alzheimer's and Parkinson's Diseases*, Hanin et al. Ed., pp 401–409, Plenum Press, New York, (1995).

Finch et al., "Evolutionary Perspectives on Amyloid and Inflammatory Features of Alzheimer Disease," *Neurobiology of Aging*, 17(5):809–815 (1996).

Fisher et al., "Expression of the amyloid precursor protein gene in mouse oocytes and embryos," *PNAS*, 88:1779–1782 (1991).

Flanders et al., "Altered expression of transforming growth factor–β in Alzheimer's disease," *Neurology*, 45:1561–1569 (1995).

Fonseca et al., "The Presence of Isoaspartic Acid in β–Amyloid Plaques Indicates Plaque Age," *Experimental Neurology*, 157(2):277–288 (1999).

Frautschy et al., "Effects of injected Alzheimer β–amyloid cores in rat brain," *PNAS*, 88:8362–8366 (1991).

Frenkel et al., "Generation of auto–antibodies towards Alzheimer's disease vaccination," *Vaccine*, 19:2615–2619 (2001).

Frenkel et al., "High affinity binding of monoclonal antibodies to the sequential epitope EFRH of β–amyloid peptide is essential for modulation of fibrillar aggregation," *J. of Neuroimmunology*, 95:136–142 (1999).

Frenkel et al., "Immunization against Alzheimer's β–amyloid plaques via EFRH phage administration," *PNAS USA*, 97:11455–11459 (2000).

Frenkel et al., "N–terminal EFRH sequence of Alzheimer's β–amyloid peptide represents the epitope of its anti–aggregating antibodies," *J. of Neuroimmunology*, 88:85–90 (1998).

Frenkel, et al., "Modulation of Alzheimer's β–amyloid neurotoxicity by site–directed single chain antibody," *J. of Neuroimmunology*, 106:23–31 (2000).

Friedland et al., "Development of an Anti–Aβ monoclonal antibody for in vivo imaging of amyloid angiopathy in Alzheimer's disease," *Mol. Neurology*, 9:107–113 (1994).

Friedland, et al., "Neuroimaging of Vessel Amyloid in Alzheimer's Disease," *Cerebrovascular Pathology in Alzheimer's Disease*, eds. de la Torre and Hachinski, New York Academy of Sciences, New York, New York (1997).

Furlan et al., "Vaccination with amyloid–β peptide Induces autoimmune encephalomyelitis in C57/BL6 mice," *Brain*, 126:285–291 (2003).

Games et al., "Alzheimer–type neuropathology in transgenic mice overexpressing V717F β–amyloid precursor protein," *Nature*, 373(6514): 523–527 (1995).

Games et al., "Prevention and Reduction of AD–type Pathology in PDAPP Mice Immunized with $A\beta_{1-42}$," *Annals of the New York Academy of Science* 920:274–84 (2000).

Gandy et al., "Amyloidogenesis in Alzheimer's disease: some possible therapeutic opportunities," *TIPS*, 13:108–113 (1992).

Gardella et al., "Intact Alzheimer amyloid precursor protein (APP) is present in platelet membranes and is encoded by platelet mRNA," *Biochem. Biophys. Res. Comm.*, 173:1292–1298 (1990).

Gaskin et al., "Human antibodies reactive with beta–amyloid protein in Alzheimer's disease," *J. Exp. Med.*, 177:1181–1186 (1993).

Geddes, "N–terminus truncated β–amyloid peptides and C–terminus truncated secreted forms of amyloid precursor protein: distinct roles in the pathogenesis of Alzheimer's disease," *Neurobiology of Aging*, 20:75–79 (1999).

Giulian, et al., "The HHQK Domain of b–Amyloid Provides a Structural Basis for the Immunopathology of Alzheimer's Disease," *Journal of Biological Chem.*, 273:29719–29726 (1998).

Glenn et al., "Skin immunization made possible by cholera toxin," *Nature*, 391: 851 (1998).

Glenner et al., "Alzheimer's Disease and Downs Syndrome: Sharing of A Unique Cerebrovascular Amyloid Fibril Protein," *Biochemical and Biophysical Research Communications*, 122(3): 1131–1135 (1984).

Glenner et al., "Alzheimer's Disease: Initial Report of the Purification and Characterization of a Novel Cerebrovascular Amyloid Protein," *Biochemical and Biophysical Research Communications*, 120(3): 885–890 (1994).

Goate et al., "Segregation of a missense mutation in the amyloid precursor protein gene with familial Alzheimer's disease," *Nature*, 349:704–706 (1991).

Goldfarb et al. "The Transmissible Spongiform Encephalopathies," *Ann. Rev. Med.*, 46:57–65 (1995).

Goldsby et al., "Vaccines," Chapter 18 from *Immunology*, 4th Edition, W.H. Freeman and Company, New York, pp. 449–465.

Goldsteins et al., "Goldsteins et al., Exposure of cryptic epitopes on transthyretin only in amypoid and in amyloidogenic mutants," *PNAS*, 96:3108–3113 (1999).

Gonzales–Fernandez et al., "Low antige dose favors selection of somatic mutants with hallmarks of antibody affinity maturation," *Immunology*, 93:149–153 (1998).

Gortner, *Outlines of Biochemistry*, pp. 322–323, John Wiley & Sons, Inc., New York (1949).

Gozes et al., "Neuroprotective strategy for Alzheimer disease: Intranasal administration of a fatty neuropeptide," PNAS USA, 93:427–432 (1996).

Gravina et al., "Amyloid β Protein (Aβ) in Alzheimer's Disease," J. Biol. Chem., 270(13):7013–7016 (1995).

Grubeck–Loebenstein, et al., "Immunization with β–amyloid: could T–cell activation have a harmful effect?", TINS, 23:114 (2000).

Gupta et al., "Differences in the immunogenicity of native and formalized cross reacting material (CRM197) of diptheria toxin in mice and guinea pigs and their implications on the development and control of diphtheria vaccine based on CRMs," Vaccine, 15(12/13): 1341–1343 (1997).

Haass et al., "Amyloid beta–peptide is produced by culture cells during normal metabolism," Nature, 359(6393):322–5 (1992).

Haga et al., "Synthetic Alzheimer amyloid β/A4 peptides enhance production of complement C3 component by cultured microglial cells," Brain Research, 601:88–94 (1993).

Hanan and Solomon, "Inhibitory effect of monoclonal antibodies on Alzheimer's β–amyloid peptide aggregation," Int. J. Exp. Clin. Invest., 3:130–133 (1996).

Hanes et al., "New advances in microsphere–based single–dose vaccines," Advanced Drug Delivery Reviews, 28: 97–119 (1997).

Hardy, "Amyloid, the presenilins and Alzheimer's disease," TINS, 20(4): 154–159 (1997).

Hardy, John, "New Insights into the Genetics of Alzheimer's Disease," Annals of Med., 28:255–258 (1996).

Harigaya, et al., "Modified amyloid β protein ending at 42 or 40 with different solubility accumulates in the brain of Alzheimer's disease," Biochem. Biophys. Res. Comm., 211:1015–1022 (1995).

Harrington et al., "Charaterization of an epitope specific to the neuron–specific Isoform of human enolase recognized by a monoclonal antibody raised against a synthetic peptide corresponding to the C–terminus of β / A4–protein," Biochimica Biophysica Acta, 1158:120–128 (1993).

Hazama, et al., "Intranasal Immunization Against Herpes Simplex Virus Infection by Using a Recombinant Glycoprotein D Fused With Immunomodulating Proteins, the B Subunit of Escherichia coli Heat–Labile Enterotoxin and Interleukin–2", Immunology, vol. 78: 643–649 (1993).

Helmuth, "Further Progress on a β–Amyloid Vaccine," Science, 289:375 (2000).

Hilbrich et al., "Human and rodent sequence analogs of Alzheimer's amyloid βA4 share similar properties and can be solubilized in buffers of pH 7.4," Eur. J. Biochem., 201:61–69 (1991).

Holtzman et al., "Aβimmunization and anti–Aβ antibodies: potential therapies for the prevention and treatment of Alzheimer's disease," Advanced Drug Delivery Reviews, 54:1603–1613 (2002).

Hsiao et al., "Correlative Memory Deficits, Aβ Elevation, and Amyloid Plaques in Transgenic Mice," Science, 274: 99–102 (1996).

Huberman et al., "Correlation of cytokine secretion by mononuclear cells of Alzheimer's patients and their disease stage," J. Neuroimmunology, 52:147–152 (1994).

Human Immunology & Cancer Program brochure, from The University of Tennessee Medical Center/Graduate School of Medicine, Knoxville, Tennessee (publication date unknown).

Hyman et al., "Molecular Epidemiology of Alzheimer's Disease," N. E. J. Medicine, 333(19):1283–1284 (1995).

Ikeda, et al., "Immunogold labeling of cerebrovascular and neuritic plaque amyloid fibrils in Alzheimer's disease with an anti–β protein monoclonal antibody," Lab. Invest., 57:446–449 (1987).

Itagaki et al., "Relationship of microglia and astrocytes to amyloid deposits of Alzheimer's disease," J. Neuroimmunology, 24:173–182 (1989).

Iwatsubo et al., "Visualization of Aβ42(43) and Aβ40 in Senile Plaques with End–Specific AβMonoclonals: Evidence That an Initially Deposited Species is Aβ 42(43)," Neuron, 13:45–53 (1994).

Jakes et al., "Characterisation of an Antibody Relevant to the Neuropathology of Alzheimer Disease," Alzheimer Disease and Associated Disorders, 9(1):47–51, Raven Press, Ltd., New York (1995).

Jansen et al., "Immunotoxins: Hybrid Molecules Combining High Specificity and Potent Cytotoxicity," Immun. Rev., 62: 185–216 (1982).

Janus et al., "A beta peptide immunization reduces behavioural impairment and plaques in a model of Alzheimer's disease," Nature, 408(6815):979–82 (2000).

Jen, et al., "Preparation and purification of antisera against different regions or isoforms of b–amyloid precursor protein," Brain Research Protocols, 2:23–30 (1997).

Joachim et al., "Antibodies to Non–beta Regions of the Beta–amyloid Precursor Protein Detect a Subset of Senile Plaques," Am. J. of Pathology, 138:373–384 (1991).

Jobling and Holmes, "Analysis of structure and function of the B subunit of cholera toxin by the use of site–directed mutagenesis," Molecular Microbiology, 5(7):1755–1767 (1991).

Johnstone et al., Nuclear and Cytoplasmic Localization of the β–Amyloid Peptide (1–43) in Transfected 293 Cells, Biochemical and Biophysical Research Communications, 220:710–718 (1996).

Jorbeck et al., "Artificial Salmonella Vaccines: Salmonella typhimurium O–antigen–Specific Oligosaccharide–Protein Conjugates Elicit Opsonizing Antibodies that Enhance Phagocytosis," Infection and Immunity, May:497–502 (1981).

Kalaria, R. N., "Serum amyloid P and related molecules associated with the acute–phase response in Alzheimer's disease," Res. Immunology, 143:637–641 (1992).

Katzav–Gozansky et al., "Effect of monoclonal antibodies in preventing carboxypeptidase A aggregation," Biotechnol. Appl. Biochem., 23:227–230 (1996).

Kawabata et al., "Amyloid plaques, neurofibrillary tangles and neuronal loss in brains of transgenic mice overexpressing a C–terminal fragment of human amyloid precursor protein," Nature, 354:476–478 (1991).

Kelly, J. W., "Alternative conformations of amyloidogenic proteins govern their behavior," Current Opinion in Structural Biology, 6:11–17 (1996).

Kida, et al., "Early amyloid–β deposits show different immunoreactivity to the amino– and carboxy–terminal regions of b–peptide in Alzheimer's disease and Down's syndrome brain," Neuroscience Letters, 193:105–108 (1995).

Konig et al., "Development and Characterization of a Monoclonal Antibody 369.2B Specific for the Carboxyl–Terminus of the βA4 Peptide," Annals of NY Acad. Sci., 777:344–355 (1996).

Kovacs et al., "Mutations of the Prion Protein Gene Phenotypic Spectrum," *J. Neurol.*, 249:1567–1582 (2002).

Lampert–Etchells et al., "Regional Localization of Cells Containing Complement C1q and C4 mRNAs in the Frontal Cortex During Alzheimer's Disease," *Neurodegeneration*, 2:111–121 (1993).

Langer, "New Methods of Drug Delivery," *Science*, 249: 1527–1532 (1990).

Lannfelt et al., "Alzheimer's disease: molecular genetics and transgenic animal models," *Behavioural Brain Res.*, 57:207–213 (1993).

Lansbury, Peter T., "Inhibition of amyloid formation: a strategy to delay the onset of Alzheimer's disease," *Curr. Ops. in Chemical Biology*, 1:260–267 (1997).

Lemere et al., "Mucosal Administration of Aβ Peptide Decreases Cerebral Amyloid Burden In Pd–App Transgenic Mice," *Society for Neuroscience Abstracts*, vol. 25, part I, Abstract 519.6, 29th Annual Meeting, (Oct. 23–28, 1999).

Lemere, et al., "Nasal Aβ treatment induces anti–Aβ Antibody production and decreases cerebral amyloid burden in PD–APP mice," *Annals of the NY Acad. Sci.*, 920:328–331 (2000).

Li and Solomon, "Thermal Stabilization of Carboxypeptides A as a Function of PH and Ionic Milieu," *Biochem. Mol. Biol. Int.*, 43(3):601–611 (1997).

Livingston et al., "The Hepatitis B Virus–Specific CTL Responses Induced in Humans by Lipopeptide Vaccination Are Comparable to Those Elicited by Acute Viral Infection," *J. Immunol.*, 159:1383–1392 (1997).

Lopez et al., "Serum auto–antibodies in Alzheimer's disease," *Acta. Neurol. Scand.*, 84:441–444 (1991).

Majocha et al., "Development of a Monoclonal Antibody Specific for β/A4 Amyloid in Alzheimer's Disease Brain for Application to In Vitro Imaging of Amyloid Angiopathy," *The J. of Nuclear Med.* 33:2184–2189 (1992).

Mak, et al., "Polyclonals to b–amyloid (1–42) identify most plaque and vascular deposits in Alzheimer cortex, but not striatum," *Brain Research*, 667:138–142 (1994).

Mann, et al., "Amyloid β protein (Aβ) deposition in chromosome 14–linked Alzheimer's disease: Predominance of $A\beta_{42(43)}$," *Annals of Neurology*, 40:149–156 (1996).

Mann, et al., "The extent of amyloid deposition in brain in patients with Down's syndrome dose not depend upon the apolipoprotein E genotype," *Neuroscience Letters*, 196:105–108 (1995).

Marshall, E., "Gene Therapy's Growing Pains," *Science*, 269:1050–1055 (1995).

Masliah et al., "β–Amyloid peptides enhance α–synuclein accumulation and neuronal deficits in a transgenic mouse model linking Alzheimer's disease and Parkinson's disease," *PNAS*, 98(21):12245–12250 (2001).

Masters et al., "Amyloid Plaque core protein in Alzheimer Disease and Down Syndrome," *Proc. Natl. Acad. Sci. USA*, 82:4245–4249 (1985).

Mattson, Cellular actions of beta–amyloid precursor protein and its soluble and fibrillogenic derivatives. Physiol Rev. 77(4):1081–132 (1997).

McGee et al., "The encapsulation of a model protein in poly (D, L lactide–co–glycolide) microparticles of various sizes: an evaluation of process reproducibility," *J. Micro. Encap.*, 14(2): 197–210 (1997).

McGeer, et al., "Immunohistochemical localization of beta–amyloid precursor protein sequences in Alzheimer and normal brain tissue by light and electron microscopy," *J. of Neuroscience Res.*, 31:428–442 (1992).

McNeal et al., "Stimulation of local immunity and protection in mice by intramuscular immunization with triple– or double–layered rotavirus particles and QS–21," *Virology*, 243:158–166 (1998).

Meda et al., "Activation of microglial cells by β–amyloid protein and interferon–γ," *Nature*, 374:647–650 (1995).

Mena, et al., "Monitoring pathological assembly of tau and β–amyloid proteins in Alzheimer's disease," *Acta Neuropathol.*, 89:50–56 (1995).

Merluzzi, et al., "Humanized antibodies as potential drugs for therapeutic use," *Adv Clin Path.*, 4(2):77–85 (2000).

Miller et al., "Antigen–driven Bystander Suppression after Oral Administration of Antigens," *J. Exp. Med.*, 174:791–798 (1991).

Monsonego et al., "Immune hyporesponsiveness to amyloid β–peptide in amyloid precursor protein transgenic mice: Implications for the pathogenesis and treatment of Alzheimer's disease," *PNAS*, 98(18):10273–10278 (2001).

Morgan, et al., "A beta peptide vaccination prevents memory loss in an animal model of Alzheimer's disease," *Nature*. 408(6815):982–5 (2000).

Mori et al., "Mass Spectrometry of Purified Amyloid β Protein in Alzheimer's Disease," *J. Biol. Chem.*, 267(24):17082–17086 (1992).

Morris, et al., "The Consortium to Establish a registry for Alzheimer's Disease (CERAD)," *Neurology*, 39:1159–65 (1989).

Munch et al., "Potential neurotoxic inflammatory response to Aβ vaccination in humans," (2002) *J. Neural Transm.*, 109:1081–1087.

Munson ed., "Principals of Pharmacology: Basic Concepts & Clinical Applications," (1995), 47–48, Chapman & Hall, New York, New York.

Murphy et al., "Development of a Monoclonal Antibody Specific for the COOH–Terminal of β–Amyloid 1–42 and Its Immunohistochemical Reactivity in Alzheimer's Disease and Related Disorders," *Am. J. Pathology*, 144(5):1082–1088 (1994).

Mutschler et al., "Drug Actions: Basic Principles and Therapeutic Aspects," (1995) 7, 11–12, *medpharm* Scientific Publishers, Stuttgart, Germany.

Nakamura et al., "Histopathological studies on senile plaques and cerebral amyloid angiopathy in aged cynomologus monkeys," *Exp. Anim.*, 43:711–718 (1995).

Nakamura, et al., "Carboxyl end–specific monoclonal antibodies to amyloid β protein (Aβ) subtypes (Aβ40 and Aβ42(43) differentiate Ab in senile plaques and amyloid angiopathy in brains of aged cynomolgus monkeys," *Neuroscience Letters*, 201:151–154 (1995).

Nakayama et al., "Histopathological studies of senile plaques and cerebral amyloidosis in cynomolgus monkeys," *J. of Med. Primatology*, 27:244–252 (1998).

Nalbantoglu, J., "Beta–amyloid protein in Alzheimer's disease," *Can. J. Neurol. Sci.*, 18(3 suppl.):424–427 (1991), abstract only.

Nathanson et al., "Bovine Spongiform Encephalopathy (BSE): Causes and Consequences of a Common Source Epidemic," *Am. J. Epidemiol.*, 145(11): 959–969 (Jun. 1, 1997).

New York Times National, "Anti–Inflammatory Drugs May Impede Alzheimer's," (Feb. 20, 1994).
Newcombe and Cohen, "Solubility characteristics of isolated amyloid fibrils," Biochim. Biophys. Acta, 104:480–486 (1965).
Ngo et al., "Computational Complexity, Protein Structure Prediction, and the Levinthal Paradox," pp. 492–495 from Chapter 14 of The Protein Folding Problem and Tertiary Structure Prediction, Merz et al., eds., Birkhauser Boston (1994).
Nicoll et al., "Neuropathology of human Alzheimer's disease after immunization with amyloid–β peptide: a case report," Nature Medicine, 9(4):448–452 (Apr. 2003 ).
Niemann, "Transgenic farm animals get off the ground;" Transgenic Research 7:73–75 (1998).
Orkin et al., Report and Recommendations of the Panel to Assess the NIH Investment in Research on Gene Therapy, Dec. 7, 1995.
Palha et al., "Antibody recognition of amyloidogenic transthyretin variants in serum of patients with familial amyloidiotic polyneuropathy. " J. Mol. Med., 7:703–707 (2001).
Pan et al., "Antibodies to β–Amyloid Decrease the Blood-to–Brain Transfer of β–Amyloid Peptide," Exp. Biol. Med., 227(8):609–615 (2002).
Pardridge et al., "Chimeric peptides as a vehicle for peptide pharmaceutical delivery through the blood–brain barrier," Biochem. Biophys. Res. Comm., 146:307–313 (1987).
Paresce et al., "Microglial cells influence aggregates of the Alzheimer's disease amyloid beta–protein via a scavenger receptor," Neuron, 17:553–565 (Sep. 1996).
Paul et al., "Transdermal immunization with large proteins by means of ultradeformable drug carriers," Eur. J. Immunol., 25: 3521–3524 (1995).
Persson et al., "IgG subclass–associated affinity differences of specific antibodies in humans," J. Immunology, 140(11):3875–3879 (1988), abstract only.
Perutz et al., "Amyloid fibers are water–filled nanotubes," PNAS, 99(8):5591–5595 (2002).
Peterson, et al., "Recombinant Antibodies: Alternatives Strategies for Developing and Manipulating Murine–Derived Monoclonal Antibodies," Laboratory Animal Science, 46(1):8–14 (1996).
Philippe, et al., "Generation of a monoclonal antibody to the carboxy–terminal domain of tau by immunization with the amino–terminal domain of the amyloid precursor protein," J. of Neuroscience Res., 46:709–719 (1996).
Prieels et al., "Synergistic adjuvants for vaccines," Chemical Abstracts, 120(8): p. 652, column 1, abstract 88406t (1994).
Prusiner et al., "Ablation of the prion protein (PrP) gene in mice prevents scrapie and facilitates production of anti–PrP antibodies," PNAS, 90:10608–10612 (1993).
Quon et al., "Formation of β–Amyloid protein deposits in brains of transgenic mice," Nature, 352:239–241 (1991).
Raso, "Immunotherapy of Alzheimer's Disease," Immunotherapy Weekly, Abstract (Apr. 2, 1998).
Raso, V.A., Grant application # 1 R43 AGI 5746–01 (non–redacted version), "Immunotherapy of Alzheimer's Disease" (publication date unknown).
Raso, V.A., Grant application # 1 R43 AGI 5746–01 (redacted version), "Immunotherapy of Alzheimer's Disease" (publication date unknown).
Rogers et al., "Complement activation by β–amyloid in Alzheimer Disease," PNAS, 89:1–5 (1992).
Rossor et al., "Alzheimer's Disease Families with Amyloid Precursor Protein Mutations," Annals of New York Academy of Sciences, 695:198–202 (1993).
Rudinger, "Characteristics of the Amino Acids as Components of a Peptide Hormone Sequence," In Peptide Hormones, J.A. Parson, ed. University Park Press, Baltimore, pp 1–7 (1976).
Saido et al., "Spatial Resolution of Fodrin Proteolysis in Postischemic Brain," J. Biol. Chem., 268(33):25239–25243 (1993).
Saido et al., "Spatial Resolution of the Primary β–Amyloidogenic Process Induced in Postischemic Hippocampus," J. Biol. Chem., 269(21):15253–15257 (1994).
Saito et al., "Vector–mediated delivery of $^{125}$I–labeled β–amyloid peptide $Ab^{1-40}$ through the blood–brain barrier and binding to Alzheimer disease amyloid of the $A\beta^{1-40}$ vector complex," PNAS USA, 92:10227–10231 (1995).**.
Saitoh, N. et al., "Immunological analysis of Alzheimer's disease using anti– β–protein monoclonal antibodies," Sapporo Med. J., 60:309–320 (1991).
Sasaki et al., "Human choroid plexus is an uniquely involved area of the brain in amyloidosis: a histochemical, immunohistochemical and ultrastructural study," Brain Res., 755:193–201 (1997).
Schenk et al., "Immunization with amyloid–βattenuates Alzheimer–disease–like pathology in the PDAPP mouse," Nature, 400:173–177 (1999).
Schenk et al., "Therapeutic Approaches Related to Amyloid–β Peptide and Alzheimer's Disease," J. Med. Chem., 38(21):4141–4154 (1995).
Schenk et al., "Immunotherapy with beta–amyloid for Alzheimer's disease: a new frontier," DNA Cell Biol., 20(11):679–81 (2001).
Schenk et al., "β–peptide immunization," Arch. Neurol., 57:934–936 (2000).
Schenk, D., "Amyloid–βimmunotherapy for Alzheimer's disease: the end of the beginning," Nature Reviews, 3:842–828 (2002).
Selkoe, "Alzheimer's Disease: A Central Role for Amyloid," J. Neuropathol. Exp. Neurol., 53(5): 438–447 (1997).
Selkoe, "Physiological production of the β–amyloid protein and the mechanism of Alzheimer's disease," Trends in Neurosciences, 16(10): 403–409 (1993).
Selkoe, D.J., "Imaging Alzheimer's Amyloid," Nat. Biotech., 18:823–824 (2000).
Selkoe, Dennis J., "Alzheimer's Disease: Genotypes, Phenotype, and Treatments," Science, 275:630–631 (1997).
Selkoe, Dennis J., "Amyloid Protein and Alzheimer's Disease . . . ," Scientific American, pp. 68–78 (Nov., 1991).
Selkoe, Dennis J., "In the Beginning . . . ," Nature, 354:432–433 (1991).
Selkoe, Dennis J., "The Molecular pathology of Alzheimer's Disease," Neuron, 6:487–498 (1991).
Selkoe, "The cell biology of beta–amyloid precursor protein and presenllin in Alzheimer's disease," Trends Cell Biol., 8(11):447–53 (1998).
Seubert et al., "Isolation and quantification of soluble Alzheimer's β–peptide from biological fluids," Nature, 359:325–327 (1992).
Shiosaka, S., "Attempts to make models for Alzheimer'disease," Neuroscience Res., 13:237–255 (1992).
Sigmund, "Viewpoint: Are Studies in Genetically Altered Mice Out of Control,"Arterioscler Thromb Vasc Biol., 20:1425–1429 (2000).

Sigurdsson et al., "Anti–priori antibodies for prophylaxis following prion exposure in mice," *Neurosciences Letters*, 336:185–187 (2003).

Sigurdsson et al., "Immunization Delays the Onset of Prion Disease in Mice," *American Journal of Pathology*, 161:13–17 (2002).

Sigurdsson, et al., "In vivo reversal of amyloid–beta lesions in rat brain," *J Neuropathol Exp Neurol.*, 59(1):11–17 (2000).

Sigurdsson et al., "A safer vaccine for Alzheimer's disease?," *Neurobiology of Aging*, 23:1001–1008 (2002).

Singh, K.S., "Neuroautoimmunity: Pathogenic Implications for Alzheimer's Disease," *Gerontology*, 43:79–94 (1997).

Singh, V.K., "Studies of neuroimmune markers in Alzheimer's disease," *Mol. Neurobiology*, 9(1–3):73–81 (1994), abstract only.

Sinha, et al., "Recent advances in the understanding of the processing of APP to beta amyloid peptide," *Ann N Y Acad Sci.*, 920:206–8 (2000).

SIPE, "Amyloidosis," *Annu. Rev. Biochem.*, 61:947–975 (1992).

Skolnick and Fetrow, "From genes to protein structure and function: novel applications of computational approaches in the genomic era," *Trends in Biotech*, 18(1):34–39 (2000).

Small, et al. Alzheimer's disease and Abeta toxicity: from top to bottom. Nat Rev Neurosci. 2(8):595–8 (2001).

Smith et al., "The challenges of genome sequence annotation or 'The devil is in the details,'" *Nature Biotechnology*, 15:1222–1223 (1997).

Smits et al., "Prion Protein and Scrapie Susceptibility," *Vet. Quart.*, 19(3): 101–105 (1997).

Solomon and et al., "Modulation of The Catalytic Pathway of Carboxypeptidase A by Conjugation with Polyvinyl Alcohols," *Adv. Mol. Cell Biology*, 15A:33–45 (1996).

Solomon et al., "Activity of monoclonal antibodies in prevention of in vitro aggregation of their antigens," abstract from Department of Molecular Microbiology and Biotechnology, Tel Aviv University, Tel Aviv, Israel (publication date unknown).

Solomon et al., "Disaggregation of Alzheimer β–amyloid by site–directed mAb," *PNAS USA*, 94:4109–4112 (1997).

Solomon et al., "Monoclonal antibodies inhibit in vitro fibrillar aggregation of the Alzheimer β–amyloid peptide," *PNAS USA*, 93:452–455 (1996).

Solomon, A., "Pro–Rx (Protein Therapeutics)," University of Tennessee Medical Center (publication date unknown).

Solomon, B., "New Approach Towards Fast Induction of Anti β–Amyloid Peptide Immune Response," Department of Molecular Microbiology & Biotechnology, Tel–Aviv University, Ramat Aviv, Tel–Aviv, Israel (publication date unknown).

Solomon et al., "The Amino Terminus of the β–Amyloid Peptide Contains as Essential Epitope for Maintaining Its Solubility," from *Progress in Alzheimer's and Parkinson's Diseases*, edited by Fisher et al., Plenum Press, New York, pp. 205–211 (1995).

Soto, et al. Beta sheet breaker peptides inhibit fibrilogenesis in a rat brain model of amyloidosis: implications for Alzheimer's therapy. Nat Med. 4(7):822–6 (1998).

Southwick et al., "Assessment of Amyloid β protein in Cerebrospinal fluid as an Aid in the Diagnosis of Alzheimer's Disease," *J. Neurochemistry*, 66:259–265 (1996).

Spooner et al., "The generation and characterization of potentially therapeutic Aβ antibodies in mice: differences according to strain and immunization protocol," *Vaccine*, 21:290–297 (2002).

St. George–Hyslop et al., "Antibody clears senile plaques," *Nature*, 40:116–117 (1999).

Stein et al., "Lack of Neurodegeneration in Transgenic Mice Overexpressing Mutant Amyloid Precursor Protein is Associated with Increased Levels of Transthyretin and Activation of Cell Survival Pathways," *The Journal of Neuroscience*, 22(17):7380–7388 (Sep. 1, 2002).

Stern et al., "Antibodies to the β–amyloid peptide cross–react with conformational epitopes in human fibrinogen subunits from peripheral blood," *FEBS Letters*, 264(1):43–47 (1990).

Stoute et al., "A Preliminary Evaluation of a Recombinant Circumsporozoite Protein Vaccine Against *Plasmodium Falciparum Malaria*", *N. Engl. J. Med.*, 336(2): 86–91 (1997).

Sturchler–Pierrat et al., "Two amyloid precursor protein transgenic mouse models with Alzheimer disease–like pathology," *PNAS*, 94: 13287–13292 (1997).

Su et al., "Intravascular infusions of soluble β–amyloid compromise the blood–brain barrier, activate CNS Glial cells and induce peripheral hemorrhage," *Brain Research*, 818:105–107 (1999).

Szendrei, et al., "The effects of aspartic acid–bond isomerization on in vitro properties of the amyloid β–peptide as modeled with N–terminal decapeptide fragments," *Int. J. Peptide Protein Res.*, 47:289–296 (1996).

Tal et al., "Complete Freund's Adjuvant Immunization Prolongs Survival in Experimental Prion Disease in Mice," *Journal of Neuroscience Research*, 71:286–290 (2003).

Tan et al., "Amyloidosis," *Histopathology*, 25:403–414 (1994).

Tanaka et al., "NC–1900, an active fragment analog of arginine vasopressin, improves learning and memory deficits induced by beta–amyloid protein in rats," *European J. Pharmacology*, 352:135–142 (1998).

Tennent et al., "Serum amyloid P component Prevents proteolysis of the amyloid fibrils of Alzheimer's disease and systemic amyloidosis," *PNAS*, 92:4299–4303 (1995).

Thorsett, E.D. et al., "Therapeutic approaches to Alzheimer's disease," *Curr. Op. in Chem. Biology*, 4:377–382 (2000).

Tjernberg et al., "Arrest of β–amyloid fibril formation by a pentapeptide ligand," *Journal of Biological Chemistry*, 271:8545–8548 (1996).

Trieb et al., "Is Alzheimer beta amyloid precursor protein (APP) an autoantigen? Peptides corresponding to parts of the APP sequence stimulate T lymphocytes in normals, but not in patients with Alzheimer's disease," *Immunobiology*, 191(2–3):114–115 Abstract C.37, (1994).

Tsuzuki et al., "Amyloid β protein in rat soleus in choroquine–induced myopthy using end–specific antibodies for Aβ40 and Aβ42: Immunohistochemical evidence for amyloid βprotein," *Neuroscience Letters*, 2002:77–80 (1995).

Van Gool et al., "Concentrations of amyloid–β protein in cerebrospinal fluid increase with age in patients free from neurodegenerative disease," *Neuroscience Letters*, 172:122–124 (1994).

Vehmas, et al. beta–Amyloid peptide vaccination results in marked changes in serum and brain Abets levels in APPswe/PS1 DeltaE9 mice, as detected by Seldi–TOF–based ProteinChip® technology. DNA Cell Biol. (11):713 21 (2001).

Velazquez et al., "Aspartate residue 7 in amyloid β–protein is critical for classical complement pathway activation: Implications for Alzheimer's disease pathogenesis," *Nature Medicine*, 3(1):77–79 (1997).

Verbeek et al., "Accumulation of Intercellular Adhesion Molecule–1 in Senile Plaques in Brain Tissue of patients with Alzheimer's Disease," *Amer. Journ. Pathology*, 144(1):104–116 (1994).

Verma et al., "Gene therapy—promises, problems and prospects," *Nature*, 389:239–242 (1997).

Walker et al., "Labeling of Cerebral Amyloid In Vivo with a Monoclonal Antibody," *J. Neuropath. Exp. Neurology*, 53(4):377–383 (1994).

Weiner et al., "Nasal administration of amyloid–β peptide decreases cerebral amyloid burden in a mouse model of Alzheimer's disease," *Annals of Neurology*, 48:567–579 (2000).

Weiner et al., "Oral Tolerance: Immunologic Mechanisms and Treatment of Animal and Human Organ–Specific Autoimmune Diseases by Oral Administration of Autoantigens," *Annu. Rev. Immunol.*, 12:809–837 (1994).

Weissman et al., "Bovine spongiform encephalopathy and early onset variant Creutzfeldt–Jakob disease," *Curr. Opin. Neurobiol.*, 7: 695–700 (1997).

Weldon et al., "Neurotoxicity of Aβ Peptide: Confocal Imaging of Cellular Changes Induced by—Amyloid in Rat CNS In Vivo," *Society for Neuroscience Abstracts*, 22(Part 1) (1996).****.

Wells, J. A., "Additivity of Mutational Effects in Proteins," *Biochemistry*, 29(37):8509–8517 (1990).

Wen, G.Y., "Alzheimer's Disease and Risk Factors," *J. Food Drug Analysis*, 6(2):465–476 (1998).

Wengenack et al., "Targeting Alzheimer amyloid plaques in vivo," *Nature Biotech.*, 18:868–872 (2000).

Wisconsin Alumni Research Foundation, "Injection of Newborn Mice with Seven Chemical Adjuvants to Help Determine Their Safety in Use in Biologicals", U.S. Govt. Res. Develop. Rep., 70(24), 56. (Publication date unknown).

Wisniewski et al., "Therapeutics in Alzheimer's and Prion Diseases," *Biochemical Society Transactions*, 30(4):574–587 (2002).

Wong et al., "Neuritic Plaques and Cerebrovascular Amyloid in Alzheimer Disease are Antigenically Related," *PNAS USA*, 82:8729–8732 (1985).

Wood et al., "Amyloid precursor protein processing and Aβ42 deposition in a transgenic mouse model of Alzheimer disease," *PNAS USA*, 94: 1550–1555 (1997).

Wu, et al., "Drug targeting of a peptide radiopharmaceutical through the primate blood–brain barrier in vivo with a monoclonal antibody to the human insulin receptor," *J. Clin. Invest.*, 100:1804–1812 (1997).

Yamaguchi et al., Diffuse plaques associated with astroglial amyloid β protein, possibly showing a disappearing stage of senile plaques, *Acta Neuropathol.*, 95:217–222 (1998).

Yang et al., "Effects of Racemization on the Aggregational Properties of the Amyloid β–Peptide in Alzheimer's Disease," abstract # 255 from American Chemical Society 214th National Meeting (1997).

Younkin, "Amyloid β vaccination: reduced plaques and improved cognition," *Nature Medicine*, 7:18–19 (2001).

CORTEX

| PBS CONTROL | | UNTREATED CONTROL | |
|---|---|---|---|
| 624-165 | 272 | 764-181 | 3470 |
| 625-166 | 1802 | 785-182 | 171 |
| 626-167 | 62 | 766-183 | 91 |
| 633-168 | 4696 | 767-184 | 6692 |
| 634-169 | 3090 | 768-185 | 1353 |
| 671-170 | 2417 | 771-186 | 1153 |
| 672-171 | 2840 | 772-187 | 3800 |
| 829-172 | 3320 | 780-188 | 3740 |
| 830-173 | 1833 | 843-189 | 163 |
| 831-174 | 416 | 844-190 | 122 |
| 792-175 | 126 | 845-191 | 427 |
| 793-176 | 2559 | 846-192 | 2674 |
| 794-177 | 289 | 887-193 | 453 |
| 732-178 | 179 | 888-194 | 2996 |
| 733-179 | 1329 | 889-195 | 1075 |
| 734-180 | 5665 | | |
| MEDIAN p VALUE (M-W) | 1817 | MEDIAN p VALUE (M-W) | 1153 |
| MEAN ST. DEV. % CV p VALUE (t TEST) | 1931 1718 89 n=16 | MEAN ST. DEV. % CV p VALUE (t TEST) | 1825 1769 97 n=15 |

FIG. 15A

CORTEX

| 2 mg ALUM 100 μg AN1528 | | 50 μg ALUM 100 μg AN1528 | |
|---|---|---|---|
| 660-083 | 295 | 643-105 | 385 |
| 661-084 | 3180 | 644-106 | 2640 |
| 662-085 | 2480 | 645-107 | 2403 |
| 633-086 | 3014 | 654-108 | 1741 |
| 664-087 | 5870 | 655-109 | 3053 |
| 665-088 | 5978 | 656-110 | 5990 |
| 693-089 | 1620 | 678-111 | 3360 |
| 694-090 | 35 | 679-112 | 1230 |
| 695-091 | 3400 | 704-114 | 2680 |
| 697-092 | 2630 | 705-115 | 78 |
| 698-093 | 983 | 706-116 | 1290 |
| 699-094 | 5327 | 729-117 | 3180 |
| 701-095 | 1862 | 730-118 | 1833 |
| 702-096 | 1849 | 731-119 | 4590 |
| 703-097 | 2239 | 736-120 | 1112 |
| 739-098 | 806 | 737-121 | 1653 |
| 740-099 | 5303 | 757-122 | 992 |
| 741-100 | 459 | 758-123 | 4692 |
| 800-103 | 154 | 808-124 | 785 |
| 801-104 | 852 | 809-125 | 244 |
| | | 810-126 | 32 |
| MEDIAN p VALUE (M-W) | 2051 | MEDIAN p VALUE (M-W) | 1741 |
| MEAN ST. DEV. % CV p VALUE (t TEST) | 2407 1913 79 | MEAN ST. DEV. % CV p VALUE (t TEST) | 2140 1659 78 |
| | n=20 | | n=21 |

FIG. 15B

CORTEX

| 25 μg QS21 100 μg AN1528 | | CFA/IFA 100 μg AN1792 | |
|---|---|---|---|
| 615-128 | 1257 | 539-068 | 693 |
| 616-129 | 361 | 640-069 | 508 |
| 617-130 | 1008 | 641-070 | 440 |
| 536-131 | 3290 | 642-071 | 467 |
| 637-132 | 2520 | 690-072 | 42 |
| 638-133 | 3880 | 691-073 | 2491 |
| 744-134 | 627 | 692-074 | 121 |
| 745-135 | 58 | 795-075 | 137 |
| 746-136 | 2610 | 796-076 | 822 |
| 747-137 | 1509 | 797-077 | 475 |
| 769-138 | 1788 | 748-087 | 600 |
| 770-139 | 988 | 749-079 | 78 |
| 773-140 | 1199 | 750-080 | 1267 |
| 774-141 | 339 | 751-081 | 1351 |
| 775-142 | 402 | 761-082 | 69 |
| 776-143 | 537 | | |
| 840-144 | 1119 | | |
| 841-145 | 194 | | |
| 821-146 | 1259 | | |
| 822-147 | 5413 | | |
| 823-148 | 2233 | | |
| MEDIAN | 1199 | MEDIAN | 475 |
| p VALUE (M-W) | | p VALUE (M-W) | 0.0481 |
| MEAN | 1552 | MEAN | 637 |
| ST. DEV. | 1364 | ST. DEV. | 655 |
| % CV | 88 | % CV | 103 |
| p VALUE (t TEST) | | p VALUE (t TEST) | 0.0106 |
| | n=21 | | n=15 |

FIG. 15C

CORTEX

| 5 µg THIMEROSAL/PBS<br>10 µg AN1792 | | 2 mg ALUM<br>100 µg AN1792 | |
|---|---|---|---|
| 635-149 | 1337 | 610-001 | 432 |
| 669-150 | 4644 | 611-002 | 1012 |
| 670-151 | 6335 | 612-003 | 3607 |
| 673-152 | 3700 | 613-004 | 508 |
| 674-153 | 2750 | 620-005 | 465 |
| 676-154 | 1687 | 621-006 | 16 |
| 681-156 | 185 | 622-007 | 28 |
| 682-157 | 8031 | 623-008 | 217 |
| 683-158 | 3450 | 708-009 | 2738 |
| 754-159 | 157 | 709-010 | 927 |
| 755-160 | 6857 | 710-011 | 1609 |
| 756-161 | 482 | 716-012 | 1608 |
| 805-162 | 524 | 784-014 | 3890 |
| 806-163 | 397 | 785-015 | 1614 |
| 807-164 | 234 | 786-018 | 285 |
| | | 787-017 | 3102 |
| | | 788-018 | 1617 |
| | | 789-019 | 1474 |
| | | 815-020 | 424 |
| | | 816-021 | 1375 |
| | | 817-022 | 2323 |
| MEDIAN<br>p VALUE (M-W) | 1687 | MEDIAN<br>p VALUE (M-W) | 1375<br>0.5000 |
| MEAN<br>ST. DEV.<br>% CV<br>p VALUE (t TEST)<br> | 2718<br>2685<br>99<br><br>n=15 | MEAN<br>ST. DEV.<br>% CV<br>p VALUE (t TEST)<br> | 1394<br>1166<br>84<br>0.2650<br>n=21 |

FIG. 15D

CORTEX

| 50 µg MPL 100 µg AN1792 | | 25 µg QS21 100 µg AN1792 | |
|---|---|---|---|
| 646-023 | 2002 | 627-045 | 91 |
| 647-024 | 147 | 628-046 | 3397 |
| 648-025 | 1304 | 631-049 | 3702 |
| 649-026 | 34 | 632-050 | 1776 |
| 650-027 | 980 | 667-052 | 1832 |
| 724-028 | 1282 | 668-053 | 3023 |
| 726-030 | 1966 | 686-054 | 189 |
| 727-031 | 733 | 687-055 | 891 |
| 720-032 | 2563 | 688-056 | 240 |
| 721-033 | 5563 | 689-057 | 110 |
| 802-034 | 113 | 712-059 | 3311 |
| 803-035 | 671 | 825-061 | 1009 |
| 804-036 | 51 | 826-082 | 18165 |
| 811-037 | 613 | 827-063 | 73 |
| 812-038 | 332 | 828-064 | 78 |
| 813-039 | 1454 | 837-065 | 1051 |
| 814-040 | 2441 | 838-066 | 270 |
| 833-014 | 742 | 839-067 | 371 |
| 834-042 | 40 | | |
| 836-044 | 807 | | |
| MEDIAN | 774 | MEDIAN | 950 |
| p VALUE (M-W) | 0.1710 | p VALUE (M-W) | 0.4076 |
| MEAN | 1192 | MEAN | 2199 |
| ST. DEV. | 1299 | ST. DEV. | 4187 |
| % CV | 109 | % CV | 190 |
| p VALUE (t TEST) | 0.1506 | p VALUE (t TEST) | 0.8131 |
| | n=21 | | n=18 |

FIG. 15E

SEQUENCE LISTING

<160> NUMBER OF SEQ ID NOS: 5

<210> SEQ ID NO 1
<211> LENGTH: 42
<212> TYPE: PRT
<213> ORGANISM: Homo sapiens
<220> FEATURE:
<223> OTHER INFORMATION: human Abeta42 beta-amyloid peptide

<400> SEQUENCE: 1

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence:Abeta1-12
      peptide with carboxyl terminal Cys residue
      inserted

<400> SEQUENCE: 2

Asp Ala Glu Phe Arg His Asp Ser Gly Tyr Glu Val Cys
 1               5                  10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:Abeta1-5
      peptide with carboxyl terminal Cys residue
      inserted

<400> SEQUENCE: 3

Asp Ala Glu Phe Arg Cys
 1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence:Abeta33-42
      peptide with carboxyl terminal Cys residue
      inserted
<220> FEATURE:
<221> NAME/KEY: MOD_RES
<222> LOCATION: (2)
<223> OTHER INFORMATION: Xaa = amino hepatanoic acid

<400> SEQUENCE: 4

Cys Xaa Gly Leu Met Val Gly Gly Val Val Ile Ala
 1               5                  10

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence:Abeta13-28
      peptide with carboxyl terminal Cys residue
      inserted and two added Gly residues
<220> FEATURE:
<221> NAME/KEY: MOD_RES -continued

```
<222> LOCATION: (1)
<223> OTHER INFORMATION: Xaa = acetyl histidine

<400> SEQUENCE: 5

Xaa His Gln Lys Leu Val Phe Phe Ala Glu Asp Val Gly Ser Asn Lys
 1               5                  10                  15

Gly Gly Cys
```

PREVENTION AND TREATMENT OF AMYLOIDOGENIC DISEASE

CROSS-REFERENCE TO RELATED APPLICATIONS

This application is a continuation of U.S. application Ser. No. 09/201,430, filed Nov. 30, 1998 now U.S. Pat. No. 6,787,523, which claims the benefit under 35 U.S.C. 119(e) of U.S. application Ser. No. 60/080,970, filed Apr. 7, 1998 and U.S. application Ser. No. 60/067,740, filed Dec. 2, 1997, both of which are incorporated by reference in their entirety for all purposes.

BACKGROUND OF THE INVENTION

Alzheimer's disease (AD) is a progressive disease resulting in senile dementia. See generally Selkoe, TINS 16, 403–409 (1993); Hardy et al., WO 92/13069; Selkoe, J. Neuropathol. Exp. Neurol. 53, 438–447 (1994); Duff et al., Nature 373, 476–477 (1995); Games et al., Nature 373, 523 (1995). Broadly speaking the disease falls into two categories: late onset, which occurs in old age (65+years) and early onset, which develops well before the senile period, i.e, between 35 and 60 years. In both types of disease, the pathology is the same but the βnormalities tend to be more severe and widespread in cases beginning at an earlier age. The disease is characterized by two types of lesions in the brain, senile plaques and neurofibrillary tangles. Senile plaques are areas of disorganized neuropil up to 150 μm across with extracellular amyloid deposits at the center visible by microscopic analysis of sections of brain tissue. Neurofibrillary tangles are intracellular deposits of tau protein consisting of two filaments twisted about each other in pairs.

The principal constituent of the plaques is a peptide termed Aβ or β-amyloid peptide. Aβ peptide is an internal fragment of 39–43 amino acids of a precursor protein termed amyloid precursor protein (APP). Several mutations within the APP protein have been correlated with the presence of Alzheimer's disease. See, e.g., Goate et al., Nature 349, 704) (1991) (valine$^{717}$ to isoleucine); Chartier Harlan et al. Nature 353, 844 (1991)) (valine$^{717}$ to glycine); Murrell et al., Science 254, 97 (1991) (valine$^{717}$ to phenylalanine); Mullan et al., Nature Genet. 1, 345 (1992) (a double mutation changing lysine$^{595}$-methionine$^{596}$ to Nature Genet. 1, 345 (1992) (a double mutation changing lysine$^{595}$-methionine$^{596}$ to asparagine$^{595}$-leucine$^{596}$). Such mutations are thought to cause Alzheimer's disease by increased or altered processing of APP to Aβ, particularly processing of APP to increased amounts of the long form of Aβ (i.e., Aβ1-42 and Aβ1-43). Mutations in other genes, such as the presenilin genes, PS1 and PS2, are thought indirectly to affect processing of APP to generate increased amounts of long form Aβ (see Hardy, TINS 20, 154 (1997)). These observations indicate that Aβ, and particularly its long form, is a causative element in Alzheimer's disease.

McMichael, EP 526,511, proposes administration of homeopathic dosages (less than or equal to 10$^{-2}$ mg/day) of Aβ to patients with preestablished AD. In a typical human with about 5 liters of plasma, even the upper limit of this dosage would be expected to generate a concentration of no more than 2 pg/ml. The normal concentration of Aβ in human plasma is typically in the range of 50–200 pg/ml (Seubert et al., Nature 359, 325–327 (1992)). Because EP 526,511's proposed dosage would barely alter the level of endogenous circulating Aβ and because EP 526,511 does not recommend use of an adjuvant, it seems implausible that any therapeutic benefit would result.

By contrast, the present invention is directed inter alia to treatment of Alzheimer's and other amyloidogenic diseases by administration of Aβ or other immunogen to a patient under conditions that generate a beneficial immune response in the patient. The invention thus fulfills a longstanding need for therapeutic regimes for preventing or ameliorating the neuropathology of Alzheimer's disease.

SUMMARY OF THE CLAIMED INVENTION

In one aspect, the invention provides methods of preventing or treating a disease characterized by amyloid deposition in a patient. Such methods entail inducing an immune response against a peptide component of an amyloid deposit in the patient. Such induction can be active by administration of an immunogen or passive by administration of an antibody or an active fragment or derivative of the antibody. In some patients, the amyloid deposit is aggregated Aβ peptide and the disease is Alzheimer's disease. In some methods, the patient is asymptomatic. In some methods, the patient is under 50 years of age. In some methods, the patient has inherited risk factors indicating susceptibility to Alzheimer's disease. Such risk factors include variant alleles in presenilin gene PS1 or PS2 and variant forms of APP. In other methods, the patient has no known risk factors for Alzheimer's disease.

For treatment of patients suffering from Alzheimer's disease, one treatment regime entails administering a dose of Aβ peptide to the patient to induce the immune response. In some methods, the Aβ peptide is administered with an adjuvant that enhances the immune response to the Aβ peptide. In some methods, the adjuvant is alum. In some methods, the adjuvant is MPL. The dose of Aβ peptide administered to the patient is typically at least 1 or 10 μg, if administered with adjuvant, and at least 50 μg if administered without adjuvant. In some methods, the dose is at least 100 μg.

In some methods, the Aβ peptide is Aβ1-42. In some methods, the Aβ peptide is administered in aggregated form. In other methods, the Aβ peptide is administered in dissociated form. In some methods, the therapeutic agent is an effective dose of a nucleic acid encoding Aβ or an active fragment or derivative thereof. The nucleic acid encoding Aβ or fragment thereof is expressed in the patient to produce Aβ or the active fragment thereof, which induces the immune response. In some such methods, the nucleic acid is administered through the skin, optionally via a patch. In some methods, a therapeutic agent is identified by screening a library of compounds to identify a compound reactive with antibodies to Aβ, and administering the compound to the patient to induce the immune response.

In some methods, the immune response is directed to aggregated Aβ peptide without being directed to dissociated Aβ peptide. For example, the immune response can comprise antibodies that bind to aggregated Aβ peptide without binding to dissociated Aβ peptide. In some methods, the immune response comprises T-cells that bind to Aβ complexed with MCH1 or MHCII on CD8 or CD4 cells. In other methods, the immune response is induced by administering an antibody to Aβ to the patient. In some methods, the immune response is induced by removing T-cells from the patient, contacting the T-cells with Aβ peptide under conditions in which the T-cells are primed, and replacing the T-cells in the patient.

The therapeutic agent is typically administered orally, intranasally, intradermally, subcutaneously, intramuscularly, topically or intravenously. In some methods, the patient is monitored followed administration to assess the immune response. If the monitoring indicates a reduction of the immune response over time, the patient can be given one or more further doses of the agent.

In another aspect, the invention provides pharmaceutical compositions comprising Aβ and an excipient suitable for oral and other routes of administration. The invention also provides pharmaceutical compositions comprising an agent effective to induce an immunogenic response against Aβ in a patient, and a pharmaceutically acceptable adjuvant. In some such compositions, the agent is Aβ or an active fragment thereof. In some compositions, the adjuvant comprises alum. In some compositions, the adjuvant comprises an oil-in-water emulsion. In some compositions, the Aβ or active fragment is a component of a polylactide polyglycolide copolymer (PLPG) or other particle. The invention further provides compositions comprising Aβ or an active fragment linked to a conjugate molecule that promotes delivery of Aβ to the bloodstream of a patient and/or promotes an immune response against Aβ. For example, the conjugate can serve to promote an immune response against Aβ. In some compositions, the conjugate is cholera toxin. In some compositions, the conjugate is an immunoglobulin. In some compositions, the conjugate is attenuated diphtheria toxin CRM 197 (Gupta, *Vaccine* 15, 1341–3 (1997).

The invention also provides pharmaceutical compositions comprising an agent effect to induce an immunogenic response against Aβ in a patient with the proviso that the composition is free of Complete Freund's adjuvant. The invention also provides compositions comprising a viral vector encoding Aβ or a an active fragment thereof effective to induce an immune response against Aβ. Suitable viral vectors include herpes, adenovirus, adenoassociated virus, a retrovirus, sindbis, semiliki forest virus, vaccinia or avian pox.

The invention further provides methods of preventing or treating Alzheimer's disease. In such methods, an effective dose of Aβ peptide is administered to a patient. The invention further provides for the use of Aβ, or an antibody thereto, in the manufacture of a medicament for prevention or treatment of Alzheimer's disease.

In another aspect, the invention provides methods of assessing efficacy of an Alzheimer's treatment method in a patient. In these methods, a baseline amount of antibody specific for Aβ peptide is determined in a tissue sample from the patient before treatment with an agent. An amount of antibody specific for Aβ peptide in the tissue sample from the patient after treatment with the agent is compared to the baseline amount of Aβ peptide-specific antibody. An amount of Aβ peptide-specific antibody measured after the treatment that is significantly greater than the baseline amount of Aβ peptide-specific antibody indicates a positive treatment outcome.

In others methods of assessing efficacy of an Alzheimer's treatment method in a patient, a baseline amount of antibody specific for Aβ peptide in a tissue sample from a patient before treatment with an agent is determined. An amount of antibody specific for Aβ peptide in the tissue sample from the subject after treatment with the agent is compared to the baseline amount of Aβ peptide-specific antibody. A reduction or lack of significant difference between the amount of Aβ peptide-specific antibody measured after the treatment compared to the baseline amount of Aβ peptide-specific antibody indicates a negative treatment outcome.

In other methods of assessing efficacy of an Alzheimer's disease treatment method in a patient a control amount of antibody specific for Aβ peptide is determined in tissue samples from a control population. An amount of antibody specific for Aβ peptide in a tissue sample from the patient after administering an agent is compared to the control amount of Aβ peptide-specific antibody. An amount of Aβ peptide-specific antibody measured after the treatment that is significantly greater than the control amount of Aβ peptide-specific antibody indicates a positive treatment outcome.

In other methods of assessing efficacy of an Alzheimer's treatment method in a patient, a control amount of antibody specific for Aβ peptide in tissues samples from a control population is determined. An amount of antibody specific for Aβ peptide in a tissue sample from the patient after administering an agent is compared to the control amount of Aβ peptide-specific antibody. A lack of significant difference between the amount of Aβ peptide-specific antibody measured after beginning said treatment compared to the control amount of Aβ peptide-specific antibody indicates a negative treatment outcome.

Other methods of monitoring Alzheimer's disease or susceptibility thereto in a patient, comprise detecting an immune response against Aβ peptide in a sample from the patient. In some such methods, the patient is being administered an agent effective to treat or prevent Alzheimer's disease, and the level of the response determines the future treatment regime of the patient.

In other methods of assessing efficacy of an Alzheimer's treatment method in a patient a value for an amount of antibody specific for Aβ peptide in tissue sample from a patient who has been treated with an agent is determined. The value is compared with a control value determined from a population of patient experiencing amelioriation of, or freedom from, symptoms of Alzheimer's disease due to treatment with the agent. A value in the patient at least equal to the control value indicates a positive response to treatment.

The invention further provides diagnostic kits for performing the above methods. Such kits typically include a reagent that specifically binds to antibodies to Aβ or which stimulates proliferation of T-cells reactive with Aβ.

BRIEF DESCRIPTION OF THE FIGURES

FIGS. 15A–E: Aβ levels in the cortex of 12-month old PDAPP mice treated with AN1792 or AN1528 in combination with different adjuvants. The Aβ level for individual mice in each treatment group, and the median, mean, and p values for each treatment group are shown.

FIG. 15A: The values for mice in the PBS-treated control group and the untreated control group.

FIG. 15B: The values for mice in the AN1528/alum and AN1528/MPL-treatment groups.

FIG. 15C: The values for mice in the AN1528/QS21 and AN1792/Freund's adjuvant treatment groups.

FIG. 15D: The values for mice in the AN1792/Thimerosol and AN1792/alum treatment groups.

FIG. 15E: The values for mice in the AN1792/MPL and AN1792/QS21 treatment groups.

DETAILED DESCRIPTION

I. General

Figure 1:
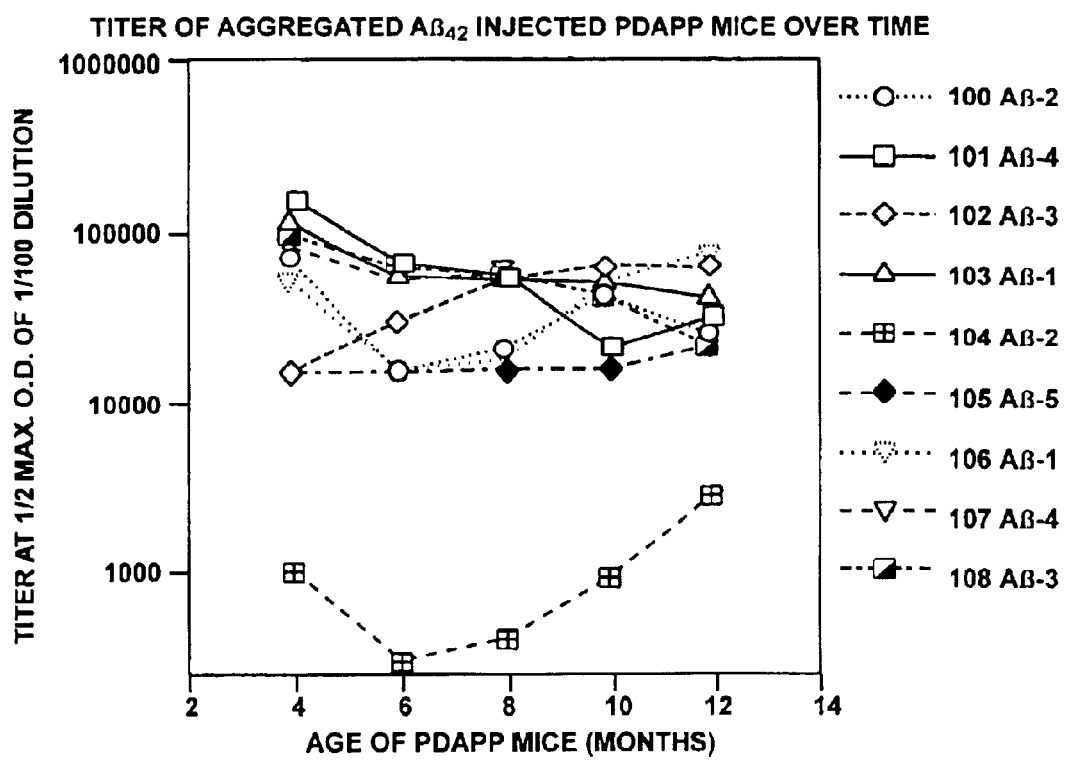
FIG. 1: Antibody titer after injection of transgenic mice with Aβ1-42.

The invention provides pharmaceutical compositions and methods for prophylactic and therapeutic treatment of diseases characterized by accumulation of amyloid deposits. Amyloid deposits comprise a peptide aggregated to an insoluble mass. The nature of the peptide varies in different diseases but in most cases, the aggregate has a β-pleated sheet structure and stains with Congo Red dye. Diseases characterized by amyloid deposits include Alzheimer's disease (AD), both late and early onset. In both diseases, the amyloid deposit comprises a peptide termed Aβ, which accumulates in the brain of affected individuals. Examples of some other diseases characterized by amyloid deposits are SAA amyloidosis, hereditary Icelandic syndrome, multiple myeloma, and spongiform encephalopathies, including mad cow disease, Creutzfeldt Jakob disease, sheep scrapie, and mink spongiform encephalopathy (see Weissmann et al., *Curr. Opin. Neurobiol.* 7, 695–700 (1997); Smits et al., Veterinary Quarterly 19, 101–105 (1997); Nathanson et al., Am. J. Epidemiol. 145, 959–969 (1997)). The peptides forming the aggregates in these diseases are serum amyloid A, cystantin C, IgG kappa light chain respectively for the first three, and prion protein for the others.

II. Definitions

The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions which are not identical differ by conservative amino acid substitutions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci.* USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). One example of algorithm that is suitable for determining percent sequence identify and sequence similarity is the BLAST algorithm, which is described in Altschul et al., J. Mol. Biol. 215:403–410 (1990). Software for performing BLAST analyses is publicly available through the National Center or Biotechnology Information (http://www.ncbi.nlm.nih.gov/). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff&Henikoff, Proc. Natl. Acad. Sci. USA 89, 10915(1989)).

For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Therapeutic agents of the invention are typically substantially pure. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% w/w can be obtained.

Specific binding between two entities means an affinity of at least $10^6$, $10^7$, $10^8$, $10^9$ M$^{-1}$, or $10^{10}$ M$^{-1}$. Affinities greater than $10^8$ M$^{-1}$ are preferred.

The term "antibody" is used to include intact antibodies and binding fragments thereof. Typically, fragments compete with the intact antibody from which they were derived for specific binding to an antigen. Optionally, antibodies or binding fragments thereof, can be chemically conjugated to, or expressed as, fusion proteins with other proteins.

APP$^{695}$, APP$^{751}$, and APP$^{770}$ refer, respectively, to the 695, 751, and 770 amino acid residue long polypeptides encoded by the human APP gene. See Kang et al., Nature 325, 773 (1987); Ponte et al., Nature 331, 525 (1988); and Kitaguchi et al., Nature 331, 530 (1988). Amino acids within the human amyloid precursor protein (APP) are assigned numbers according to the sequence of the APP770 isoform. Terms such as Aβ39, Aβ40, Aβ41, Aβ42 and Aβ43 refer to an Aβ peptide containing amino acid residues 1-39, 1-40, 1-41, 1-42 and 1-43.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8–10 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13–15 amino acids for CD4 cells. T cells that recognize the epitope can be identified by in vitro assays that measure antigen-dependent proliferation, as determined by $^3$H-thymidine incorporation by primed T cells in response to an epitope (Burke et al., *J. Inf Dis.* 170, 1110–19 (1994)), by antigen-dependent killing (cytotoxic T lymphocyte assay, Tigges et al., *J. Immunol.* 156, 3901–3910) or by cytokine secretion.

The term "immunological" or "immune" response is the development of a beneficial humoral (antibody mediated) and/or a cellular (mediated by antigen-specific T cells or their secretion products) response directed against an amyloid peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4$^+$ T helper cells and/or CD8$^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays (CD4$^+$ T cells) or CTL (cytotoxic T lymphocyte) assays (see Burke, supra; Tigges, supra). The relative contributions of humoral and cellular responses to the protective or therapeutic effect of an immunogen can be distinguished by separately isolating IgG and T-cells from an immunized syngeneic animal and measuring protective or therapeutic effect in a second subject.

An "immunogenic agent" or "immunogen" is capable of inducing an immunological response against itself on administration to a patient, optionally in conjunction with an adjuvant.

The term "naked polynucleotide" refers to a polynucleotide not complexed with colloidal materials. Naked polynucleotides are sometimes cloned in a plasmid vector.

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

The term "patient" includes human and other mammalian subjects that receive either prophylactic or therapeutic treatment.

Disaggregated or monomeric Aβ means soluble, monomeric peptide units of Aβ. One method to prepare monomeric Aβ is to dissolve lyophilized peptide in neat DMSO with sonication. The resulting solution is centrifuged to remove any nonsoluble particulates. Aggregated Aβ is a mixture of oligomers in which the monomeric units are held together by noncovalent bonds.

Compositions or methods "comprising" one or more recited elements may include other elements not specifically recited. For example, a composition that comprises Aβ peptide encompasses both an isolated Aβ peptide and Aβ peptide as a component of a larger polypeptide sequence.

III. Therapeutic Agents

1. Alzheimer's Disease

Therapeutic agents for use in the present invention induce an immune response against Aβ peptide. These agents include Aβ peptide itself and variants thereof, analogs and mimetics of Aβ peptide that induce and/or crossreact with antibodies to Aβ peptide, and antibodies or T-cells reactive with Aβ peptide. Induction of an immune response can be active as when an immunogen is administered to induce antibodies or T-cells reactive with Aβ in a patient, or passive, as when an antibody is administered that itself binds to Aβ in patient.

Aβ, also known as β-amyloid peptide, or A4 peptide (see U.S. Pat. No. 4,666,829; Glenner & Wong, *Biochem. Biophys. Res. Commun.* 120, 1131 (1984)), is a peptide of 39–43 amino acids, which is the principal component of characteristic plaques of Alzheimer's disease. Aβ is generated by processing of a larger protein APP by two enzymes, termed β and γ secretases (see Hardy, TINS 20, 154 (1997)). Known mutations in APP associated with Alzheimer's disease occur proximate to the site of β or γ secretase, or within Aβ. For example, position 717 is proximate to the site of γ-secretase cleavage of APP in its processing to Aβ, and positions 670/671 are proximate to the site of β-secretase cleavage. It is believed that the mutations cause AD disease by interacting with the cleavage reactions by which Aβ is formed so as to increase the amount of the 42/43 amino acid form of Aβ generated.

Aβ has the unusual property that it can fix and activate both classical and alternate complement cascades. In particular, it binds to C1q and ultimately to C3bi. This association facilitates binding to macrophages leading to activation of B cells. In addition, C3bi breaks down further and then binds to CR2 on B cells in a T cell dependent manner leading to a 10,000 increase in activation of these cells. This mechanism causes Aβ to generate an immune response in excess of that of other antigens.

The therapeutic agent used in the claimed methods can be any of the naturally occurring forms of Aβ peptide, and particularly the human forms (i.e., Aβ39, Aβ40, Aβ41, Aβ or Aβ43). The sequences of these peptides and their relationship to the APP precursor are illustrated by FIG. 1 of Hardy et al., TINS 20, 155–158 (1997). For example, Aβ has the sequence:

```
                                           (SEQ ID NO:1)
H₂N-Asp-Ala-Glu-Phe-Arg-His-Asp-Ser-Gly-Tyr-Glu-

Val-His-His-Gln-Lys-Leu-Val-Phe-Phe-Ala-Glu-Asp-

Val-Gly-Ser-Asn-Lys-Gly-Ala-Ile-Ile-Gly-Leu-Met-

Val-Gly-Gly-Val-Val-Ile-Ala-OH.
```

Aβ41, Aβ40 and Aβ39 differ from Aβ42 by the omission of Ala, Ala-Ile, and Ala-Ile-Val respectively from the C-terminal end. Aβ43 differs from Aβ42 by the presence of a threonine residue at the C-terminus. The therapeutic agent can also be an active fragment or analog of a natural Aβ peptide that contains an epitope that induces a similar protective or therapeutic immune response on administration to a human. Immunogenic fragments typically have a sequence of at least 3, 5, 6, 10 or 20 contiguous amino acids from a natural peptide. Immunogenic fragments include Aβ1-5, 1-6, 1-12, 13-28, 17-28, 25-25, 35-40 and 35-42. Fragments from the N-terminal half of Aβ are preferred in some methods. Analogs include allelic, species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are α,α-disubstituted amino acids, N-alkyl amino acids, lactic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine. Fragments and analogs can be screened for prophylactic or therapeutic efficacy in transgenic animal models as described below.

Aβ, its fragments, analogs and other amyloidogenic peptides can be synthesized by solid phase peptide synthesis or recombinant expression, or can be obtained from natural sources. Automatic peptide synthesizers are commercially available from numerous suppliers, such as Applied Biosystems, Foster City, Calif. Recombinant expression can be in bacteria, such as E. coli, yeast, insect cells or mammalian cells. Procedures for recombinant expression are described by Sambrook et al., *Molecular Cloning: A Laboratory Manual* (C.S.H.P. Press, NY 2d ed., 1989). Some forms of Aβ peptide are also available commercially (e.g., American Peptides Company, Inc., Sunnyvale, Calif. and California Peptide Research, Inc. Napa, Calif.).

Therapeutic agents also include longer polypeptides that include, for example, an Aβ peptide, active fragment or analog together with other amino acids. For example, Aβ peptide can be present as intact APP protein or a segment thereof, such as the C-100 fragment that begins at the N-terminus of Aβ and continues to the end of APP. Such polypeptides can be screened for prophylactic or therapeutic efficacy in animal models as described below. The Aβ peptide, analog, active fragment or other polypeptide can be administered in associated form (i.e., as an amyloid peptide) or in dissociated form. Therapeutic agents also include multimers of monomeric immunogenic agents.

In a further variation, an immunogenic peptide, such as Aβ, can be presented as a viral or bacterial vaccine. A nucleic acid encoding the immunogenic peptide is incorporated into a genome or episome of the virus or bacteria. Optionally, the nucleic acid is incorporated in such a manner that the immunogenic peptide is expressed as a secreted protein or as a fusion protein with an outersurface protein of a virus or a transmembrane protein of a bacteria so that the peptide is displayed. Viruses or bacteria used in such methods should be nonpathogenic or attenuated. Suitable viruses include adenovirus, HSV, vaccinia and fowl pox. Fusion of an immunogenic peptide to HBsAg of HBV is particularly suitable. Therapeutic agents also include peptides and other compounds that do not necessarily have a significant amino acid sequence similarity with Aβ but nevertheless serve as mimetics of Aβ and induce a similar immune response. For example, any peptides and proteins forming β-pleated sheets can be screened for suitability. Anti-idiotypic antibodies against monoclonal antibodies to Aβ or other amyloidogenic peptides can also be used. Such anti-Id antibodies mimic the antigen and generate an immune response to it (see *Essential Immunology* (Roit ed., Blackwell Scientific Publications, Palo Alto, 6th ed.), p. 181).

Random libraries of peptides or other compounds can also be screened for suitability. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980.

Combinatorial libraries and other compounds are initially screened for suitability by determining their capacity to bind to antibodies or lymphocytes (B or T) known to be specific for Aβ or other amyloidogenic peptides. For example, initial screens can be performed with any polyclonal sera or monoclonal antibody to Aβ or other amyloidogenic peptide. Compounds identified by such screens are then further analyzed for capacity to induce antibodies or reactive lymphocytes to Aβ or other amyloidogenic peptide. For example, multiple dilutions of sera can be tested on microtiter plates that have been precoated with Aβ peptide and a standard ELISA can be performed to test for reactive antibodies to Aβ. Compounds can then be tested for prophylactic and therapeutic efficacy in transgenic animals predisposed to an amyloidogenic disease, as described in the Examples. Such animals include, for example, mice bearing a 717 mutation of APP described by Games et al., supra, and mice bearing a Swedish mutation of APP such as described by McConlogue et al., U.S. Pat. No. 5,612,486 and Hsiao et al., *Science* 274, 99 (1996); Staufenbiel et al., *Proc. Natl.*

Acad. Sci. USA 94, 13287–13292 (1997); Sturchler-Pierrat et al., Proc. Natl. Acad. Sci. USA 94, 13287–13292 (1997); Borchelt et al., Neuron 19, 939–945 (1997)). The same screening approach can be used on other potential agents such as fragments of Aβ, analogs of Aβ and longer peptides including Aβ, described above.

Therapeutic agents of the invention also include antibodies that specifically bind to Aβ. Such antibodies can be monoclonal or polyclonal. Some such antibodies bind specifically to the aggregated form of Aβ without binding to the dissociated form. Some bind specifically to the dissociated form without binding to the aggregated form. Some bind to both aggregated and dissociated forms. The production of non-human monoclonal antibodies, e.g., murine or rat, can be accomplished by, for example, immunizing the animal with Aβ. See Harlow & Lane, *Antibodies, A Laboratory Manual* (CSHP NY, 1988) (incorporated by reference for all purposes). Such an immunogen can be obtained from a natural source, by peptides synthesis or by recombinant expression.

Humanized forms of mouse antibodies can be generated by linking the CDR regions of non-human antibodies to human constant regions by recombinant DNA techniques. See Queen et al., *Proc. Natl. Acad. Sci. USA* 86, 10029–10033 (1989) and WO 90/07861 (incorporated by reference for all purposes).

Human antibodies can be obtained using phage-display methods. See, e.g., Dower et al., WO 91/17271; McCafferty et al., WO 92/01047. In these methods, libraries of phage are produced in which members display different antibodies on their outersurfaces. Antibodies are usually displayed as Fv or Fab fragments. Phage displaying antibodies with a desired specificity are selected by affinity enrichment to Aβ, or fragments thereof. Human antibodies against Aβ can also be produced from non-human transgenic mammals having transgenes encoding at least a segment of the human immunoglobulin locus and an inactivated endogenous immunoglobulin locus. See, e.g., Lonberg et al., WO93/12227 (1993); Kucherlapati, WO 91/10741 (1991) (each of which is incorporated by reference in its entirety for all purposes). Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using Aβ or other amyloid peptide as an affinity reagent.

Human or humanized antibodies can be designed to have IgG, IgD, IgA and IgE constant region, and any isotype, including IgG1, IgG2, IgG3 and IgG4. Antibodies can be expressed as tetramers containing two light and two heavy chains, as separate heavy chains, light chains, as Fab, Fab° F(ab')$_2$, and Fv, or as single chain antibodies in which heavy and light chain variable domains are linked through a spacer.

Therapeutic agents for use in the present methods also include T-cells that bind to Aβ peptide. For example, T-cells can be activated against Aβ peptide by expressing a human MHC class I gene and a human β-2-microglobulin gene from an insect cell line, whereby an empty complex is formed on the surface of the cells and can bind to Aβ peptide. T-cells contacted with the cell line become specifically activated against the peptide. See Peterson et al., U.S. Pat. No. 5,314,813. Insect cell lines expressing an MHC class II antigen can similarly be used to activate CD4 T cells.

2. Other Diseases

The same or analogous principles determine production of therapeutic agents for treatment of other amyloidogenic diseases. In general, the agents noted above for use in treatment of Alzheimer's disease can also be used for treatment early onset Alzheimer's disease associated with Down's syndrome. In mad cow disease, prion peptide, active fragments, and analogs, and antibodies to prion peptide are used in place of Aβ peptide, active fragments, analogs and antibodies to Aβ peptide in treatment of Alzheimer's disease. In treatment of multiple myeloma, IgG light chain and analogs and antibodies thereto are used, and so forth in other diseases.

3. Carrier Proteins

Some agents for inducing an immune response contain the appropriate epitope for inducing an immune response against amyloid deposits but are too small to be immunogenic. In this situation, a peptide immunogen can be linked to a suitable carrier to help elicit an immune response. Suitable carriers include serum albumins, keyhole limpet hemocyanin, immunoglobulin molecules, thyroglobulin, ovalbumin, tetanus toxoid, or a toxoid from other pathogenic bacteria, such as diphtheria, *E. coli*, cholera, or *H. pylori*, or an attenuated toxin derivative. Other carriers for stimulating or enhancing an immune response include cytokines such as IL-1, IL-1 α and β peptides, IL-2, γINF, IL-10, GM-CSF, and chemokines, such as M1P1α and β and RANTES. Immunogenic agents can also be linked to peptides that enhance transport across tissues, as described in O'Mahony, WO 97/17613 and WO 97/17614.

Immunogenic agents can be linked to carriers by chemical crosslinking. Techniques for linking an immunogen to a carrier include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the ε-amino on a lysine, or other free amino group in other amino acids. A variety of such disulfide/amide-forming agents are described by *Immun. Rev.* 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimidomethyl)cyclohexane-1-carboxylic acid. The carboxyl groups can be activated by combining them with succinimide or 1-hydroxyl-2-nitro-4-sulfonic acid, sodium salt.

Immunogenic peptides can also be expressed as fusion proteins with carriers. The immunogenic peptide can be linked at the amino terminus, the carboxyl terminus, or internally to the carrier. Optionally, multiple repeats of the immunogenic peptide can be present in the fusion protein.

4. Nucleic Acid Encoding Immunogens

Immune responses against amyloid deposits can also be induced by administration of nucleic acids encoding Aβ peptide or other peptide immunogens. Such nucleic acids can be DNA or RNA. A nucleic acid segment encoding the immunogen is typically linked to regulatory elements, such as a promoter and enhancer, that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector.

A number of viral vector systems are available including retroviral systems (see, e.g., Lawrie and Tumin, *Cur. Opin. Genet. Develop.* 3, 102–109 (1993)); adenoviral vectors (see, e.g., Bett et al., *J. Virol.* 67, 5911 (1993)); adeno-associated virus vectors (see, e.g., Zhou et al., *J. Exp. Med* 179, 1867 (1994)), viral vectors from the pox family including vaccinia virus and the avian pox viruses, viral vectors from the alpha virus genus such as those derived from Sindbis and Semliki Forest Viruses (see, e.g., Dubensky et al., *J. Virol.* 70, 508–519 (1996)), and papillomaviruses (Ohe et al., *Human Gene Therapy* 6, 325–333 (1995); Woo et al., WO 94/12629 and Xiao & Brandsma, *Nucleic Acids. Res.* 24, 2630–2622 (1996)).

DNA encoding an immunogen, or a vector containing the same, can be packaged into liposomes. Suitable lipids and related analogs are described by U.S. Pat. Nos. 5,208,036, 5,264,618, 5,279,833 and 5,283,185. Vectors and DNA encoding an immunogen can also be adsorbed to or associated with particulate carriers, examples of which include polymethyl methacrylate polymers and polylactides and poly(lactide-co-glycolides), see, e.g., McGee et al., *J. Micro Encap.* (1996).

Gene therapy vectors or naked DNA can be delivered in vivo by administration to an individual patient, typically by systemic administration (e.g., intravenous, intraperitoneal, nasal, gastric, intradermal, intramuscular, subdermal, or intracranial infusion) or topical application (see e.g., U.S. Pat. No. 5,399,346). DNA can also be administered using a gene gun. See Xiao & Brandsma, supra. The DNA encoding an immunogen is precipitated onto the surface of microscopic metal beads. The microprojectiles are accelerated with a shock wave or expanding helium gas, and penetrate tissues to a depth of several cell layers. For example, The Accel™ Gene Delivery Device manufactured by Agacetus, Inc. Middleton, Wis. is suitable. Alternatively, naked DNA can pass through skin into the blood stream simply by spotting the DNA onto skin with chemical or mechanical irritation (see WO 95/05853).

In a further variation, vectors encoding immunogens can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

IV. Patients Amenable to Treatment

Patients amenable to treatment include individuals at risk of disease but not showing symptoms, as well as patients presently showing symptoms. In the case of Alzheimer's disease, virtually anyone is at risk of suffering from Alzheimer's disease if he or she lives long enough. Therefore, the present methods can be administered prophylactically to the general population without any assessment of the risk of the subject patient. The present methods are especially useful for individuals who do have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of AD, hypercholesterolemia or atherosclerosis.

Individuals presently suffering from Alzheimer's disease can be recognized from characteristic dementia, as well as the presence of risk factors described above. In addition, a number of diagnostic tests are available for identifying individuals who have AD. These include measurement of CSF tau and A$\beta$42 levels. Elevated tau and decreased A$\beta$42 levels signify the presence of AD. Individuals suffering from Alzheimer's disease can also be diagnosed by MMSE or ADRDA criteria as discussed in the Examples section.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody, or activated T-cell or B-cell responses to the therapeutic agent (e.g., A$\beta$ peptide) over time. If the response falls, a booster dosage is indicated. In the case of potential Down's syndrome patients, treatment can begin antenatally by administering therapeutic agent to the mother or shortly after birth.

V. Treatment Regimes

In prophylactic applications, pharmaceutical compositions or medicants are administered to a patient susceptible to, or otherwise at risk of, a particular disease in an amount sufficient to eliminate or reduce the risk or delay the outset of the disease. In therapeutic applications, compositions or medicants are administered to a patient suspected of, or already suffering from such a disease in an amount sufficient to cure, or at least partially arrest, the symptoms of the disease and its complications. An amount adequate to accomplish this is defined as a therapeutically- or pharmaceutically-effective dose. In both prophylactic and therapeutic regimes, agents are usually administered in several dosages until a sufficient immune response has been achieved. Typically, the immune response is monitored and repeated dosages are given if the immune response starts to fade.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human, but in some diseases, such as mad cow disease, the patient can be a nonhuman mammal, such as a bovine. Treatment dosages need to be titrated to optimize safety and efficacy. The amount of immunogen depends on whether adjuvant is also administered, with higher dosages being required in the absence of adjuvant. The amount of an immunogen for administration sometimes varies from 1 $\mu$g–500 $\mu$g per patient and more usually from 5–500 $\mu$g per injection for human administration. Occasionally, a higher dose of 1–2 mg per injection is used. Typically about 10, 20, 50 or 100 $\mu$g is used for each human injection. The timing of injections can vary significantly from once a day, to once a year, to once a decade. On any given day that a dosage of immunogen is given, the dosage is greater than 1 $\mu$g/patient and usually greater than 10 $\mu$g/patient if adjuvant is also administered, and greater than 10 $\mu$g/patient and usually greater than 100 $\mu$g/patient in the absence of adjuvant. A typical regimen consists of an immunization followed by booster injections at 6 weekly intervals. Another regimen consists of an immunization followed by booster injections 1, 2 and 12 months later. Another regimen entails an injection every two months for life. Alternatively, booster injections can be on an irregular basis as indicated by monitoring of immune response. For passive immunization with an antibody, the dosage ranges from about 0.0001 to 100 mg/kg, and more usually 0.01 to 5 mg/kg of the host body weight. Doses for nucleic acids encoding immunogens range from about 10 ng to 1 g, 100 ng to 100 mg, 1 μg to 10 mg, or 30–300 μg DNA per patient. Doses for infectious viral vectors vary from $10-10^9$, or more, virions per dose.

Agents for inducing an immune response can be administered by parenteral, topical, intravenous, oral, subcutaneous, intraperitoneal, intranasal or intramuscular means for prophylactic and/or therapeutic treatment. The most typical route of administration is subcutaneous although others can be equally effective. The next most common is intramuscular injection. This type of injection is most typically performed in the arm or leg muscles. Intravenous injections as well as intraperitoneal injections, intraarterial, intracranial, or intradermal injections are also effective in generating an immune response. In some methods, agents are injected directly into a particular tissue where deposits have accumulated.

Agents of the invention can optionally be administered in combination with other agents that are at least partly effective in treatment of amyloidogenic disease. In the case of Alzheimer's and Down's syndrome, in which amyloid deposits occur in the brain, agents of the invention can also be administered in conjunction with other agents that increase passage of the agents of the invention across the blood-brain barrier.

Immunogenic agents of the invention, such as peptides, are sometimes administered in combination with an adjuvant. A variety of adjuvants can be used in combination with a peptide, such as Aβ, to elicit an immune response. Preferred adjuvants augment the intrinsic response to an immunogen without causing conformational changes in the immunogen that affect the qualitative form of the response. Preferred adjuvants include alum, 3 De-O-acylated monophosphoryl lipid A (MPL) (see GB 2220211). QS21 is a triterpene glycoside or saponin isolated from the bark of the *Quillaja Saponaria* Molina tree found in South America (see Kensil et al., in *Vaccine Design: The Subunit and Ajuvant Approach* (eds. Powell & Newman, Plenum Press, NY, 1995); U.S. Pat. No. 5,057,540). Other adjuvants are oil in water emulsions (such as squalene or peanut oil), optionally in combination with immune stimulants, such as monophosphoryl lipid A (see Stoute et al., *N. Engl. J. Med.* 336, 86–91 (1997)). Another adjuvant is CpG (*Bioworld Today*, Nov. 15, 1998). Alternatively, Aβ can be coupled to an adjuvant. For example, a lipopeptide version of Aβ can be prepared by coupling palmitic acid or other lipids directly to the N-terminus of Aβ as described for hepatitis B antigen vaccination (Livingston, *J. Immunol.* 159, 1383–1392 (1997)). However, such coupling should not substantially change the conformation of Aβ so as to affect the nature of the immune response thereto. Adjuvants can be administered as a component of a therapeutic composition with an active agent or can be administered separately, before, concurrently with, or after administration of the therapeutic agent.

A preferred class of adjuvants is aluminum salts (alum), such as aluminum hydroxide, aluminum phosphate, aluminum sulfate. Such adjuvants can be used with or without other specific immunostimulating agents such as MPL or 3-DMP, QS21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalane, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi Immunochem, Hamilton, Mont.) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™). Another class of preferred adjuvants is saponin adjuvants, such as Stimulon™ (QS21, Aquila, Worcester, Mass.) or particles generated therefrom such as ISCOMs (immunostimulating complexes) and ISCOMATRIX. Other adjuvants include Complete Freund's Adjuvant (CFA) and Incomplete Freund's Adjuvant (IFA). Other adjuvants include cytokines, such as interleukins (IL-1,IL-2, and IL-12), macrophage colony stimulating factor (M-CSF), tumor necrosis factor (TNF).

An adjuvant can be administered with an immunogen as a single composition, or can be administered before, concurrent with or after administration of the immunogen. Immunogen and adjuvant can be packaged and supplied in the same vial or can be packaged in separate vials and mixed before use immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the vaccine containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS21 are preferred. Optionally, two or more different adjuvants can be used simultaneously. Preferred combinations include alum with MPL, alum with QS21, MPL with QS21, and alum, QS21 and MPL together. Also, Incomplete Freund's ajuvant can be used (Chang et al., *Advanced Drug Delivery Reviews* 32, 173–186 (1998)), optionally in combination with any of alum, QS21, and MPL and all combinations thereof.

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. However, some reagents suitable for administration to animals, such as Complete Freund's adjuvant are not typically included in compositions for human use.

Pharmaceutical compositions can also include large, slowly metabolized macromolecules such as proteins, polysaccharides, polylactic acids, polyglycolic acids and copolymers (such as latex functionalized sepharose, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier which can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249, 1527 (1990) and Hanes, *Advanced Drug Delivery Reviews* 28, 97–119 (1997). The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%–2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%–95% of active ingredient, preferably 25%–70%.

Topical application can result in transdermal or intradermal delivery. Topical administration can be facilitated by co-administration of the agent with cholera toxin or detoxified derivatives or subunits thereof or other similar bacterial toxins (See Glenn et al., *Nature* 391, 851 (1998)). Co-administration can be achieved by using the components as a mixture or as linked molecules obtained by chemical crosslinking or expression as a fusion protein.

Alternatively, transdermal delivery can be achieved using a skin path or using transferosomes (Paul et al., *Eur. J. Immunol.* 25, 3521–24 (1995); Cevc et al., *Biochem. Biophys. Acta* 1368, 201–15 (1998)).

VI. Methods of Diagnosis

The invention provides methods of detecting an immune response against Aβ peptide in a patient suffering from or susceptible to Alzheimer's disease. The methods are particularly useful for monitoring a course of treatment being administered to a patient. The methods can be used to monitor both therapeutic treatment on symptomatic patients and prophylactic treatment on asymptomatic patients.

Some methods entail determining a baseline value of an immune response in a patient before administering a dosage of agent, and comparing this with a value for the immune response after treatment. A significant increase (i.e., greater than the typical margin of experimental error in repeat measurements of the same sample, expressed as one standard deviation from the mean of such measurements) in value of the immune response signals a positive treatment outcome (i.e., that administration of the agent has achieved or augmented an immune response). If the value for immune response does not change significantly, or decreases, a negative treatment outcome is indicated. In general, patients undergoing an initial course of treatment with an agent are expected to show an increase in immune response with successive dosages, which eventually reaches the plateau. Administration of agent is generally continued while the immune response is increasing. Attainment of the plateau is an indicator that the administered of treatment can be discontinued or reduced in dosage or frequency.

In other methods, a control value (i.e., a mean and standard deviation) of immune response is determined for a control population. Typically the individuals in the control population have not received prior treatment. Measured values of immune response in a patient after administering a therapeutic agent are then compared with the control value. A significant increase relative to the control value (e.g., greater than one standard deviation from the mean) signals a positive treatment outcome. A lack of significant increase or a decrease signals a negative treatment outcome. Administration of agent is generally continued while the immune response is increasing relative to the control value. As before, attainment of a plateau relative to control values in an indicator that the administration of treatment can be discontinued or reduced in dosage or frequency.

In other methods, a control value of immune response (e.g., a mean and one standard deviation) is determined from a control population of individuals who have undergone treatment with a therapeutic agent and whose immune responses have plateaued in response to treatment. Measured values of immune response in a patient are compared with the control value. If the measured level in a patient is not significantly different (e.g., more than one standard deviation) from the control value, treatment can be discontinued. If the level in a patient is significantly below the control value, continued administration of agent is warranted. If the levels in the patient persist below the control value, then a change in treatment regime, for example, use of a different adjuvant may be indicated.

In other methods, a patient who is not presently receiving treatment but has undergone a previous course of treatment is monitored for immune response to determine whether a resumption of treatment is required. The measured value of immune response in the patient can be compared with a value of immune response previously achieved in the patient after a previous course of treatment. A significant decrease relative to the previous measurement (i.e., greater than a typical margin of error in repeat measurements of the same value) is an indication that treatment can be resumed. Alternatively, the value measured in patient can be compared with a control value (mean plus standard deviation) determined in population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (i.e., more than a standard deviation) is an indicator that treatment should be resumed in a patient.

The tissue sample for analysis is typically blood, plasma, serum, mucus or cerebral spinal fluid from the patient. The sample is analyzed for indicia of an immune response to any forms of Aβ peptide, typically Aβ42. The immune response can be determined from the presence of, e.g., antibodies or T-cells that specifically bind to Aβ peptide. ELISA methods of detecting antibodies specific to Aβ are described in the Examples section. Methods of detecting reactive T-cells have been described above (see Definitions).

The invention further provides diagnostic kits for performing the diagnostic methods described above. Typically, such kits contain an agent that specifically binds to antibodies to Aβ or reacts with T-cells specific for Aβ. The kit can also include a label. For detection of antibodies to Aβ, the label is typically in the form of labelled anti-idiotypic antibodies. For detection of antibodies, the agent can be supplied prebound to a solid phase, such as to the wells of a microtiter dish. For detection of reactive T-cells, the label can be supplied as $^3$H-thymidine to measure a proliferative response. Kits also typically contain labelling providing directions for use of the kit. The labelling may also include a chart or other correspondence regime correlating levels of measured label with levels of antibodies to Aβ or T-cells reactive with Aβ. The term labelling refers to any written or recorded material that is attached to, or otherwise accompanies a kit at any time during its manufacture, transport, sale or use. For example, the term labelling encompasses advertising leaflets and brochures, packaging materials, instructions, audio or video cassettes, computer discs, as well as writing imprinted directly on kits.

EXAMPLE I

Prophylactic Efficacy of Aβ Against AD

These examples describe administration of Aβ42 peptide to transgenic mice overexpressing APP with a mutation at position 717 (APP$_{717V \rightarrow F}$) that predisposes them to develop Alzheimer's-like neuropathology. Production and characteristics of these mice (PDAPP mice) is described in Games et al., *Nature*, supra. These animals, in their heterozygote form, begin to deposit Aβ at six months of age forward. By fifteen months of age they exhibit levels of Aβ deposition equivalent to that seen in Alzheimer's disease. PDAPP mice were injected with aggregated Aβ$_{42}$ (aggregated Aβ$_{42}$) or phosphate buffered saline. Aggregated Aβ$_{42}$ was chosen because of its ability to induce antibodies to multiple epitopes of Aβ.

A. Methods

1. Source of Mice

Thirty PDAPP heterogenic female mice were randomly divided into the following groups: 10 mice to be injected with aggregated Aβ$_{42}$ (one died in transit), 5 mice to be injected with PBS/adjuvant or PBS, and 10 uninjected controls. Five mice were injected with serum amyloid protein (SAP).

2. Preparation of Immunogens

Preparation of aggregated Aβ$_{42}$: two milligrams of Aβ$_{42}$ (US Peptides Inc, lot K-42-12) was dissolved in 0.9 ml water and made up to 1 ml by adding 0.1 ml 10×PBS. This was vortexed and allowed to incubate overnight 37° C., under which conditions the peptide aggregated. Any unused Aβ was stored as a dry lyophilized powder at −20° C. until the next injection.

3. Preparation of Injections

100 μg of aggregated Aβ$_{42}$ in PBS per mouse was emulsified 1:1 with Complete Freund's adjuvant (CFA) in a final volume of 400 μl emulsion for the first immunization, followed by a boost of the same amount of immunogen in Incomplete Freund's adjuvant (IFA) at 2 weeks. Two additional doses in IFA were given at monthly intervals. The subsequent immunizations were done at monthly intervals in 500 μl of PBS. Injections were delivered intraperitoneally (i.p.).

PBS injections followed the same schedule and mice were injected with a 1:1 mix of PBS/Adjuvant at 400 μl per mouse, or 500 μl of PBS per mouse. SAP injections likewise followed the same schedule using a dose of 100 μg per injection.

4. Titration of Mouse Bleeds, Tissue Preparation and Immunohistochemistry

B. Results

PDAPP mice were injected with either aggregated Aβ$_{42}$ (aggregated Aβ$_{42}$), SAP peptides, or phosphate buffered saline. A group of PDAPP mice were also left as uninjected, positive controls. The titers of the mice to aggregated Aβ$_{42}$ were monitored every other month from the fourth boost until the mice were one year of age. Mice were sacrificed at 13 months. At all time points examined, eight of the nine aggregated Aβ$_{42}$ mice developed a high antibody titer, which remained high throughout the series of injections (titers greater than 1/10000). The ninth mouse had a low, but measurable titer of approximately 1/1000 (FIG. 1, Table 1). SAPP-injected mice had titers of 1:1,000 to 1:30,000 for this immunogen with only a single mice exceeding 1:10,0000.

The PBS-treated mice were titered against aggregated Aβ4$_2$ at six, ten and twelve months. At a 1/100 dilution the PBS mice when titered against aggregated Aβ$_{42}$ only exceeded 4 times background at one data point, otherwise, they were less than 4 times background at all time points (Table 1). The SAP-specific response was negligible at these time points with all titers less than 300.

Seven out of the nine mice in the aggregated Aβ1-42 group had no detectable amyloid in their brains. In contrast, brain tissue from mice in the SAP and PBS groups contained numerous 3D6-positive amyloid deposits in the hippocampus, as well as in the frontal and cingulate cortices. The pattern of deposition was similar to that of untreated controls, with characteristic involvement of vulnerable subregions, such as the outer molecular layer of the hippocampal dentate gyrus. One mouse from the Aβ 1-42-injected group had a greatly reduced amyloid burden, confined to the hippocampus. An isolated plaque was identified in another Aβ 1-42-treated mouse.

Figure 2:
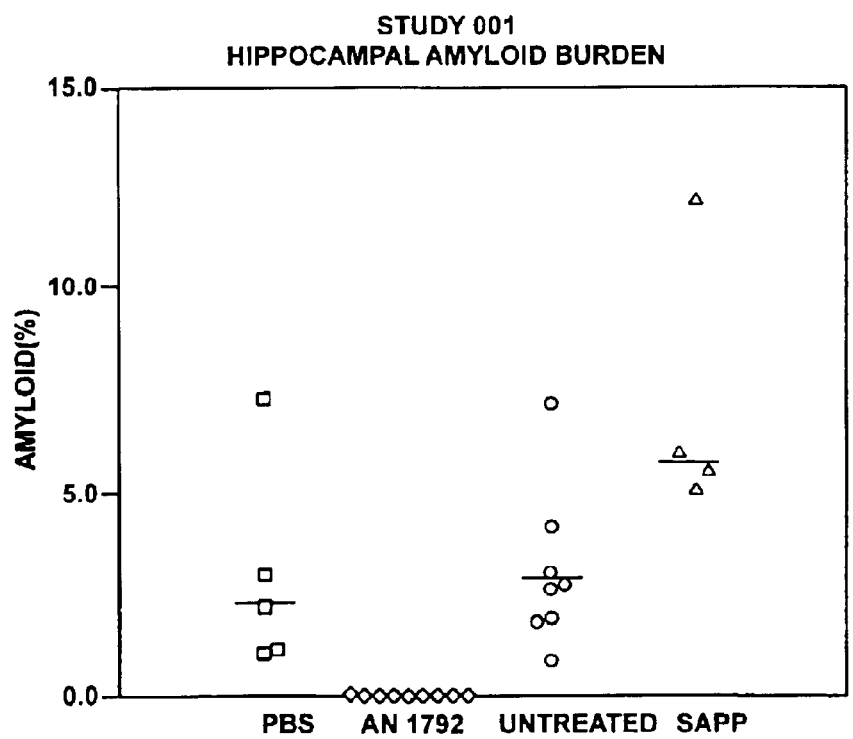
FIG. 2: Amyloid burden in the hippocampus. The percentage of the area of the hippocampal region occupied by amyloid plaques, defined by reactivity with the Aβ-specific mAβ 3D6, was determined by computer-assisted quantitative image analysis of immunoreacted brain sections. The values for individual mice are shown sorted by treatment group. The horizontal line for each grouping indicates the median value of the distribution.

Quantitative image analyses of the amyloid burden in the hippocampus verified the dramatic reduction achieved in the AN1792-treated animals (FIG. 2). The median values of the amyloid burden for the PBS group (2.22%), and for the untreated control group (2.65%) were significantly greater than for those immunized with AN1792 (0.00%, p=0.0005). In contrast, the median value for the group immunized with SAP peptides (SAPP) was 5.74%. Brain tissue from the untreated, control mice contained numerous Aβ amyloid deposits visualized with the Aβ-specific monoclonal antibody (mAβ) 3D6 in the hippocampus, as well as in the retrosplenial cortex. A similar pattern of amyloid deposition was also seen in mice immunized with SAPP or PBS (FIG. 2). In addition, in these latter three groups there was a characteristic involvement of vulnerable subregions of the brain classically seen in AD, such as the outer molecular layer of the hippocampal dentate gyrus, in all three of these groups.

Figure 3:
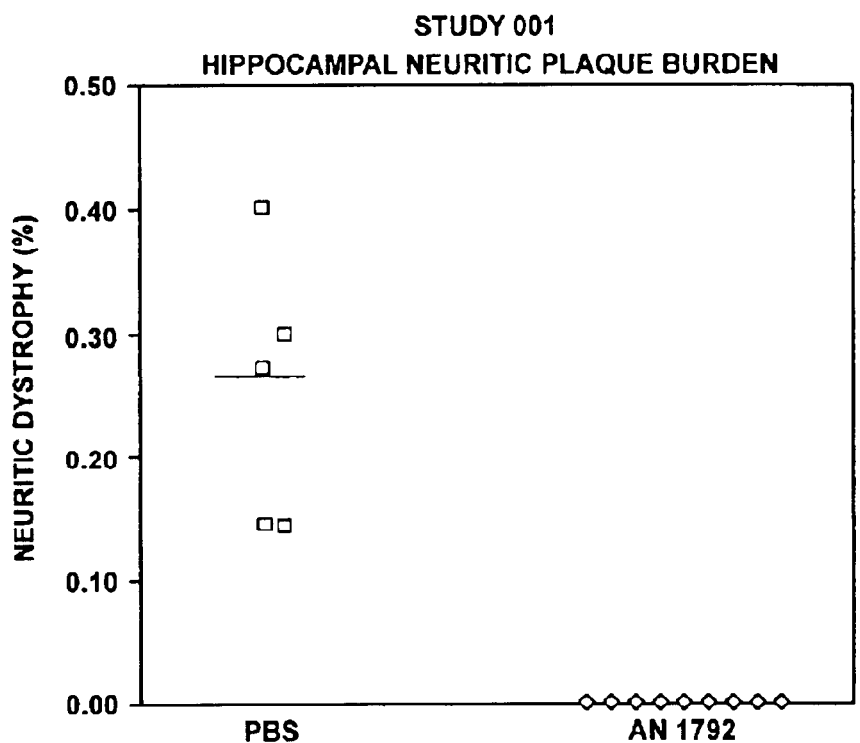
FIG. 3: Neuritic dystrophy in the hippocampus. The percentage of the area of the hippocampal region occupied by dystrophic neurites, defined by their reactivity with the human APP-specific mAβ 8E5, was determined by quantitative computer-assisted image analysis of immunoreacted brain sections. The values for individual mice are shown for the AN1792-treated group and the PBS-treated control group. The horizontal line for each grouping indicates the median value of the distribution.

The brains that contained no Aβ deposits were also devoid of neuritic plaques that are typically visualized in PDAPP mice with the human APP antibody 8E5. All of brains from the remaining groups (SAP-injected, PBS and uninjected mice) had numerous neuritic plaques typical of untreated PDAPP mice. A small number of neuritic plaques were present in one mouse treated with AN1792, and a single cluster of dystrophic neurites was found in a second mouse treated with AN1792. Image analyses of the hippocampus, and shown in FIG. 3, demonstrated the virtual elimination of dystrophic neurites in AN1792-treated mice (median 0.00%) compared to the PBS recipients (median 0.28%, p=0.0005).

Astrocytosis characteristic of plaque-associated inflammation was also absent in the brains of the Aβ1-42 injected group. The brains from the mice in the other groups contained abundant and clustered GFAP-positive astrocytes typical of Aβ plaque-associated gliosis. A subset of the GFAP-reacted slides were counter-stained with Thioflavin S to localize the Aβ deposits. The GFAP-positive astrocytes were associated with Aβ plaques in the SAP, PBS and untreated controls. No such association was found in the plaque-negative Aβ1-42 treated mice, while minimal plaque-associated gliosis was identified in one mouse treated with AN1792.

Figure 4:
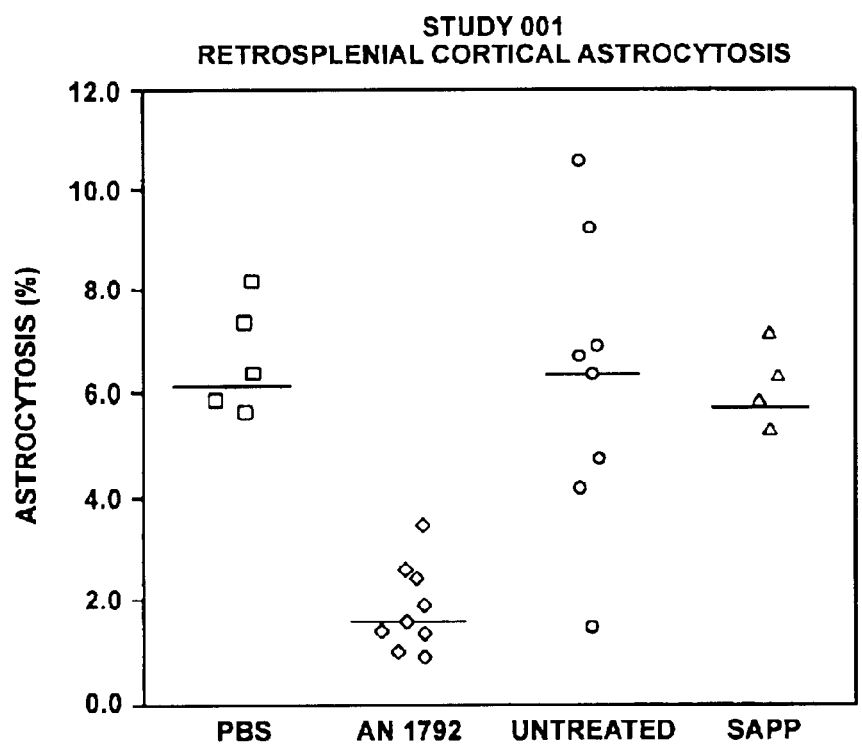
FIG. 4: Astrocytosis in the retrosplenial cortex. The percentage of the area of the cortical region occupied by glial fibrillary acidic protein (GFAP)-positive astrocytes was determined by quantitative computer-assisted image analysis of immunoreacted brain sections. The values for individual mice are shown sorted by treatment group and median group values are indicated by horizontal lines.

Image analyses, shown in FIG. 4 for the retrosplenial cortex, verified that the reduction in astrocytosis was significant with a median value of 1.56% for those treated with AN1792 versus median values greater than 6% for groups immunized with SAP peptides, PBS or untreated (p=0.0017).

Evidence from a subset of the Aβ 1-42- and PBS-injected mice indicated plaque-associated MHC II immunoreactivity was absent in the Aβ1-42 injected mice, consistent with lack of an Aβ-related inflammatory response.

Sections of the mouse brains were also reacted with a mAβ specific for MAC-1, a cell surface protein. MAC-1 (CD11b) is an integrin family member and exists as a heterodimer with CD18. The CD11b/CD18 complex is present on monocytes, macrophages, neutrophils and natural killer cells (Mak and Simard). The resident MAC-1-reactive cell type in the brain is likely to be microglia based on similar phenotypic morphology in MAC-1 immunoreacted sections. Plaque-associated MAC-1 labeling was lower in the brains of mice treated with AN1792 compared to the PBS control group, a finding consistent with the lack of an Aβ-induced inflammatory response.

C. Conclusion

The lack of Aβ plaques and reactive neuronal and gliotic changes in the brains of the Aβ1-42-injected mice indicate that no or extremely little amyloid was deposited in their brains, and pathological consequences, such as gliosis and neuritic pathology, were absent. PDAPP mice treated with Aβ1-42 show essentially the same lack of pathology as control nontransgenic mice. Therefore, Aβ1-42 injections are highly effective in the prevention of deposition or clearance of human Aβ from brain tissue, and elimination of subsequent neuronal and inflammatory degenerative changes. Thus, administration of Aβ peptide has therapeutic benefit in prevention of AD.

Example II

Dose Response Study

Groups of five-week old, female Swiss Webster mice (N=6 per group) were immunized with 300, 100, 33, 11, 3.7, 1.2, 0.4, or 0.13 μg of Aβ formulated in CFA/IFA administered intraperitoneally. Three doses were given at biweekly intervals followed by a fourth dose one month later. The first dose was emulsified with CFA and the remaining doses were emulsified with IFA. Animals were bled 4–7 days following each immunization starting after the second dose for measurement of antibody titers. Animals in a subset of three groups, those immunized with 11, 33, or 300 μg of antigen, were additionally bled at approximately monthly intervals for four months following the fourth immunization to monitor the decay of the antibody response across a range of vaccine doses. These animals received a final fifth immunization at seven months after study initiation. They were sacrificed one week later to measure antibody responses to AN1792 and to perform toxicological analyses.

Figure 5:
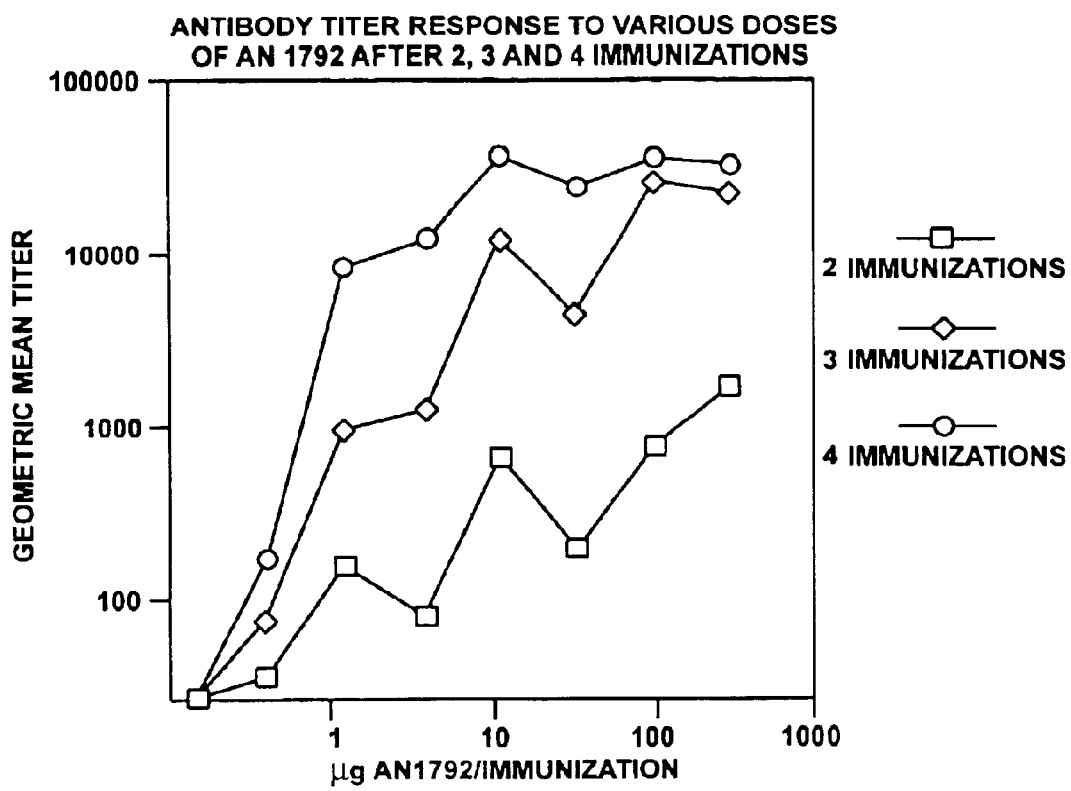
FIG. 5: Geometric mean antibody titers to Aβ1-42 following immunization with a range of eight doses of AN1792 containing 0.14, 0.4, 1.2, 3.7, 11, 33, 100, or 300 μg.

A declining dose response was observed from 300 to 3.7 μg with no response at the two lowest doses. Mean antibody titers are about 1:1000 after 3 doses and about 1:10,000 after 4 doses of 11–300 μg of antigen (see FIG. 5).

Antibody titers rose dramatically for all but the lowest dose group following the third immunization with increases in GMTs ranging from 5- to 25-fold. Low antibody responses were then detectable for even the 0.4 μg recipients. The 1.2 and 3.7 μg groups had comparable titers with GMTs of about 1000 and the highest four doses clustered together with GMTs of about 25,000, with the exception of the 33 μg dose group with a lower GMT of 3000. Following the fourth immunization, the titer increase was more modest for most groups. There was a clear dose response across the lower antigen dose groups from 0.14 μg to 11 μg ranging from no detectable antibody for recipients of 0.14 μg to a GMT of 36,000 for recipients of 11 μg. Again, titers for the four highest dose groups of 11 to 300 μg clustered together. Thus following two immunizations, the antibody titer was dependent on the antigen dose across the broad range from 0.4 to 300 μg. By the third immunization, titers of the highest four doses were all comparable and they remained at a plateau after an additional immunization.

Figure 6:
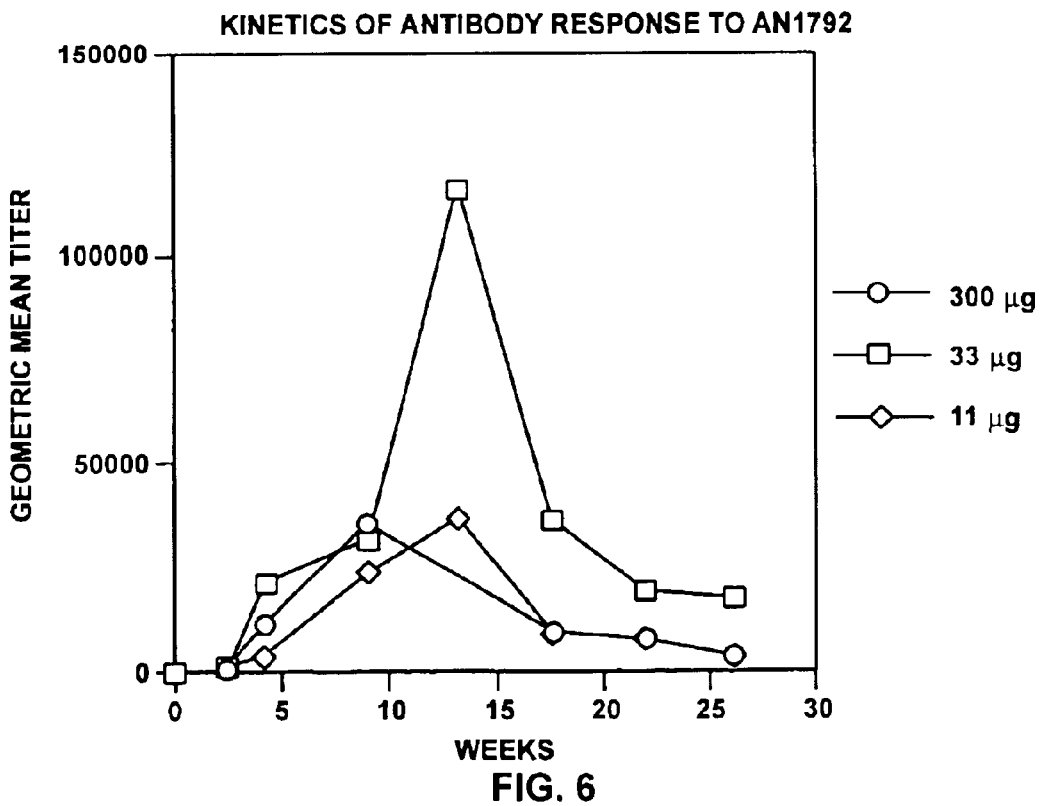
FIG. 6: Kinetics of antibody response to AN1792 immunization. Titers are expressed as geometric means of values for the 6 animals in each group.

One month following the fourth immunization, titers were 2- to 3-fold higher in the 300 μg group than those measured from blood drawn five days following the immunization (FIG. 6). This observation suggests that the peak anamnestic antibody response occurred later than 5 days post-immunization. A more modest (50%) increase was seen at this time in the 33 μg group. In the 300 μg dose group at two months following the last dose, GMTs declined steeply by about 70%. After another month, the decline was less steep at 45% (100 μg) and about 14% for the 33 and 11 μg doses. Thus, the rate of decline in circulating antibody titers following cessation of immunization appears to be biphasic with a steep decline the first month following peak response followed by a more modest rate of decrease thereafter.

The antibody titers and the kinetics of the response of these Swiss Webster mice are similar to those of young heterozygous PDAPP transgenic mice immunized in a parallel manner. Dosages effective to induce an immune response in humans are typically similar to dosages effective in mice.

Example III

Screen for Therapeutic Efficacy Against Established AD

This assay is designed to test immunogenic agents for activity in arresting or reversing neuropathological characteristics of AD in aged animals. Immunizations with 42 amino acid long Aβ (AN1792) were begun at a timepoint when amyloid plaques are already present in the brains of the PDAPP mice.

Over the timecourse used in this study, untreated PDAPP mice develop a number of neurodegenerative changes that resemble those found in AD (Games et al., supra and Johnson-Wood et al., Proc. Natl. Acad. Sci. USA 94, 1550–1555 (1997)). The deposition of Aβ into amyloid plaques is associated with a degenerative neuronal response consisting of aberrant axonal and dendritic elements, called dystrophic neurites. Amyloid deposits that are surrounded by and contain dystrophic neurites called neuritic plaques. In both AD and the PDAPP mouse, dystrophic neurites have a distinctive globular structure, are immunoreactive with a panel of antibodies recognizing APP and cytoskeletal components, and display complex subcellular degenerative changes at the ultrastructural level. These characteristics allow for disease-relevant, selective and reproducible measurements of neuritic plaque formation in the PDAPP brains. The dystrophic neuronal component of PDAPP neuritic plaques is easily visualized with an antibody specific for human APP (maAβ 8E5), and is readily measurable by computer-assisted image analysis. Therefore, in addition to measuring the effects of AN1792 on amyloid plaque formation, we monitored the effects of this treatment on the development of neuritic dystrophy.

Astrocytes and microglia are non-neuronal cells that respond to and reflect the degree of neuronal injury. GFAP-positive astrocytes and MHC II-positive microglia are commonly observed in AD, and their activation increases with the severity of the disease. Therefore, we also monitored the development of reactive astrocytosis and microgliosis in the AN1792-treated mice.

A. Materials and Methods

Forty-eight, heterozygous female PDAPP mice, 11 to 11.5 months of age, obtained from Charles River, were randomly divided into two groups: 24 mice to be immunized with 100 µg of AN1792 and 24 mice to be immunized with PBS, each combined with Freund's adjuvant. The AN1792 and PBS groups were again divided when they reached ~15 months of age. At 15 months of age approximately half of each group of the AN1792- and PBS-treated animals were euthanized (n=10 and 9, respectively), the remainder continued to receive immunizations until termination at ~18 months (n=9 and 12, respectively). A total of 8 animals (5 AN1792, 3 PBS) died during the study. In addition to the immunized animals, one-year old (n=10), 15-month old (n=10) and 18-month old (n=10) untreated PD APP mice were included for comparison in the ELISAs to measure Aβ and APP levels in the brain; the one-year old animals were also included in the immunohistochemical analyses.

Methodology was as in Example 1 unless otherwise indicated. US Peptides lot 12 and California Peptides lot ME0339 of AN1792 were used to prepare the antigen for the six immunizations administered prior to the 15-month timepoint. California Peptides lots ME0339 and ME0439 were used for the three additional immunizations administered between 15 and 18 months.

For immunizations, 100 µg of AN1792 in 200 µl PBS or PBS alone was emulsified 1:1 (vol:vol) with Complete Freund's adjuvant (CFA) or Incomplete Freund's adjuvant (IFA) or PBS in a final volume of 400 µl. The first immunization was delivered with CFA as adjuvant, the next four doses were given with IFA and the final four doses with PBS alone without added adjuvant. A total of nine immunizations were given over the seven-month period on a two-week schedule for the first three doses followed by a four-week interval for the remaining injections. The four-month treatment group, euthanized at 15 months of age, received only the first 6 immunizations.

B. Results

1. Effects of AN1792 Treatment on Amyloid Burden

Figure 7:
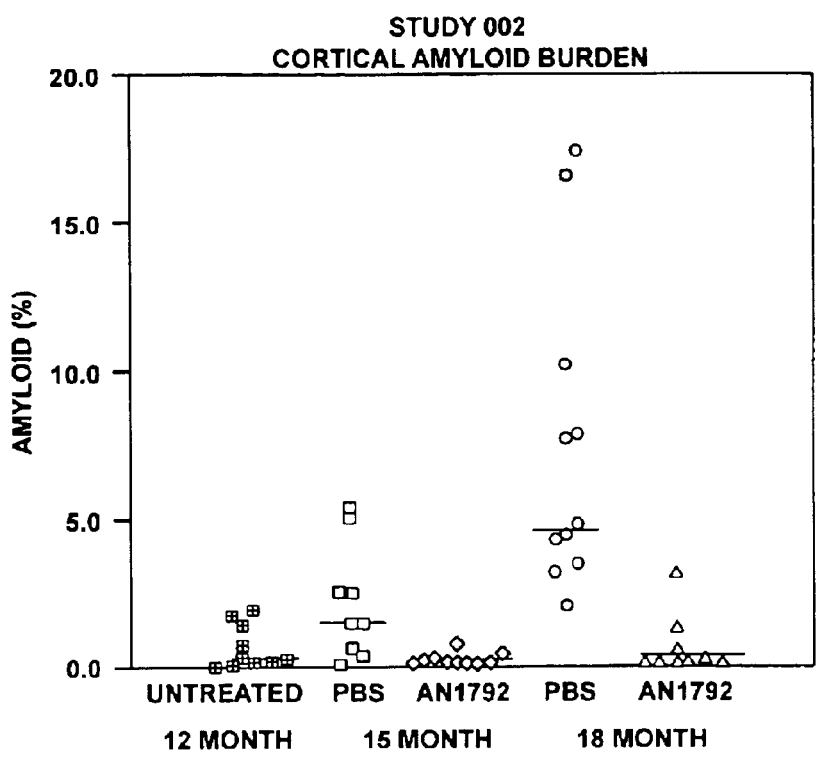
FIG. 7: Quantitative image analysis of the cortical amyloid burden in PBS- and AN1792-treated mice.

The results of AN1792 treatment on cortical amyloid burden determined by quantitative image analysis are shown in FIG. 7. The median value of cortical amyloid burden was 0.28% in a group of untreated 12-month old PDAPP mice, a value representative of the plaque load in mice at the study's initiation. At 18 months, the amyloid burden increased over 17-fold to 4.87% in PBS-treated mice, while AN1792-treated mice had a greatly reduced amyloid burden of only 0.01%, notably less than the 12-month untreated and both the 15- and 18-month PBS-treated groups. The amyloid burden was significantly reduced in the AN1792 recipients at both 15 (96% reduction; p=0.003) and 18 (>99% reduction; p=0.0002) months. Typically, cortical amyloid deposition in PDAPP mice initiates in the frontal and retrosplenial cortices (RSC) and progresses in a ventral-lateral direction to involve the temporal and entorhinal cortices (EC). Little or no amyloid was found in the EC of 12 month-old mice, the approximate age at which AN1792 was first administered. After 4 months of AN1792 treatment, amyloid deposition was greatly diminished in the RSC, and the progressive involvement of the EC was entirely eliminated by AN1792 treatment. The latter observation showed that AN1792 completely halted the progression of amyloid that would normally invade the temporal and ventral cortices, as well as arrested or possibly reversed deposition in the RSC.

The profound effects of AN1792 treatment on developing cortical amyloid burden in the PDAPP mice are further demonstrated by the 18-month group, which had been treated for seven months. A near complete absence of cortical amyloid was found in the AN1792-treated mouse, with a total lack of diffuse plaques, as well as a reduction in compacted deposits.

2. AN1792 Treatment-associated Cellular and Morphological Changes

A population of Aβ-positive cells was found in brain regions that typically contain amyloid deposits. Remarkably, in several brains from AN1792 recipients, very few or no extracellular cortical amyloid plaques were found. Most of the Aβ immunoreactivity appeared to be contained within cells with large lobular or clumped soma. Phenotypically, these cells resembled activated microglia or monocytes. They were immunoreactive with antibodies recognizing ligands expressed by activated monocytes and microglia (MHC II and CD11b) and were occasionally associated with the wall or lumen of blood vessels. Comparison of near-adjacent sections labeled with Aβ and MHC II-specific antibodies revealed that similar patterns of these cells were recognized by both classes of antibodies. Detailed examination of the AN1792-treated brains revealed that the MHC II-positive cells were restricted to the vicinity of the limited amyloid remaining in these animals. Under the fixation conditions employed, the cells were not immunoreactive with antibodies that recognize T cell (CD3, CD3e) or B cell (CD45RA, CD45RB) ligands or leukocyte common antigen (CD45), but were reactive with an antibody recognizing leukosialin (CD43) which cross-reacts with monocytes. No such cells were found in any of the PBS-treated mice.

PDAPP mice invariably develop heavy amyloid deposition in the outer molecular layer of the hippocampal dentate gyrus. The deposition forms a distinct streak within the perforant pathway, a subregion that classically contains amyloid plaques in AD. The characteristic appearance of these deposits in PBS-treated mice resembled that previously characterized in untreated PDAPP mice. The amyloid deposition consisted of both diffuse and compacted plaques in a continuous band. In contrast, in a number of brains from AN1792-treated mice this pattern was drastically altered. The hippocampal amyloid deposition no longer contained diffuse amyloid, and the banded pattern was completely disrupted. Instead, a number of unusual punctuate structures were present that are reactive with anti-Aβ antibodies, several of which appeared to be amyloid-containing cells.

MHC II-positive cells were frequently observed in the vicinity of extracellular amyloid in AN1792-treated animals. The pattern of association of Aβ-positive cells with amyloid was very similar in several brains from AN1792-treated mice. The distribution of these monocytic cells was restricted to the proximity of the deposited amyloid and was entirely absent from other brain regions devoid of Aβ plaques.

Quantitative image analysis of MHC II and MAC I-labeled sections revealed a trend towards increased immunoreactivity in the RSC and hippocampus of AN1792-treated mice compared to the PBS group which reached significance with the measure of MAC 1 reactivity in hippocampus.

These results are indicative of active, cell-mediated removal of amyloid in plaque-bearing brain regions.

3. AN1792 Effects on Aβ Levels: ELISA Determinations (a) Cortical Levels

In untreated PDAPP mice, the median level of total Aβ in the cortex at 12 months was 1,600 ng/g, which increased to 8,700 ng/g by 15 months (Table 2). At 18 months the value was 22,000 ng/g, an increase of over 10-fold during the time course of the experiment. PBS-treated animals had 8,600 ng/g total Aβ at 15 months which increased to 19,000 ng/g at 18 months. In contrast, AN1792-treated animals had 81% less total Aβ at 15 months (1,600 ng/g) than the PBS-immunized group. Significantly less (p=0.0001) total Aβ (5,200 ng/g) was found at 18 months when the AN1792 and PBS groups were compared (Table 2), representing a 72% reduction in the Aβ that would otherwise be present. Similar results were obtained when cortical levels of Aβ42 were compared, namely that the AN1792-treated group contained much less Aβ42, but in this case the differences between the AN1792 and PBS groups were significant at both 15 months (p=0.04) and 18 months (p=0.0001, Table 2).

TABLE 2

Median Aβ Levels (ng/g) in Cortex

| | UNTREATED | | | PBS | | | AN1792 | | |
|---|---|---|---|---|---|---|---|---|---|
| Age | Total Aβ | Aβ42 | (n) | Total Aβ | Aβ42 | (n) | Total Aβ | Aβ42 | (n) |
| 12 | 1,600 | 1,300 | (10) | | | | | | |
| 15 | 8,700 | 8,300 | (10) | 8,600 | 7,200 | (9) | 1,600 | 1,300* | (10) |
| 18 | 22,200 | 18,500 | (10) | 19,000 | 15,900 | (12) | 5,200** | 4,000** | (9) |

*p = 0.0412
**p = 0.0001

(b) Hippocampal Levels

In untreated PDAPP mice, median hippocampal levels of total Aβ at twelve months of age were 15,000 ng/g which increased to 51,000 ng/g at 15 months and further to 81,000 ng/g at 15 months (Table 3). Similarly, PBS immunized mice showed values of 40,000 ng/g and 65,000 ng/g at 15 months and 18 months, respectively. AN1792 immunized animals exhibited less total Aβ, specifically 25,000 ng/g and 51,000 ng/g at the respective 15-month and 18-month timepoints. The 18-month AN1792-treated group value was significantly lower than that of the PBS treated group (p=0.0105; Table 3). Measurement of Aβ42 gave the same pattern of results, namely that levels in the AN1792-treated group were significantly lower than in the PBS group (39,000 ng/g vs. 57,000 ng/g, respectively; p=0.0022) at the 18-month evaluation (Table 3).

TABLE 3

Median Aβ Levels (ng/g) in Hippocampus

| | UNTREATED | | | PBS | | | AN1792 | | |
|---|---|---|---|---|---|---|---|---|---|
| Age | Total Aβ | Aβ42 | (n) | Total Aβ | Aβ42 | (n) | Total Aβ | Aβ42 | (n) |
| 12 | 15,500 | 11,100 | (10) | | | | | | |
| 15 | 51,500 | 44,400 | (10) | 40,100 | 35,700 | (9) | 24,500 | 22,100 | (10) |
| 18 | 80,800 | 64,200 | (10) | 65,400 | 57,100 | (12) | 50,900* | 38,900** | (9) |

*p = 0.0105
**p = 0.0022

(c) Cerebellar Levels

In 12-month untreated PDAPP mice, the median cerebellar level of total Aβ was 15 ng/g (Table 4). At 15 months, this median increased to 28 ng/g and by 18 months had risen to 35 ng/g. PBS-treated animals displayed median total Aβ values of 21 ng/g at 15 months and 43 ng/g at 18 months. AN1792-treated animals were found to have 22 ng/g total Aβ at 15 months and significantly less (p=0.002) total Aβ at 18 months (25 ng/g) than the corresponding PBS group (Table 4).

TABLE 4

Median Aβ Levels (ng/g) in Cerebellum

| Age | UNTREATED | | PBS | | AN1792 | |
|---|---|---|---|---|---|---|
| | Total Aβ | (n) | Total Aβ | (n) | Total Aβ | (n) |
| 12 | 15.6 | (10) | | | | |
| 15 | 27.7 | (10) | 20.8 | (9) | 21.7 | (10) |
| 18 | 35.0 | (10) | 43.1 | (12) | 24.8* | (9) |

*p = 0.0018

4. Effects of AN1792 Treatment on APP Levels

APP-α and the full-length APP molecule both contain all or part of the Aβ sequence and thus could be potentially impacted by the generation of an AN1792-directed immune response. In studies to date, a slight increase in APP levels has been noted as neuropathology increases in the PDAPP mouse. In the cortex, levels of either APP-α/FL (full length) or APP-α were essentially unchanged by treatment with the exception that APP-α was reduced by 19% at the 18-month timepoint in the AN1792-treated vs. the PBS-treated group. The 18-month AN1792-treated APP values were not significantly different from values of the 12-month and 15-month untreated and 15-month PBS groups. In all cases the APP values remained within the ranges that are normally found in PDAPP mice.

5. Effects of AN1792 Treatment on Neurodegenerative and Gliotic Pathology

Figure 8:
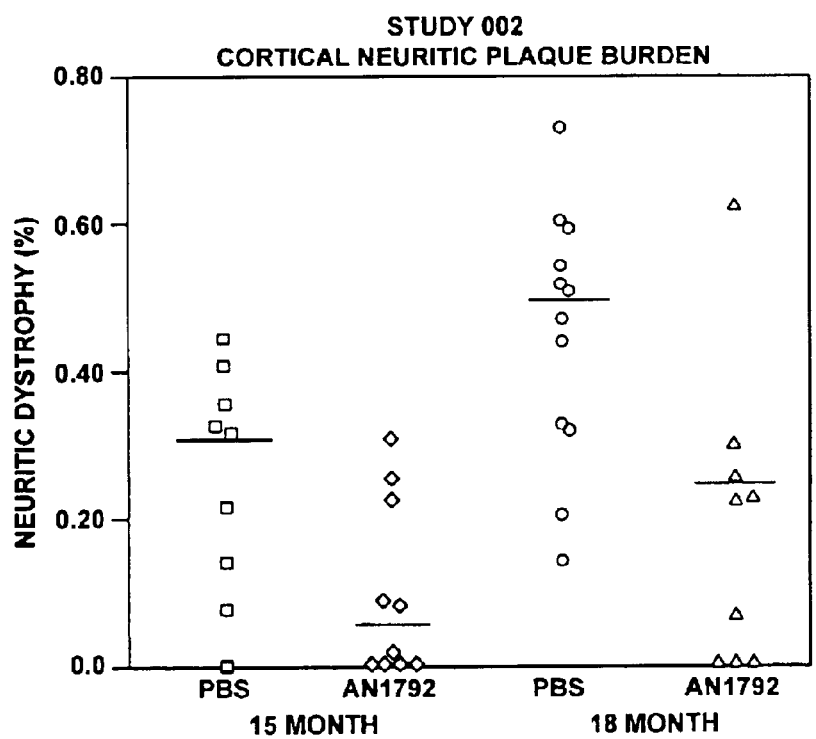
FIG. 8: Quantitative image analysis of the neuritic plaque burden in PBS- and AN1792-treated mice.

Neuritic plaque burden was significantly reduced in the frontal cortex of AN1792-treated mice compared to the PBS group at both 15 (84%; p=0.03) and 18 (55%; p=0.01) months of age (FIG. 8). The median value of the neuritic plaque burden increased from 0.32% to 0.49% in the PBS group between 15 and 18 months of age. This contrasted with the greatly reduced development of neuritic plaques in the AN1792 group, with median neuritic plaque burden values of 0.05% and 0.22%, in the 15 and 18 month groups, respectively.

Figure 9:
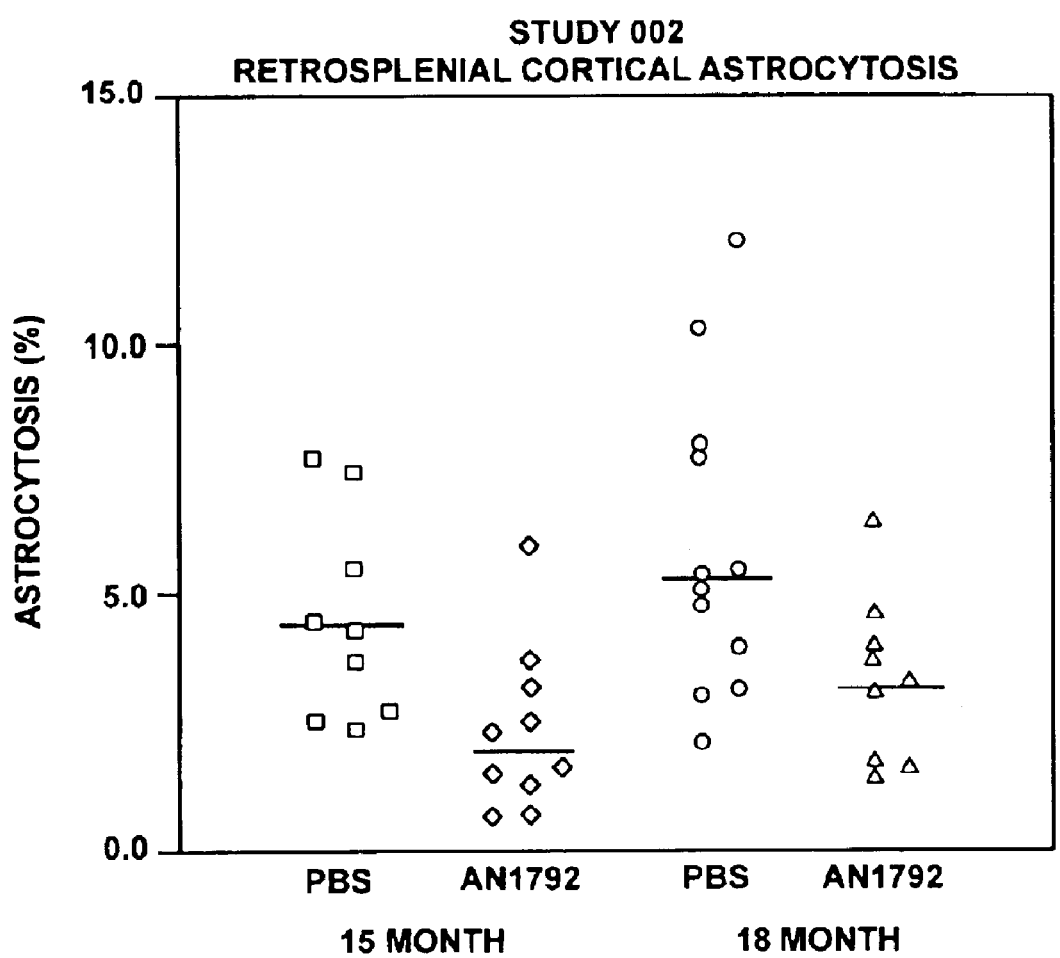
FIG. 9: Quantitative image analysis of the percent of the retrosplenial cortex occupied by astrocytosis in PBS- and AN1792-treated mice.

Immunizations with AN1792 seemed well tolerated and reactive astrocytosis was also significantly reduced in the RSC of AN1792-treated mice when compared to the PBS group at both 15 (56%; p=0.011) and 18 (39%; p=0.028) months of age (FIG. 9). Median values of the percent of astrocytosis in the PBS group increased between 15 and 18 months from 4.26% to 5.21%. AN1792-treatment suppressed the development of astrocytosis at both time points to 1.89% and 3.2%, respectively. This suggests the neuropil was not being damaged by the clearance process.

6. Antibody Responses

As described above, eleven-month old, heterozygous PDAPP mice (N=24) received a series of 5 immunizations of 100 μg of AN1792 emulsified with Freund's adjuvant and administered intraperitoneally at weeks 0, 2, 4, 8, and 12, and a sixth immunization with PBS alone (no Freund's adjuvant) at week 16. As a negative control, a parallel set of 24 age-matched transgenic mice received immunizations of PBS emulsified with the same adjuvants and delivered on the same schedule. Animals were bled within three to seven days following each immunization starting after the second dose. Antibody responses to AN1792 were measured by ELISA. Geometric mean titers (GMT) for the animals that were immunized with AN1792 were approximately 1,900, 7,600, and 45,000 following the second, third and last (sixth) doses respectively. No Aβ-specific antibody was measured in control animals following the sixth immunization.

Approximately one-half of the animals were treated for an additional three months, receiving immunizations at about 20, 24 and 27 weeks. Each of these doses was delivered in PBS vehicle alone without Freund's adjuvant. Mean antibody titers remained unchanged over this time period. In fact, antibody titers appeared to remain stable from the fourth to the eighth bleed corresponding to a period covering the fifth to the ninth injections.

To determine if the Aβ-specific antibodies elicited by immunization that were detected in the sera of AN1792-treated mice were also associated with deposited brain amyloid, a subset of sections from the AN1792- and PBS-treated mice were reacted with an antibody specific for mouse IgG. In contrast to the PBS group, Aβ plaques in AN1792-treated brains were coated with endogenous IgG. This difference between the two groups was seen in both 15- and 18-month groups. Particularly striking was the lack of labeling in the PBS group, despite the presence of a heavy amyloid burden in these mice. These results show that immunization with a synthetic Aβ protein generates antibodies that recognize and bind in vivo to the Aβ in amyloid plaques.

7. Cellular-Mediated Immune Responses

Figure 10A:
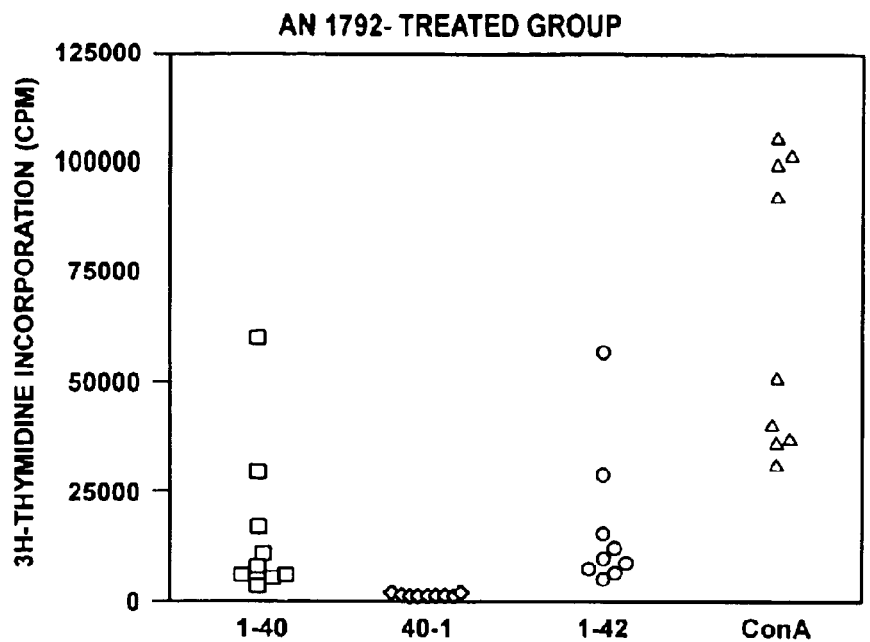
FIG. 10: Lymphocyte Proliferation Assay on spleen cells from AN1792-treated (FIG. 10A) or PBS-treated (FIG. 10B).
Figure 10B:
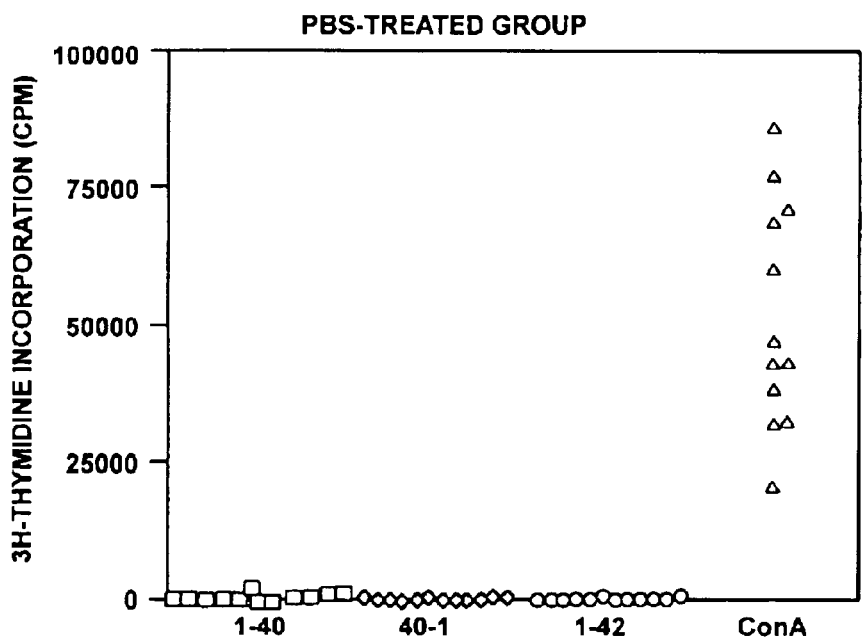

Spleens were removed from nine AN1792-immunized and 12 PBS-immunized 18-month old PDAPP mice 7 days after the ninth immunization. Splenocytes were isolated and cultured for 72 h in the presence of Aβ40, Aβ42, or Aβ40-1 (reverse order protein). The mitogen Con A served as a positive control. Optimum responses were obtained with >1.7 μM protein. Cells from all nine AN1792-treated animals proliferated in response to either Aβ1-40 or Aβ1-42 protein, with equal levels of incorporation for both proteins (FIG. 10A). There was no response to the Aβ40-1 reverse protein. Cells from control animals did not respond to any of the Aβ proteins (FIG. 10B).

C. Conclusion

The results of this study show that AN1792 immunization of PDAPP mice possessing existing amyloid deposits slows and prevents progressive amyloid deposition and retard consequential neuropathological changes in the aged PDAPP mouse brain. Immunizations with AN1792 essentially halted amyloid developing in structures that would normally succumb to amyloidosis. Thus, administration of Aβ peptide has therapeutic benefit in the treatment of AD.

Example IV

Screen of Aβ Fragments

100 PDAPP mice age 7–9 months are immunized with 9 different regions of APP and Aβ to determine which epitopes convey the response. The 9 different immunogens and one control are injected i.p. as described above. The immunogens include four human Aβ peptide conjugates 1-12, 13-28, 32-42, 1-5, all coupled to sheep anti-mouse IgG via a cystine link; an APP polypeptide aa 592-695, aggregated human Aβ 1-40, and aggregated human Aβ 25-35, and aggregated rodent Aβ42. Aggregated Aβ42 and PBS are used as controls. Ten mice are used per treatment group. Titers are monitored as above and mice are euthanized at the end of 4 months of injections. Histochemistry, Aβ levels, and toxicology are determined post mortem.

A. Materials and Methods

1. Preparation of Immunogens

Preparation of coupled Aβ peptides: four human Aβ peptide conjugates (amino acid residues 1-5, 1-12, 13-28, and 33-42, each conjugated to sheep anti-mouse IgG) were prepared by coupling through an artificial cysteine added to the Aβ peptide using the crosslinking reagent sulfo-EMCS. The Aβ peptide derivatives were synthesized with the following final amino acid sequences. In each case, the location of the inserted cysteine residue is indicated by underlining. The Aβ13-28 peptide derivative also had two glycine residues added prior to the carboxyl terminal cysteine as indicated.

Aβ1-12 peptide (SEQ ID NO:2)
NH₂-DAEFRHDSGYEVC-COOH

Aβ1-5 peptide (SEQ ID NO:3)
NH₂-DAEFRC-COOH

Aβ33-42 peptide (SEQ ID NO:4)
NH₂-C-amino-heptanoic acid-GLMVGGVVIA-COOH

Aβ13-28 peptide (SEQ ID NO:5)
Ac-NH-HHQKLVFFAEDVGSNKGGC-COOH

To prepare for the coupling reaction, ten mg of sheep anti-mouse IgG (Jackson ImmunoResearch Laboratories) was dialyzed overnight against 10 mM sodium borate buffer, pH 8.5. The dialyzed antibody was then concentrated to a volume of 2 mL using an Amicon Centriprep tube. Ten mg sulfo-EMCS [N (ε-maleimidocuproyloxy) succinimide] (Molecular Sciences Co.) was dissolved in one mL deionized water. A 40-fold molar excess of sulfo-EMCS was added dropwise with stirring to the sheep anti-mouse IgG and then the solution was stirred for an additional ten min. The activated sheep anti-mouse IgG was purified and buffer exchanged by passage over a 10 mL gel filtration column (Pierce Presto Column, obtained from Pierce Chemicals) equilibrated with 0.1 M NaPO₄, 5 mM EDTA, pH 6.5. Antibody containing fractions, identified by absorbance at 280 nm, were pooled and diluted to a concentration of approximately 1 mg/mL, using 1.4 mg per OD as the extinction coefficient. A 40-fold molar excess of Aβ peptide was dissolved in 20 mL of 10 mM NaPO₄, pH 8.0, with the exception of the Aβ33-42 peptide for which 10 mg was first dissolved in 0.5 mL of DMSO and then diluted to 20 mL with the 10 mM NaPO₄ buffer. The peptide solutions were each added to 10 mL of activated sheep anti-mouse IgG and rocked at room temperature for 4 hr. The resulting conjugates were concentrated to a final volume of less than 10 mL using an Amicon Centriprep tube and then dialyzed against PBS to buffer exchange the buffer and remove free peptide. The conjugates were passed through 0.22 μ-pore size filters for sterilization and then aliquoted into fractions of 1 mg and stored frozen at −20° C. The concentrations of the conjugates were determined using the BCA protein assay (Pierce Chemicals) with horse IgG for the standard curve. Conjugation was documented by the molecular weight increase of the conjugated peptides relative to that of the activated sheep anti-mouse IgG. The Aβ 1-5 sheep anti-mouse conjugate was a pool of two conjugations, the rest were from a single preparation.

2. Preparation of Aggregated Aβ Peptides

Human 1-40 (AN1528; California Peptides Inc., Lot ME0541), human 1-42 (AN1792; California Peptides Inc., Lots ME0339 and ME0439), human 25-35, and rodent 1-42 (California Peptides Inc., Lot ME0218) peptides were freshly solubilized for the preparation of each set of injections from lyophilized powders that had been stored desiccated at −20° C. For this purpose, two mg of peptide were added to 0.9 ml of deionized water and the mixture was vortexed to generate a relatively uniform solution or suspension. Of the four, AN1528 was the only peptide soluble at this step. A 100 μl aliquot of 10× PBS (1× PBS: 0.15 M NaCl, 0.01 M sodium phosphate, pH 7.5) was then added at which point AN1528 began to precipitate. The suspension was vortexed again and incubated overnight at 37° C. for use the next day.

Preparation of the pBx6 protein: An expression plasmid encoding pBx6, a fusion protein consisting of the 100-amino acid bacteriophage MS-2 polymerase N-terminal leader sequence followed by amino acids 592–695 of APP (βAPP) was constructed as described by Oltersdorf et al., *J. Biol. Chem.* 265, 4492–4497 (1990). The plasmid was transfected into *E. coli* and the protein was expressed after induction of the promoter. The bacteria were lysed in 8M urea and pBx6 was partially purified by preparative SDS PAGE. Fractions containing pBx6 were identified by Western blot using a rabbit anti-pBx6 polyclonal antibody, pooled, concentrated using an Amicon Centriprep tube and dialysed against PBS. The purity of the preparation, estimated by Comassie Blue stained SDS PAGE, was approximately 5 to 10%.

B. Results and Discussion

1. Study Design

One hundred male and female, nine- to eleven-month old heterozygous PDAPP transgenic mice were obtained from Charles River Laboratory and Taconic Laboratory. The mice were sorted into ten groups to be immunized with different regions of Aβ or APP combined with Freund's adjuvant. Animals were distributed to match the gender, age, parentage and source of the animals within the groups as closely as possible. The immunogens included four Aβ peptides derived from the human sequence, 1-5, 1-12, 13-28, and 33-42, each conjugated to sheep anti-mouse IgG; four aggregated Aβ peptides, human 1-40 (AN1528), human 1-42 (AN1792), human 25-35, and rodent 1-42; and a fusion polypeptide, designated as pBx6, containing APP amino acid residues 592–695. A tenth group was immunized with PBS combined with adjuvant as a control.

For each immunization, 100 μg of each Aβ peptide in 200 μl PBS or 200 g of the APP derivative pBx6 in the same volume of PBS or PBS alone was emulsified 1:1 (vol:vol) with Complete Freund's adjuvant (CFA) in a final volume of 400 μl for the first immunization, followed by a boost of the same amount of immunogen in Incomplete Freund's adjuvant (IFA) for the subsequent four doses and with PBS for the final dose. Immunizations were delivered intraperitoneally on a biweekly schedule for the first three doses, then on a monthly schedule thereafter. Animals were bled four to seven days following each immunization starting after the second dose for the measurement of antibody titers. Animals were euthanized approximately one week after the final dose.

2. Aβ and APP Levels in the Brain

Following about four months of immunization with the various Aβ peptides or the APP derivative, brains were removed from saline-perfused animals. One hemisphere was prepared for immunohistochemical analysis and the second was used for the quantitation of Aβ and APP levels. To measure the concentrations of various forms of beta amyloid peptide and amyloid precursor protein, the hemisphere was dissected and homogenates of the hippocampal, cortical, and cerebellar regions were prepared in 5 M guanidine. These were diluted and the level of amyloid or APP was quantitated by comparison to a series of dilutions of standards of Aβ peptide or APP of known concentrations in an ELISA format.

The median concentration of total Aβ for the control group immunized with PBS was 5.8-fold higher in the hippocampus than in the cortex (median of 24,318 ng/g hippocampal tissue compared to 4,221 ng/g for the cortex). The median level in the cerebellum of the control group (23.4 ng/g tissue) was about 1,000-fold lower than in the hippocampus. These levels are similar to those that we have previously reported for heterozygous PDAPP transgenic mice of this age (Johnson-Woods et al., 1997, supra).

Figure 11:
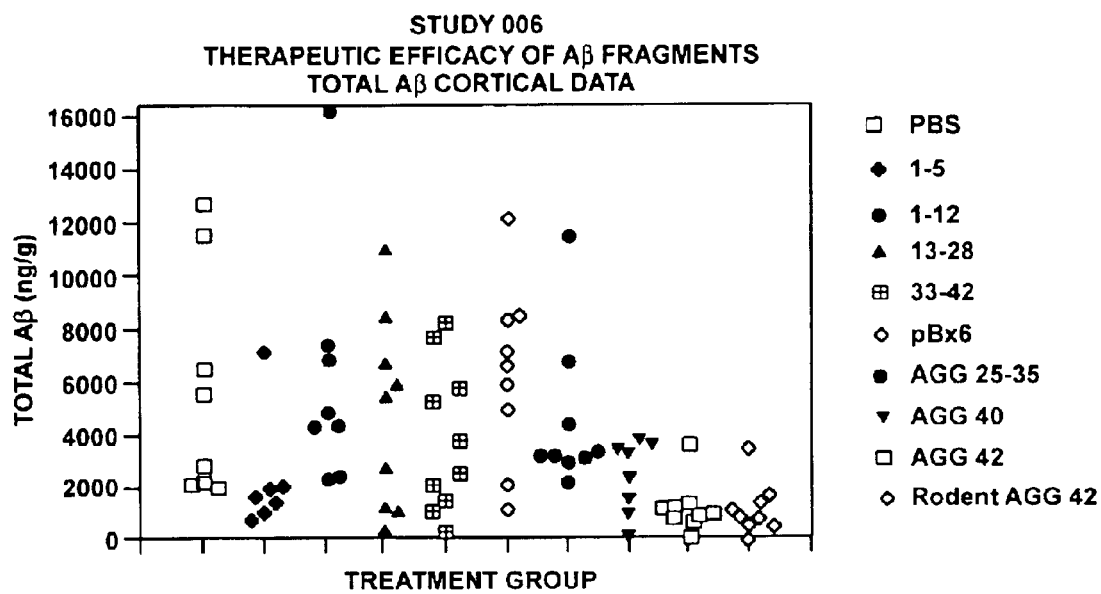
FIG. 11: Total Aβ levels in the cortex. A scatterplot of individual Aβ profiles in mice immunized with Aβ or APP derivatives combined with Freund's adjuvant.

For the cortex, a subset of treatment groups had median total Aβ and Aβ1-42 levels which differed significantly from those of the control group ($p<0.05$), those animals receiving AN1792, rodent Aβ1-42 or the Aβ1-5 peptide conjugate as shown in FIG. 11. The median levels of total Aβ were reduced by 75%, 79% and 61%, respectively, compared to the control for these treatment groups. There were no discernable correlations between Aβ-specific antibody titers and Aβ levels in the cortical region of the brain for any of the groups.

In the hippocampus, the median reduction of total Aβ associated with AN1792 treatment (46%, $p=0.0543$) was not as great as that observed in the cortex (75%, $p=0.0021$). However, the magnitude of the reduction was far greater in the hippocampus than in the cortex, a net reduction of 11,186 ng/g tissue in the hippocampus versus 3,171 ng/g tissue in the cortex. For groups of animals receiving rodent Aβ1-42 or Aβ1-5, the median total Aβ levels were reduced by 36% and 26%, respectively. However, given the small group sizes and the high variability of the amyloid peptide levels from animal to animal within both groups, these reductions were not significant. When the levels of Aβ1-42 were measured in the hippocampus, none of the treatment-induced reductions reached significance. Thus, due to the smaller Aβ burden in the cortex, changes in this region are a more sensitive indicator of treatment effects. The changes in Aβ levels measured by ELISA in the cortex are similar, but not identical, to the results from the immunohistochemical analysis (see below).

Total Aβ was also measured in the cerebellum, a region typically unaffected in the AD pathology. None of the median Aβ concentrations of any of the groups immunized with the various Aβ peptides or the APP derivative differed from that of the control group in this region of the brain. This result suggests that non-pathological levels of Aβ are unaffected by treatment.

APP concentration was also determined by ELISA in the cortex and cerebellum from treated and control mice. Two different APP assays were utilized. The first, designated APP-α/FL, recognizes both APP-alpha (a, the secreted form of APP which has been cleaved within the Aβ sequence), and full-length forms (FL) of APP, while the second recognizes only APP-α. In contrast to the treatment-associated diminution of Aβ in a subset of treatment groups, the levels of APP were unchanged in all of the treated compared to the control animals. These results indicate that the immunizations with Aβ peptides are not depleting APP; rather the treatment effect is specific to Aβ.

In summary, total Aβ and Aβ1-42 levels were significantly reduced in the cortex by treatment with AN1792, rodent Aβ1-42 or Aβ1-5 conjugate. In the hippocampus, total Aβ was significantly reduced only by AN1792 treatment. No other treatment-associated changes in Aβ or APP levels in the hippocampal, cortical or cerebellar regions were significant.

3. Histochemical Analyses

Figure 12:
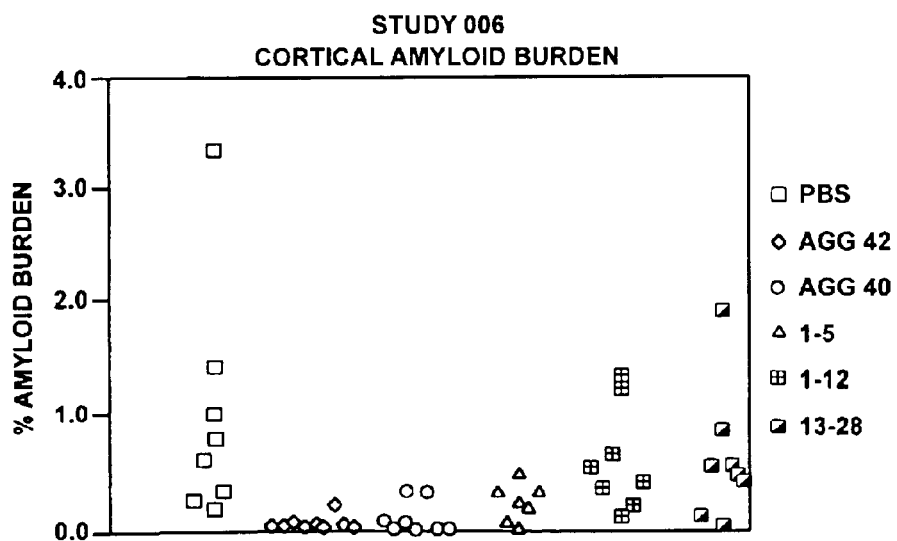
FIG. 12: Amyloid burden in the cortex was determined by quantitative image analysis of immunoreacted brain sections for mice immunized with the Aβ peptide conjugates Aβ1-5, Aβ1-12, and Aβ13-28; the full length Aβ aggregates AN1792 (Aβ1-42) and AN1528 (Aβ1-40) and the PBS-treated control group.

Brains from a subset of six groups were prepared for immunohistochemical analysis, three groups immunized with the Aβ peptide conjugates Aβ1-5, Aβ1-12, and Aβ13-28; two groups immunized with the full length Aβ aggregates AN1792 and AN1528 and the PBS-treated control group. The results of image analyses of the amyloid burden in brain sections from these groups are shown in FIG. 12. There were significant reductions of amyloid burden in the cortical regions of three of the treatment groups versus control animals. The greatest reduction of amyloid burden was observed in the group receiving AN1792 where the mean value was reduced by 97% ($p=0.001$). Significant reductions were also observed for those animals treated with AN1528 (95%, $p=0.005$) and the Aβ1-5 peptide conjugate (67%, $p=0.02$).

The results obtained by quantitation of total Aβ or Aβ1-42 by ELISA and amyloid burden by image analysis differ to some extent. Treatment with AN1528 had a significant impact on the level of cortical amyloid burden when measured by quantitative image analysis but not on the concentration of total Aβ in the same region when measured by ELISA. The difference between these two results is likely to be due to the specificities of the assays. Image analysis measures only insoluble Aβ aggregated into plaques. In contrast, the ELISA measures all forms of Aβ, both soluble and insoluble, monomeric and aggregated. Since the disease pathology is thought to be associated with the insoluble plaque-associated form of Aβ, the image analysis technique may have more sensitivity to reveal treatment effects. However since the ELISA is a more rapid and easier assay, it is very useful for screening purposes. Moreover it may reveal that the treatment-associated reduction of Aβ is greater for plaque-associated than total Aβ.

To determine if the Aβ-specific antibodies elicited by immunization in the treated animals reacted with deposited brain amyloid, a subset of the sections from the treated animals and the control mice were reacted with an antibody specific for mouse IgG. In contrast to the PBS group, Aβ-containing plaques were coated with endogenous IgG for animals immunized with the Aβ peptide conjugates Aβ1-5, Aβ1-12, and Aβ13-28; and the full length Aβ aggregates AN1792 and AN1528. Brains from animals immunized with the other Aβ peptides or the APP peptide pBx6 were not analyzed by this assay.

4. Measurement of Antibody Titers

Figure 13:
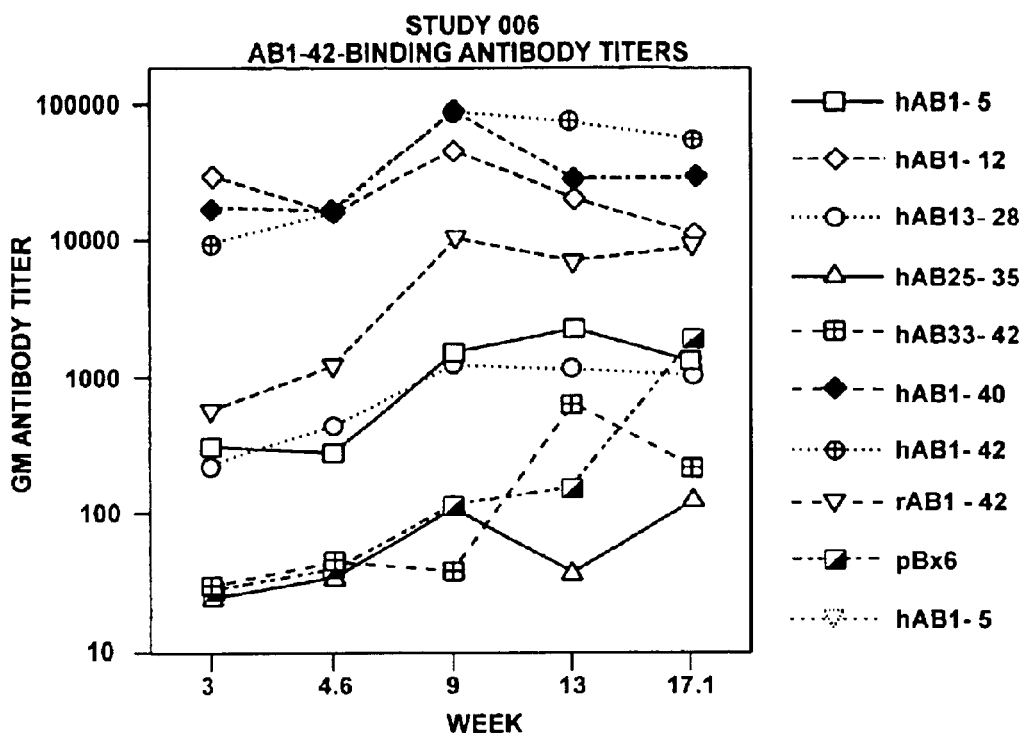
FIG. 13: Geometric mean titers of Aβ-specific antibody for groups of mice immunized with Aβ or APP derivatives combined with Freund's adjuvant.

Mice were bled four to seven days following each immunization starting after the second immunization, for a total of five bleeds. Antibody titers were measured as Aβ 1-42-binding antibody using a sandwich ELISA with plastic multi-well plates coated with Aβ 1-42. As shown in FIG. 13, peak antibody titers were elicited following the fourth dose for those four vaccines which elicited the highest titers of AN1792-specific antibodies: AN1792 (peak GMT: 94,647), AN1528 (peak GMT: 88,231), Aβ1-12 conjugate (peak GMT: 47,216) and rodent Aβ 1-42 (peak GMT: 10,766). Titers for these groups declined somewhat following the fifth and sixth doses. For the remaining five immunogens, peak titers were reached following the fifth or the sixth dose and these were of much lower magnitude than those of the four highest titer groups: Aβ1-5 conjugate (peak GMT: 2,356), pBx6 (peak GMT: 1,986), Aβ13-28 conjugate (peak GMT: 1,183), Aβ33-42 conjugate (peak GMT: 658), Aβ25-35 (peak GMT: 125). Antibody titers were also measured against the homologous peptides using the same ELISA sandwich format for a subset of the immunogens, those groups immunized with Aβ1-5, Aβ13-28, A25-35, Aβ33-42 or rodent Aβ-42. These titers were about the same as those measured against Aβ1-42 except for the rodent Aβ1-42 immunogen in which case antibody titers against the homologous immunogen were about two-fold higher. The magnitude of the AN1792-specific antibody titer of individual animals or the mean values of treatment groups did not correlate with efficacy measured as the reduction of Aβ in the cortex.

5. Lymphoproliferative Responses

Aβ-dependent lymphoproliferation was measured using spleen cells harvested approximately one week following the final, sixth, immunization. Freshly harvested cells, $10^5$ per well, were cultured for 5 days in the presence of Aβ 1-40 at a concentration of 5 μM for stimulation. Cells from a subset of seven of the ten groups were also cultured in the presence of the reverse peptide, Aβ40-1. As a positive control, additional cells were cultured with the T cell mitogen, PHA, and, as a negative control, cells were cultured without added peptide.

Lymphocytes from a majority of the animals proliferated in response to PHA. There were no significant responses to the Aβ40-1 reverse peptide. Cells from animals immunized with the larger aggregated Aβ peptides, AN1792, rodent Aβ1-42 and AN1528 proliferated robustly when stimulated with Aβ 1-40 with the highest cpm in the recipients of AN1792. One animal in each of the groups immunized with Aβ1-12 conjugate, Aβ 13-28 conjugate and Aβ25-35 proliferated in response to Aβ1-40. The remaining groups receiving Aβ1-5 conjugate, Aβ33-42 conjugate pBx6 or PBS had no animals with an Aβ-stimulated response. These results are summarized in Table 5 below.

TABLE 5

| Immunogen | Conjugate | Aβ Amino Acids | Responders |
|---|---|---|---|
| Aβ1-5 | yes | 5-mer | 0/7 |
| Aβ1-12 | yes | 12-mer | 1/8 |
| Aβ13-28 | yes | 16-mer | 1/9 |
| Aβ25-35 |  | 11-mer | 1/9 |
| Aβ33-42 | yes | 10-mer | 0/10 |
| Aβ1-40 |  | 40-mer | 5/8 |
| Aβ1-42 |  | 42-mer | 9/9 |
| r Aβ1-42 |  | 42-mer | 8/8 |
| pBx6 |  |  | 0/8 |
| PBS |  | 0-mer | 0/8 |

These results show that AN1792 and AN1528 stimulate strong T cell responses, most likely of the CD4+ phenotype. The absence of an Aβ-specific T cell response in animals immunized with Aβ 1-5 is not surprising since peptide epitopes recognized by CD4+ T cells are usually about 15 amino acids in length, although shorter peptides can sometimes function with less efficiency. Thus the majority of helper T cell epitopes for the four conjugate peptides are likely to reside in the IgG conjugate partner, not in the Aβ region. This hypothesis is supported by the very low incidence of proliferative responses for animals in each of these treatment groups. Since the Aβ 1-5 conjugate was effective at significantly reducing the level of Aβ in the brain, in the apparent absence of Aβ-specific T cells, the key effector immune response induced by immunization with this peptide appears to be antibody.

Lack of T-cell and low antibody response from fusion peptide pBx6, encompassing APP amino acids 592–695 including all of the Aβ residues may be due to the poor immunogenicity of this particular preparation. The poor immunogenicity of the Aβ25-35 aggregate is likely due to the peptide being too small to be likely to contain a good T cell epitope to help the induction of an antibody response. If this peptide were conjugated to a carrier protein, it would probably be more immunogenic.

Example V

Preparation of Polyclonal Antibodies for Passive Protection 20 non-transgenic mice are immunized with Aβ or other immunogen, optionally plus adjuvant, and are euthanized at 4–5 months. Blood is collected from immunized mice. Optionally, IgG is separated from other blood components. Antibody specific for the immunogen may be partially purified by affinity chromatography. An average of about 0.5–1 mg of immunogen-specific antibody is obtained per mouse, giving a total of 5–10 mg.

Example VI

Passive Immunization with Antibodies to Aβ

Groups of 7–9 month old PDAPP mice each are injected with 0.5 mg in PBS of polyclonal anti-Aβ or specific anti-Aβ monoclonals as shown below. The cell line designated RB44-10D5.19.21 producing the antibody 10D5 has the ATCC accession number PTA-5129, having been deposited on Apr. 8, 2003. All antibody preparations are purified to have low endotoxin levels. Monoclonals can be prepared against a fragment by injecting the fragment or longer form of Aβ into a mouse, preparing hybridomas and screening the hybridomas for an antibody that specifically binds to a desired fragment of Aβ without binding to other nonoverlapping fragments of Aβ.

TABLE 6

| Antibody | Epitope |
|---|---|
| 2H3 | Aβ 1-12 |
| 10D5 | Aβ 1-12 |
| 266 | Aβ 13-28 |
| 21F12 | Aβ 33-42 |
| Mouse polyclonal anti-human AB42 | Anti-Aggregated Aβ42 |

Mice are injected ip as needed over a 4 month period to maintain a circulating antibody concentration measured by ELISA titer of greater than 1/1000 defined by ELISA to Aβ42 or other immunogen. Titers are monitored as above and mice are euthanized at the end of 4 months of injections. Histochemistry, Aβ levels and toxicology are performed post mortem. Ten mice are used per group.

Example VII

Comparison of Different Adjuvants

This examples compares CFA, alum, an oil-in water emulsion and MPL for capacity to stimulate an immune response.

A. Materials and Methods

1. Study Design

One hundred female Hartley strain six-week old guinea pigs, obtained from Elm Hill, were sorted into ten groups to be immunized with AN1792 or a palmitoylated derivative thereof combined with various adjuvants. Seven groups received injections of AN1792 (33 μg unless otherwise specified) combined with a) PBS, b) Freund's adjuvant, c) MPL, d) squalene, e) MPL/squalene f) low dose alum, or g) high dose alum (300μg AN1792). Two groups received injections of a palmitoylated derivative of AN1792 (33 μg) combined with a) PBS or b) squalene. A final, tenth group received PBS alone without antigen or additional adjuvant. For the group receiving Freund's adjuvant, the first dose was emulsified with CFA and the remaining four doses with IFA. Antigen was administered at a dose of 33 μg for all groups except the high dose alum group, which received 300 μg of AN1792. Injections were administered intraperitoneally for CFA/IFA and intramuscularly in the hind limb quadriceps alternately on the right and left side for all other groups. The first three doses were given on a biweekly schedule followed by two doses at a monthly interval). Blood was drawn six to seven days following each immunization, starting after the second dose, for measurement of antibody titers.

2. Preparation of Immunogens

Two mg Aβ42 (California Peptide, Lot ME0339) was added to 0.9 ml of deionized water and the mixture was vortexed to generate a relatively uniform suspension. A 100 μl aliquot of 10× PBS (1× PBS, 0.15 M NaCl, 0.01 M sodium phosphate, pH 7.5) was added. The suspension was vortexed again and incubated overnight at 37° C. for use the next day. Unused Aβ 1-42 was stored with desiccant as a lyophilized powder at −20° C.

to the amino terminal residue of AN1792 prior to removal of the nascent peptide from the resin by treatment with A palmitoylated derivative of AN1792 was prepared by coupling palmitic anhydride, dissolved in dimethyl formamide, hydrofluoric acid.

To prepare vaccine doses with Complete Freund's adjuvant (CFA) (group 2), 33 μg of AN1792 in 200 μl PBS was emulsified 1:1 (vol:vol) with CFA in a final volume of 400 μl for the first immunization. For subsequent immunizations, the antigen was similarly emulsified with Incomplete Freund's adjuvant (IFA).

To prepare vaccine doses with MPL for groups 5 and 8, lyophilized powder (Ribi ImmunoChem Research, Inc., Hamilton, Mont.) was added to 0.2% aqueous triethylamine to a final concentration of 1 mg/ml and vortexed. The mixture was heated to 65 to 70° C. for 30 sec to create a slightly opaque uniform suspension of micelles. The solution was freshly prepared for each set of injections. For each injection in group 5, 33 μg of AN1792 in 16.5 μl PBS, 50 μg of MPL (50 μl) and 162 μl of PBS were mixed in a borosilicate tube immediately before use.

To prepare vaccine doses with the low oil-in-water emulsion, AN1792 in PBS was added to 5% squalene, 0.5% Tween 80, 0.5% Span 85 in PBS to reach a final single dose concentration of 33 μg AN1792 in 250 μl (group 6). The mixture was emulsified by passing through a two-chambered hand-held device 15 to 20 times until the emulsion droplets appeared to be about equal in diameter to a 1.0 μm diameter standard latex bead when viewed under a microscope. The resulting suspension was opalescent, milky white. The emulsions were freshly prepared for each series of injections. For group 8, MPL in 0.2% triethylamine was added at a concentration of 50 μg per dose to the squalene and detergent mixture for emulsification as noted above. For the palmitoyl derivative (group 7), 33 μg per dose of palmitoyl-NH-Aβ1-42 was added to squalene and vortexed. Tween 80 and Span 85 were then added with vortexing. This mixture was added to PBS to reach final concentrations of 5% squalene, 0.5% Tween 80, 0.5% Span 85 and the mixture was emulsified as noted above.

To prepare vaccine doses with alum (groups 9 and 10), AN1792 in PBS was added to Alhydrogel (aluminum hydroxide gel, Accurate, Westbury, N.Y.) to reach concentrations of 33 μg (low dose, group 9) or 300 μg (high dose, group 10) AN1792 per 5 mg of alum in a final dose volume of 250 μl. The suspension was gently mixed for 4 hr at RT.

3. Measurement of Antibody Titers

Guinea pigs were bled six to seven days following immunization starting after the second immunization for a total of four bleeds. Antibody titers against Aβ42 were measured by ELISA as described in General Materials and Methods.

4. Tissue Preparation

After about 14 weeks, all guinea pigs were administered $CO_2$. Cerebrospinal fluid was collected and the brains were removed and three brain regions (hippocampus, cortex and cerebellum) were dissected and used to measure the concentration of total Aβ protein using ELISA.

B. Results

1. Antibody Responses

Figure 14:
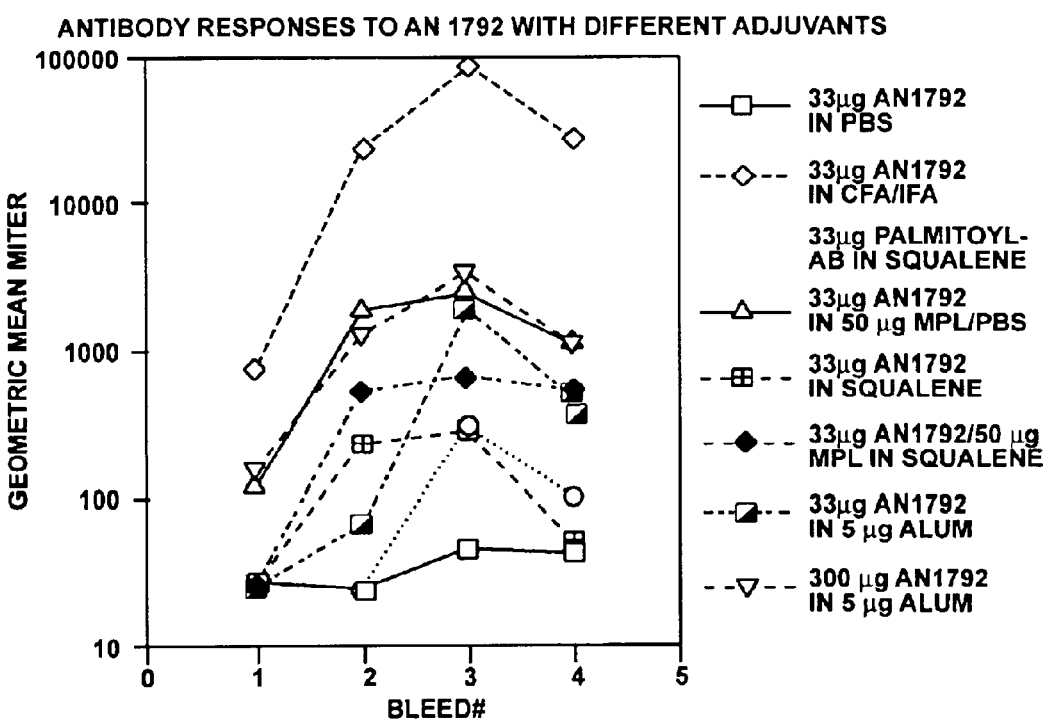
FIG. 14: Geometric mean titers of Aβ-specific antibody for groups of guinea pigs immunized with AN1792, or a palmitoylated derivative thereof, combined with various adjuvants.

There was a wide range in the potency of the various adjuvants when measured as the antibody response to AN1792 following immunization. As shown in FIG. 14, when AN1792 was administered in PBS, no antibody was detected following two or three immunizations and negligible responses were detected following the fourth and fifth doses with geometric mean titers (GMTs) of only about 45. The o/w emulsion induced modest titers following the third dose (GMT 255) that were maintained following the fourth dose (GMT 301) and fell with the final dose (GMT 54). There was a clear antigen dose response for AN1792 bound to alum with 300 μg being more immunogenic at all time points than 33 μg. At the peak of the antibody response, following the fourth immunization, the difference between the two doses was 43% with GMTs of about 1940 (33 μg) and 3400 (300 μg). The antibody response to 33 μg AN1792 plus MPL was very similar to that generated with almost a ten-fold higher dose of antigen (300 μg) bound to alum. The addition of MPL to an o/w emulsion decreased the potency of the vaccine relative to that with MPL as the sole adjuvant by as much as 75%. A palmitoylated derivative of AN1792 was completely non-immunogenic when administered in PBS and gave modest titers when presented in an o/w emulsion with GMTs of 340 and 105 for the third and fourth bleeds. The highest antibody titers were generated with Freund's adjuvant with a peak GMT of about 87,000, a value almost 30-fold greater than the GMTs of the next two most potent vaccines, MPL and high dose AN1792/alum.

The most promising adjuvants identified in this study are MPL and alum. Of these two, MPL appears preferable because a 10-fold lower antigen dose was required to generate the same antibody response as obtained with alum. The response can be increased by increasing the dose of antigen and/or adjuvant and by optimizing the immunization schedule. The o/w emulsion was a very weak adjuvant for AN1792 and adding an o/w emulsion to MPL adjuvant diminished the intrinsic adjuvant activity of MPL alone.

2. Aβ Levels in the Brain

At about 14 weeks the guinea pigs were deeply anesthetized, the cerebrospinal fluid (CSF) was drawn and brains were excised from animals in a subset of the groups, those immunized with Freund's adjuvant (group 2), MPL (group 5), alum with a high dose, 300 μg, of AN1792 (group 10) and the PBS immunized control group (group 3). To measure the level of Aβ peptide, one hemisphere was dissected and homogenates of the hippocampal, cortical, and cerebellar regions were prepared in 5 M guanidine. These were diluted and quantitated by comparison to a series of dilutions of Aβ standard protein of known concentrations in an ELISA format. The levels of Aβ protein in the hippocampus, the cortex and the cerebellum were very similar for all four groups despite the wide range of antibody responses to Aβ elicited by these vaccines. Mean Aβ levels of about 25 ng/g tissue were measured in the hippocampus, 21 ng/g in the cortex, and 12 ng/g in the cerebellum. Thus, the presence of a high circulating antibody titer to Aβ for almost three months in some of these animals did not alter the total Aβ levels in their brains. The levels of Aβ in the CSF were also quite similar between the groups. The lack of large effect of AN1792 immunization on endogenous Aβ indicates that the immune response is focused on pathological formations of Aβ.

Example VIII

Immune Response to Different Adjuvants in Mice

Six-week-old female Swiss Webster mice were used for this study with 10–13 animals per group. Immunizations were given on days 0, 14, 28, 60, 90 and 20 administered subcutaneously in a dose volume of 200 μl. PBS was used as the buffer for all formulations. Animals were bleed seven days following each immunization starting after the second dose antibody titers by ELISA. The treatment regime of each group is summarized Table 7.

TABLE 7

Experimental Design of Betabloc Study 010

| Group | N[a] | Adjuvant[b] | Dose | Antigen | Dose (μg) |
|---|---|---|---|---|---|
| 1 | 10 | MPL | 12.5 μg | AN1792 | 33 |
| 2 | 10 | MPL | 25 μg | AN1792 | 33 |
| 3 | 10 | MPL | 50 μg | AN1792 | 33 |
| 4 | 13 | MPL | 125 μg | AN1792 | 33 |
| 5 | 13 | MPL | 50 μg | AN1792 | 150 |
| 6 | 13 | MPL | 50 μg | AN1528 | 33 |
| 7 | 10 | PBS | | AN1792 | 33 |
| 8 | 10 | PBS | | none | |
| 9 | 10 | Squalene emulsified | 5% | AN1792 | 33 |
| 10 | 10 | Squalene admixed | 5% | AN1792 | 33 |
| 11 | 10 | Alum | 2 mg | AN1792 | 33 |
| 12 | 13 | MPL + Alum | 50 μg/2 mg | AN1792 | 33 |
| 13 | 10 | QS21 | 5 μg | AN1792 | 33 |
| 14 | 10 | QS21 | 10 μg | AN1792 | 33 |
| 15 | 10 | QS21 | 25 μg | AN1792 | 33 |
| 16 | 13 | QS21 | 25 μg | AN1792 | 150 |
| 17 | 13 | QS21 | 25 μg | AN1528 | 33 |
| 18 | 13 | QS21 + MPL | 25 μg/50 μg | AN1792 | 33 |
| 19 | 13 | QS21 + Alum | 25 μg/2 mg | AN1792 | 33 |

Footnotes:
[a]Number of mice in each group at the initiation of the experiment.
[b]The adjuvants are noted. The buffer for all these formulations was PBS. For group 8, there was no adjuvant and no antigen.

ELISA titers of antibodies against Aβ42 in each group are shown in Table 8 below.

TABLE 8

Geometric Mean Antibody Titers Week of Bleed

| Treatment Group | 2.9 | 5.0 | 8.7 | 12.9 | 16.7 |
|---|---|---|---|---|---|
| 1 | 248 | 1797 | 2577 | 6180 | 4177 |
| 2 | 598 | 3114 | 3984 | 5287 | 6878 |
| 3 | 1372 | 5000 | 7159 | 12333 | 12781 |
| 4 | 1278 | 20791 | 14368 | 20097 | 25631 |
| 5 | 3288 | 26242 | 13229 | 9315 | 23742 |
| 6 | 61 | 2536 | 2301 | 1442 | 4504 |
| 7 | 37 | 395 | 484 | 972 | 2149 |
| 8 | 25 | 25 | 25 | 25 | 25 |
| 9 | 25 | 183 | 744 | 952 | 1823 |
| 10 | 25 | 89 | 311 | 513 | 817 |
| 11 | 29 | 708 | 2618 | 2165 | 3666 |
| 12 | 198 | 1458 | 1079 | 612 | 797 |
| 13 | 38 | 433 | 566 | 1080 | 626 |
| 14 | 104 | 541 | 3247 | 1609 | 838 |
| 15 | 212 | 2630 | 2472 | 1224 | 1496 |
| 16 | 183 | 2616 | 6680 | 2085 | 1631 |
| 17 | 28 | 201 | 375 | 222 | 1540 |
| 18 | 31699 | 15544 | 23095 | 6412 | 9059 |
| 19 | 63 | 243 | 554 | 299 | 441 |

The table shows that the highest titers were obtained for groups 4, 5 and 18, in which the adjuvants were 125 μg MPL, 50 μg MPL and QS21 plus MPL.

Example IX

Therapeutic Efficacy of Different Adjuvants

A therapeutic efficacy study was conducted in PDAPP transgenic mice with a set of adjuvants suitable for use in humans to determine their ability to potentiate immune responses to Aβ and to induce the immune-mediated clearance of amyloid deposits in the brain.

One hundred eighty male and female, 7.5- to 8.5-month old heterozygous PDAPP transgenic mice were obtained from Charles River Laboratories. The mice were sorted into nine groups containing 15 to 23 animals per group to be immunized with AN1792 or AN1528 combined with various adjuvants. Animals were distributed to match the gender, age, and parentage of the animals within the groups as closely as possible. The adjuvants included alum, MPL, and QS21, each combined with both antigens, and Freund's adjuvant (FA) combined with only AN1792. An additional group was immunized with AN1792 formulated in PBS buffer plus the preservative thimerosal without adjuvant. A ninth group was immunized with PBS alone as a negative control.

Preparation of aggregated Aβ peptides: human Aβ1-40 (AN1528; California Peptides Inc., Napa, Calif.; Lot ME0541) and human Aβ1-42 (AN1792; California Peptides Inc., Lot ME0439) peptides were freshly solubilized for the preparation of each set of injections from lyophilized powders that had been stored desiccated at −20° C. For this purpose, two mg of peptide were added to 0.9 ml of deionized water and the mixture was vortexed to generate a relatively uniform solution or suspension. AN1528 was soluble at this step, in contrast to AN1792. A 100 μl aliquot of 10× PBS (1× PBS: 0.15 M NaCl, 0.01 M sodium phosphate, pH 7.5) was then added at which point AN1528 began to precipitate. The suspensions were vortexed again and incubated overnight at 37° C. for use the next day.

To prepare vaccine doses with alum (Groups 1 and 5). Aβ peptide in PBS was added to Alhydrogel (two percent aqueous aluminum hydroxide gel, Sargeant, Inc., Clifton, N.J.) to reach concentrations of 100 μg Aβ peptide per 2 mg of alum. 10× PBS was added to a final dose volume of 200 μl in 1× PBS. The suspension was then gently mixed for approximately 4 hr at RT prior to injection.

To prepare vaccine doses for with MPL (Groups 2 and 6), lyophilized powder (Ribi ImmunoChem Research, Inc., Hamilton, Mont.; Lot 67039-E0896B) was added to 0.2% aqueous triethylamine to a final concentration of 1 mg/ml and vortexed. The mixture was heated to 65 to 70° C. for 30 sec to create a slightly opaque uniform suspension of micelles. The solution was stored at 4° C. For each set of injections, 100 μg of peptide per dose in 50 μl PBS, 50 μg of MPL per dose (50 μl) and 100 μl of PBS per dose were mixed in a borosilicate tube immediately before use.

To prepare vaccine doses with QS21 (Groups 3 and 7), lyophilized powder (Aquila, Framingham, Mass.; Lot A7018R) was added to PBS, pH 6.6–6.7 to a final concentration of 1 mg/ml and vortexed. The solution was stored at −20° C. For each set of injections, 100 μg of peptide per dose in 50 μl PBS, 25 μg of QS21 per dose in 25 μl PBS and 125 μl of PBS per dose were mixed in a borosilicate tube immediately before use.

To prepare vaccine doses with Freund's Adjuvant (Group 4), 100 μg of AN1792 in 200 μl PBS was emulsified 1:1 (vol:vol) with Complete Freund's Adjuvant (CFA) in a final volume of 400 μl for the first immunization. For subsequent immunizations, the antigen was similarly emulsified with Incomplete Freund's Adjuvant (IFA). For the formulations containing the adjuvants alum, MPL or QS21, 100 µg per dose of AN1792 or AN1528 was combined with alum (2 mg per dose) or MPL (50 µg per dose) or QS21 (25 µg per dose) in a final volume of 200 µl PBS and delivered by subcutaneous inoculation on the back between the shoulder blades. For the group receiving FA, 100 g of AN1792 was emulsified 1:1 (vol:vol) with Complete Freund's adjuvant (CFA) in a final volume of 400 µl and delivered intraperitoneally for the first immunization, followed by a boost of the same amount of immunogen in Incomplete Freund's adjuvant (IFA) for the subsequent five doses. For the group receiving AN1792 without adjuvant, 10 µg AN1792 was combined with 5 µg thimerosal in a final volume of 50 µl PBS and delivered subcutaneously. The ninth, control group received only 200 µl PBS delivered subcutaneously. Immunizations were given on a biweekly schedule for the first three doses, then on a monthly schedule thereafter on days 0, 16, 28, 56, 85 and 112. Animals were bled six to seven days following each immunization starting after the second dose for the measurement of antibody titers. Animals were euthanized approximately one week after the final dose. Outcomes were measured by ELISA assay of Aβ and APP levels in brain and by immunohistochemical evaluation of the presence of amyloid plaques in brain sections. In addition, Aβ-specific antibody titers, and Aβ-dependent proliferative and cytokine responses were determined.

Table 9 shows that the highest antibody titers to Aβ1-42 were elicited with FA and AN1792, titers which peaked following the fourth immunization (peak GMT: 75,386) and then declined by 59% after the final, sixth immunization. The peak mean titer elicited by MPL with AN1792 was 62% lower than that generated with FA (peak GMT: 28,867) and was also reached early in the immunization scheme, after 3 doses, followed by a decline to 28% of the peak value after the sixth immunization. The peak mean titer generated with QS21 combined with AN1792 (GMT: 1,511) was about 5-fold lower than that obtained with MPL. In addition, the kinetics of the response were slower, since an additional immunization was required to reach the peak response. Titers generated by alum-bound AN1792 were marginally greater than those obtained with QS21 and the response kinetics were more rapid. For AN1792 delivered in PBS with thimerosal the frequency and size of titers were barely greater than that for PBS alone. The peak titers generated with MPL and AN1528 (peak GMT 3099) were about 9-fold lower than those with AN1792. Alum-bound AN1528 was very poorly immunogenic with low titers generated in only some of the animals. No antibody responses were observed in the control animals immunized with PBS alone.

TABLE 9

| Treatment | Geometric Mean Antibody Titers[a] Week of Bleed | | | | |
|---|---|---|---|---|---|
| | 3.3 | 5.0 | 9.0 | 13.0 | 17.0 |
| Alum/ AN1792 | 102 (12/21)[b] | 1,081 (17/20) | 2,366 (21/21) | 1,083 (19/21) | 572 (18/21) |
| MPL/ AN1792 | 6241 (21/21) | 28,867 (21/21) | 1,1242 (21/21) | 5,665 (20/20) | 8,204 (20/20) |
| QS21/ AN1792 | 30 (1/20) | 227 (10/19) | 327 (10/19) | 1,511 (17/18) | 1,188 (14/18) |
| CFA/ AN1792 | 10,076 (15/15) | 61,279 (15/15) | 75,386 (15/15) | 41,628 (15/15) | 30,574 (15/15) |
| Alum/ AN1528 | 25 (0/21) | 33 (1/21) | 39 (3/20) | 37 (1/20) | 31 (2/20) |
| MPL/ AN1528 | 184 (15/21) | 2,591 (20/21) | 1,653 (21/21) | 1,156 (20/20) | 3,099 (20/20) |
| QS21/ AN1528 | 29 (1/22) | 221 (13/22) | 51 (4/22) | 820 (20/22) | 2,994 (21/22) |
| PBS plus Thimer | 25 (0/16) | 33 (2/16) | 39 (4/16) | 37 (3/16) | 47 (4/16) |
| PBS | 25 (0/16) | 25 (0/16) | 25 (0/15) | 25 (0/12) | 25 (0/16) |

Footnotes:
[a]Geometric mean antibody titers measured against Aβ1-42
[b]Number of responders per group The results of AN1792 or AN1592 treatment with various adjuvants, or thimerosal on cortical amyloid burden in 12-month old mice determined by ELISA are shown in FIGS. 15A–15E. In PBS control PDAPP mice the median level of total Aβ in the cortex at 12 months was 1,817 ng/g (FIG. 15A). Notably reduced levels of Aβ were observed in mice treated with AN1792 plus CFA/IFA (FIG. 15C), AN1792 plus alum (FIG. 15D), AN1792 plus MPL (FIG. 15E) and QS21 plus AN1792 (FIG. 15E). The reduction reached statistical significance (p<0.05) only for AN1792 plus CFA/IFA (FIG. 15C). However, as shown in Examples I and III, the effects of immunization in reducing Aβ levels become substantially greater in 15 month and 18 month old mice. Thus, it is expected that at least the AN1792 plus alum, AN1792 plus MPL and AN1792 plus QS21 compositions will achieve statistical significance in treatment of older mice. By contrast, the AN1792 plus the preservative thimerosal (FIG. 15D) showed a median level of Aβ about the same as that in the PBS treated mice. Similar results were obtained when cortical levels of Aβ42 were compared. The median level of A42 in PBS controls was 1624 ng/g. Notably reduced median levels of 403, 1149, 620 and 714 were observed in the mice treated with AN1792 plus CFA/IFA, AN1792 plus alum, AN1792 plus MPL and AN1792 plus QS21 respectively, with the reduction achieving statistical significance (p=0.05) for the AN1792 CFA/IFAβ treatment group. The median level in the AN1792 thimerosal treated mice was 1619 ng/g Aβ.

Example X

Toxicity Analysis

Tissues were collected for histopathologic examination at the termination of studies described in Examples 2, 3 and 7.

In addition, hematology and clinical chemistry were performed on terminal blood samples from Examples 3 and 7. Most of the major organs were evaluated, including brain, pulmonary, lymphoid, gastrointestinal, liver, kidney, adrenal and gonads. Although sporadic lesions were observed in the study animals, there were no obvious differences, either in tissues affected or lesion severity, between AN1792 treated and untreated animals. There were no unique histopathological lesions noted in AN-1782-immunized animals compared to PBS-treated or untreated animals. There were also no differences in the clinical chemistry profile between adjuvant groups and the PBS treated animals in Example 7. Although there were significant increases in several of the hematology parameters between animals treated with AN1792 and Freund's adjuvant in Example 7 relative to PBS treated animals, these type of effects are expected from Freund's adjuvant treatment and the accompanying peritonitis and do not indicate any adverse effects from AN1792 treatment. Although not part of the toxicological evaluation, PDAPP mouse brain pathology was extensively examined as part of the efficacy endpoints. No sign of treatment related adverse effect on brain morphology was noted in any of the studies. These results indicate that AN1792 treatment is well tolerated and at least substantially free of side effects.

Example XI

Prevention and Treatment of Subjects

A single-dose phase I trial is performed to determine safety. A therapeutic agent is administered in increasing dosages to different patients starting from about 0.01 the level of presumed efficacy, and increasing by a factor of three until a level of about 10 times the effective mouse dosage is reached.

A phase II trial is performed to determine therapeutic efficacy. Patients with early to mid Alzheimer's Disease defined using Alzheimer's disease and Related Disorders Association (ADRDA) criteria for probable AD are selected. Suitable patients score in the 12–26 range on the Mini-Mental State Exam (MMSE). Other selection criteria are that patients are likely to survive the duration of the study and lack complicating issues such as use of concomitant medications that may interfere. Baseline evaluations of patient function are made using classic psychometric measures, such as the MMSE, and the ADAS, which is a comprehensive scale for evaluating patients with Alzheimer's Disease status and function. These psychometric scales provide a measure of progression of the Alzheimer's condition. Suitable qualitative life scales can also be used to monitor treatment. Disease progression can also be monitored by MRI. Blood profiles of patients can also be monitored including assays of immunogen-specific antibodies and T-cells responses.

Following baseline measures, patients begin receiving treatment. They are randomized and treated with either therapeutic agent or placebo in a blinded fashion. Patients are monitored at least every six months. Efficacy is determined by a significant reduction in progression of a treatment group relative to a placebo group.

A second phase II trial is performed to evaluate conversion of patients from non-Alzheimer's Disease early memory loss, sometimes referred to as age-associated memory impairment (AAMI), to probable Alzheimer's disease as defined as by ADRDA criteria. Patients with high risk for conversion to Alzheimer's Disease are selected from a non-clinical population by screening reference populations for early signs of memory loss or other difficulties associated with pre-Alzheimer's symptomatology, a family history of Alzheimer's Disease, genetic risk factors, age, sex, and other features found to predict high-risk for Alzheimer's Disease. Baseline scores on suitable metrics including the MMSE and the ADAS together with other metrics designed to evaluate a more normal population are collected. These patient populations are divided into suitable groups with placebo comparison against dosing alternatives with the agent. These patient populations are followed at intervals of about six months, and the endpoint for each patient is whether or not he or she converts to probable Alzheimer's Disease as defined by ADRDA criteria at the end of the observation.

Example XII

General Materials and Methods

1. Measurement of Antibody Titers

Mice were bled by making a small nick in the tail vein and collecting about 200 $\mu$l of blood into a microfuge tube. Guinea pigs were bled by first shaving the back hock area and then using an 18 gauge needle to nick the metatarsal vein and collecting the blood into microfuge tubes. Blood was allowed to clot for one hr at room temperature (RT), vortexed, then centrifuged at 14,000×g for 10 min to separate the clot from the serum. Serum was then transferred to a clean microfuge tube and stored at 4° C. until titered.

Antibody titers were measured by ELISA. 96-well microtiter plates (Costar EIA plates) were coated with 100 $\mu$l of a solution containing either 100 $\mu$g/ml either A$\beta$42 or SAPP or other antigens as noted in each of the individual reports in Well Coating Buffer (0.1 M sodium phosphate, pH 8.5, 0.1% sodium azide) and held overnight at RT. The wells were aspirated and sera were added to the wells starting at a 1/100 dilution in Specimen Diluent (0.014 M sodium phosphate, pH 7.4, 0.15 M NaCl, 0.6% bovine serum albumin, 0.05% thimerosal). Seven serial dilutions of the samples were made directly in the plates in three-fold steps to reach a final dilution of 1/218,700. The dilutions were incubated in the coated-plate wells for one hr at RT. The plates were then washed four times with PBS containing 0.05% Tween 20. The second antibody, a goat anti-mouse Ig conjugated to horseradish peroxidase (obtained from Boehringer Mannheim), was added to the wells as 100 $\mu$l of a 1/3000 dilution in Specimen Diluent and incubated for one hr at RT. Plates were again washed four times in PBS, Tween 20. To develop the chromogen, 100 $\mu$l of Slow TMB (3,3',5,5'-tetramethyl benzidine obtained from Pierce Chemicals) was added to each well and incubated for 15 min at RT. The reaction was stopped by the addition of 25 $\mu$l of 2 M $H_2SO_4$. The color intensity was then read on a Molecular Devices Vmax at (450 nm–650 nm).

Titers were defined as the reciprocal of the dilution of serum giving one half the maximum OD. Maximal OD was generally taken from an initial 1/100 dilution, except in cases with very high titers, in which case a higher initial dilution was necessary to establish the maximal OD. If the 50% point fell between two dilutions, a linear extrapolation was made to calculate the final titer. To calculate geometric mean antibody titers, titers less than 100 were arbitrarily assigned a titer value of 25.

2. Lymphocyte Proliferation Assay

Mice were anesthetized with isoflurane. Spleens were removed and rinsed twice with 5 ml PBS containing 10% heat-inactivated fetal bovine serum (PBS-FBS) and then homogenized in a 50 $\mu$l Centricon unit (Dako A/S, Denmark)

in 1.5 ml PBS-FBS for 10 sec at 100 rpm in a Medimachine (Dako) followed by filtration through a 100μ pore size nylon mesh. Splenocytes were washed once with 15 ml PBS-FBS, then pelleted by centrifugation at 200×g for 5 min. Red blood cells were lysed by resuspending the pellet in 5 mL buffer containing 0.15 M NH$_4$Cl, 1 M KHCO$_3$, 0.1 M NaEDTA, pH 7.4 for five min at RT. Leukocytes were then washed as above. Freshly isolated spleen cells (1 cells per well) were cultured in triplicate sets in 96-well U-bottomed tissue culture-treated microtiter plates (Corning, Cambridge, Mass.) in RPMI 1640 medium (JRH Biosciences, Lenexa, Kans.) supplemented with 2.05 mM L glutamine, 1% Penicillin/Streptomycin, and 10% heat-inactivated FBS, for 96 hr at 37° C. Various Aβ peptides, Aβ1-16, Aβ1-40, Aβ1-42 or Aβ40-1 reverse sequence protein were also added at doses ranging from 5 μM to 0.18 μM in four steps. Cells in control wells were cultured with Concanavalin A (Con A) (Sigma, cat. # C-5275, at 1 μg/ml) without added protein. Cells were pulsed for the final 24 hr with $^3$H-thymidine (1 μCi/well obtained from Amersham Corp., Arlington Heights Ill.). Cells were then harvested onto UniFilter plates and counted in a Top Count Microplate Scintillation Counter (Packard Instruments, Downers Grove, Ill.). Results are expressed as counts per minute (cpm) of radioactivity incorporated into insoluble macromolecules.

3. Brain Tissue Preparation

After euthanasia, the brains were removed and one hemisphere was prepared for immunohistochemical analysis, while three brain regions (hippocampus, cortex and cerebellum) were dissected from the other hemisphere and used to measure the concentration of various Aβ proteins and APP forms using specific ELISAs (Johnson-Wood et al., supra).

Tissues destined for ELISAs were homogenized in 10 volumes of ice-cold guanidine buffer (5.0 M guanidine-HCl, 50 mM Tris-HCl, pH 8.0). The homogenates were mixed by gentle agitation using an Adams Nutator (Fisher) for three to four hr at RT, then stored at –20° C. prior to quantitation of Aβ and APP. Previous experiments had shown that the analytes were stable under this storage condition, and that synthetic Aβ protein (Bachem) could be quantitatively recovered when spiked into homogenates of control brain tissue from mouse littermates (Johnson-Wood et al., supra).

4. Measurement of Aβ Levels

The brain homogenates were diluted 1:10 with ice cold Casein Diluent (0.25% casein, PBS, 0.05% sodium azide, 20 μg/ml aprotinin, 5 mM EDTA pH 8.0, 10 μg/ml leupeptin) and then centrifuged at 16,000×g for 20 min at 4 C. The synthetic Aβ protein standards (1–42 amino acids) and the APP standards were prepared to include 0.5 M guanidine and 0.1% bovine serum albumin (BSA) in the final composition. The "total" Aβ sandwich ELISA utilizes monoclonal antibody (mAb) 266, specific for amino acids 13–28 of Aβ (Seubert, et al.), as the capture antibody, and biotinylated mAb 3D6, specific for amino acids 1–5 of Aβ (Johnson-Wood, et al), as the reporter antibody. The 3D6 mAb does not recognize secreted APP or full-length APP, but detects only Aβ species with an amino-terminal aspartic acid. The cell line designated RB96 3D6.32.2.4 producing the antibody 3D6 has the ATCC accession number PTA-5130, having been deposited on Apr. 8, 2003. This assay has a lower limit of sensitivity of ~50 ng/ml (11 nM) and shows no cross-reactivity to the endogenous murine Aβ protein at concentrations up to 1 ng/ml (Johnson-Wood et al., supra).

The Aβ1-42 specific sandwich ELISA employs mAP 21F12, specific for amino acids 33–42 of Aβ (Johnson-Wood, et al.), as the capture antibody. Biotinylated mAβ 3D6 is also the reporter antibody in this assay which has a lower limit of sensitivity of about 125 μg/ml (28 pM, Johnson-Wood et al.). For the Aβ ELISAs, 100 μl of either mAβ 266 (at 10 μg/ml) or mAβ 21F12 at (5 μg/ml) was coated into the wells of 96-well immunoassay plates (Costar) by overnight incubation at RT. The solution was removed by aspiration and the wells were blocked by the addition of 200 μl of 0.25% human serum albumin in PBS buffer for at least 1 hr at RT. Blocking solution was removed and the plates were stored desiccated at 4° C. until used. The plates were rehydrated with Wash Buffer [Tris-buffered saline (0.15 M NaCl, 0.01 M Tris-HCl, pH 7.5), plus 0.05% Tween 20] prior to use. The samples and standards were added in triplicate aliquots of 100 μl per well and then incubated overnight at 4° C. The plates were washed at least three times with Wash Buffer between each step of the assay. The biotinylatea mAβ 3D6, diluted to 0.5 μg/ml in Casein Assay Buffer (0.25% casein, PBS, 0.05% Tween 20, pH 7.4), was added and incubated in the wells for 1 hr at RT. An avidin-horseradish peroxidase conjugate, (Avidin-HRP obtained from Vector, Burlingame, Calif.), diluted 1:4000 in Casein Assay Buffer, was added to the wells for 1 hr at RT. The calorimetric substrate, Slow TMB-ELISA (Pierce), was added and allowed to react for 15 minutes at RT, after which the enzymatic reaction was stopped by the addition of 25 μl 2 N H$_2$SO$_4$. The reaction product was quantified using a Molecular Devices Vmax measuring the difference in absorbance at 450 nm and 650 nm.

5. Measurement of APP Levels

Two different APP assays were utilized. The first, designated APP-α/FL, recognizes both APP-alpha (a) and full-length (FL) forms of APP. The second assay is specific for APP-α. The APP-α/FL assay recognizes secreted APP including the first 12 amino acids of Aβ. Since the reporter antibody (2H3) is not specific to the α-clip-site, occurring between amino acids 612–613 of APP695 (Esch et al., Science 248, 1122–1124 (1990)); this assay also recognizes full length APP (APP-FL). Preliminary experiments using immobilized APP antibodies to the cytoplasmic tail of APP-FL to deplete brain homogenates of APP-FL suggest that approximately 30–40% of the APP-α/FL APP is FL (data not shown). The capture antibody for both the APP-α/FL and APP-α assays is mAβ 8E5, raised against amino acids 444 to 592 of the APP695 form (Games et al., supra). The reporter mAβ for the APP-α/FL assay is mAβ 2H3, specific for amino acids 597–608 of APP695 (Johnson-Wood et al., supra) and the reporter antibody for the APP-α assay is a biotinylated derivative of mAβ 16H9, raised to amino acids 605 to 611 of APP. The lower limit of sensitivity of the APP-α/FL assay is about 11 ng/ml (150 pM) (Johnson-Wood et al.) and that of the APP-α specific assay is 22 ng/ml (0.3 nM). For both APP assays, mAβ 8E5 was coated onto the wells of 96-well EIA plates as described above for mAβ 266. Purified, recombinant secreted APP-α was used as the reference standard for the APP-α assay and the APP-α/FL assay (Esch et al., supra). The brain homogenate samples in 5 M guanidine were diluted 1:10 in ELISA Specimen Diluent (0.014 M phosphate buffer, pH 7.4, 0.6% bovine serum albumin, 0.05% thimerosal, 0.5 M NaCl, 0.1% NP40). They were then diluted 1:4 in Specimen Diluent containing 0.5 M guanidine. Diluted homogenates were then centrifuged at 16,000×g for 15 seconds at RT. The APP standards and samples were added to the plate in duplicate aliquots and incubated for 1.5 hr at RT. The biotinylated reporter antibody 2H3 or 16H9 was incubated with samples for 1 hr at RT. Streptavidin-alkaline phosphatase (Boehringer Mannheim), diluted 1:1000 in specimen diluent, was incubated in the wells for 1 hr at RT. The fluorescent substrate 4-methyl-umbellipheryl-phosphate was added for a 30-min RT incubation and the plates were read on a Cytofluor tm 2350 fluorimeter (Millipore) at 365 nm excitation and 450 nm emission.

6. Immunohistochemistry

Brains were fixed for three days at 4° C. in 4% paraformaldehyde in PBS and then stored from one to seven days at 4° C. in 1% paraformaldehyde, PBS until sectioned. Forty-micron-thick coronal sections were cut on a vibratome at RT and stored in cryoprotectant (30% glycerol, 30% ethylene glycol in phosphate buffer) at −20° C. prior to immunohistochemical processing. For each brain, six sections at the level of the dorsal hippocampus, each separated by consecutive 240 µm intervals, were incubated overnight with one of the following antibodies: (1) a biotinylated anti-Aβ (mAβ, 3D6, specific for human Aβ) diluted to a concentration of 2 µg/ml in PBS and 1% horse serum; or (2) a biotinylated mAβ specific for human APP, 8E5, diluted to a concentration of 3 µg/ml in PBS and 1.0% horse serum; or (3) a mAβ specific for glial fibrillary acidic protein (GFAP; Sigma Chemical Co.) diluted 1:500 with 0.25% Triton X-100 and 1% horse serum, in Tris-buffered saline, pH 7.4 (TBS); or (4) a mAβ specific for CD11b, MAC-1 antigen, (Chemicon International) diluted 1:100 with 0.25% Triton X-100 and 1% rabbit serum in TBS; or (5) a mAβ specific for MHC II antigen, (Pharmingen) diluted 1:100 with 0.25% Triton X-100 and 1% rabbit serum in TBS; or (6) a rat mAβ specific for CD 43 (Pharmingen) diluted 1:100 with 1% rabbit serum in PBS or (7) a rat mAβ specific for CD 45RA (Pharmingen) diluted 1:100 with 1% rabbit serum in PBS; or (8) a rat monoclonal Aβ specific for CD 45RB (Pharmingen) diluted 1:100 with 1% rabbit serum in PBS; or (9) a rat monoclonal Aβ specific for CD 45 (Pharmingen) diluted 1:100 with 1% rabbit serum in PBS; or (10) a biotinylated polyclonal hamster Aβ specific for CD3e (Pharmingen) diluted 1:100 with 1% rabbit serum in PBS or (11) a rat mAβ specific for CD3 (Serotec) diluted 1:200 with 1% rabbit serum in PBS; or with (12) a solution of PBS lacking a primary antibody containing 1% normal horse serum.

Sections reacted with antibody solutions listed in 1,2 and 6–12 above were pretreated with 1.0% Triton X-100, 0.4% hydrogen peroxide in PBS for 20 min at RT to block endogenous peroxidase. They were next incubated overnight at 4° C. with primary antibody. Sections reacted with 3D6 or 8E5 or CD3e mAβs were then reacted for one hr at RT with a horseradish peroxidase-avidin-biotin-complex with kit components "A" and "B" diluted 1:75 in PBS (Vector Elite Standard Kit, Vector Labs, Burlingame, Calif.). Sections reacted with antibodies specific for CD 45RA, CD 45RB, CD 45, CD3 and the PBS solution devoid of primary antibody were incubated for 1 hour at RT with biotinylated anti-rat IgG (Vector) diluted 1:75 in PBS or biotinylated anti-mouse IgG (Vector) diluted 1:75 in PBS, respectively. Sections were then reacted for one hr at RT with a horseradish peroxidase-avidin-biotin-complex with kit components "A" and "B" diluted 1:75 in PBS (Vector Elite Standard Kit, Vector Labs, Burlingame, Calif.).

Sections were developed in 0.01% hydrogen peroxide, 0.05% 3,3'-diaminobenzidine (DAB) at RT. Sections destined for incubation with the GFAP-, MAC-1- AND MHC II-specific antibodies were pretreated with 0.6% hydrogen peroxide at RT to block endogenous peroxidase then incubated overnight with the primary antibody at 4° C. Sections reacted with the GFAP antibody were incubated for 1 hr at RT with biotinylated anti-mouse IgG made in horse (Vector Laboratories; Vectastain Elite ABC Kit) diluted 1:200 with TBS. The sections were next reacted for one hr with an avidin-biotin-peroxidase complex (Vector Laboratories; Vectastain Elite ABC Kit) diluted 1:1000 with TBS. Sections incubated with the MAC-1-or MHC II-specific mAβ as the primary antibody were subsequently reacted for 1 hr at RT with biotinylated anti-rat IgG made in rabbit diluted 1:200 with TBS, followed by incubation for one hr with avidin-biotin-peroxidase complex diluted 1:1000 with TBS. Sections incubated with GFAP-, MAC-1- and MHC II-specific antibodies were then visualized by treatment at RT with 0.05% DAB, 0.01% hydrogen peroxide, 0.04% nickel chloride, TBS for 4 and 11 min, respectively.

Immunolabeled sections were mounted on glass slides (VWR, Superfrost slides), air dried overnight, dipped in Propar (Anatech) and overlaid with coverslips using Permount (Fisher) as the mounting medium.

To counterstain Aβ plaques, a subset of the GFAP-positive sections were mounted on Superfrost slides and incubated in aqueous 1% Thioflavin S (Sigma) for 7 min following immunohistochemical processing. Sections were then dehydrated and cleared in Propar, then overlaid with coverslips mounted with Permount.

7. Image Analysis

A Videometric 150 Image Analysis System (Oncor, Inc., Gaithersburg, Md.) linked to a Nikon Microphot-FX microscope through a CCD video camera and a Sony Trinitron monitor was used for quantification of the immunoreactive slides. The image of the section was stored in a video buffer and a color- and saturation-based threshold was determined to select and calculate the total pixel area occupied by the immunolabeled structures. For each section, the hippocampus was manually outlined and the total pixel area occupied by the hippocampus was calculated. The percent amyloid burden was measured as: (the fraction of the hippocampal area containing Aβ deposits immunoreactive with mAβ 3D6)×100. Similarly, the percent neuritic burden was measured as: (the fraction of the hippocampal area containing dystrophic neurites reactive with mAβ 8E5)×100. The C-Imaging System (Compix, Inc., Cranberry Township, Pa.) operating the Simple 32 Software Application program was linked to a Nikon Microphot-FX microscope through an Optronics camera and used to quantitate the percentage of the retrospenial cortex occupied by GFAP-positive astrocytes and MAC-1- and MHC II-positive microglia. The image of the immunoreacted section was stored in a video buffer and a monochrome-based threshold was determined to select and calculate the total pixel area occupied by immunolabeled cells. For each section, the retrosplenial cortex (RSC) was manually outlined and the total pixel area occupied by the RSC was calculated. The percent astrocytosis was defined as: (the fraction of RSC occupied by GFAP-reactive astrocytes)×100. Similarly, percent microgliosis was defined as: (the fraction of the RSC occupied by MAC-1- or MHC 1'-reactive microglia)×100. For all image analyses, six sections at the level of the dorsal hippocampus, each separated by consecutive 240 µm intervals, were quantitated for each animal. In all cases, the treatment status of the animals was unknown to the observer.

Although the foregoing invention has been described in detail for purposes of clarity of understanding, it will be obvious that certain modifications may be practiced within the scope of the appended claims. All publications and patent documents cited herein are hereby incorporated by reference in their entirety for all purposes to the same extent as if each were so individually denoted.

What is claimed is:

1. A therapeutic agent comprising a peptide analog of an immunogenic, natural Aβ peptide or a fragment thereof, the analog comprising an epitope that induces a similar protective or therapeutic immune response on administration to a patient as the Aβ peptide.

2. The therapeutic agent of claim 1, wherein the analog exhibits at least 90% sequence identity with the immunogenic Aβ fragment.

3. The therapeutic agent of claim 1, which is the analog of an Aβ fragment comprising at least 20 contiguous amino acids of the Aβ peptide.

4. The therapeutic agent of claim 1, which is the analog of an Aβ fragment comprising the N-terminal half of the Aβ peptide.

5. The therapeutic agent of claim 1, which is the analog of an Aβ fragment consisting of the first 20 N-terminal amino acids of SEQ ID NO:1.

6. The therapeutic agent of claim 1, comprising a multimer of the analog.

7. The therapeutic agent of claim 1, wherein the analog comprises a carrier molecule linked at its amino terminus, its carboxyl terminus or internally to form a conjugate.

8. The therapeutic agent of claim 1, wherein the analog comprises a carrier molecule linked at its amino terminus or at its carboxyl terminus.

9. The therapeutic agent of claim 7, wherein the carrier molecule is a peptide.

10. The therapeutic agent of claim 9, wherein the peptide comprises polymeric amino acids.

11. The therapeutic agent of claim 10, wherein the peptide comprises polylysine or polyglutamic acid.

12. The therapeutic agent of claim 7, comprising a multimer of the analog linked to the carrier molecule.

13. The therapeutic agent of claim 12, wherein the carrier molecule is a peptide.

14. The therapeutic agent of claim 13, wherein the peptide comprises polymeric amino acids.

15. The therapeutic agent of claim 14, wherein the peptide comprises polylysine or polyglutamic acid.

16. A pharmaceutical composition comprising the therapeutic agent of any one of claims 1, 6, 7, or 12 and a pharmaceutically acceptable component.

17. The pharmaceutical composition of claim 16, wherein the pharmaceutically acceptable component is an adjuvant, a diluent, a stabilizer, a carrier, an auxiliary substance or an excipient.

18. The pharmaceutical composition of claim 17, wherein the adjuvant is alum.

19. The therapeutic agent of one of claims 1 or 6, wherein the analog is cross-linked to a carrier molecule to form a conjugate.

20. The therapeutic agent of claim 19, wherein the carrier molecule is a protein, peptide, or toxin.

21. The therapeutic agent of claim 20, wherein the peptide comprises polymeric amino acids.

22. The therapeutic agent of claim 21, wherein the peptide comprises polylysine or polyglutamic acid.

23. The therapeutic agent of claim 20, wherein the carrier molecule comprises a helper T cell epitope.

24. The therapeutic agent of claim 23, wherein the helper T cell epitope comprises a universal T-cell epitope.

25. The therapeutic agent of claim 24, wherein the carrier molecule comprising the helper T cell epitope is tetanus toxoid, diphtheria toxoid or hepatitis B virus surface antigen (HBsAg).

26. The therapeutic agent of claim 24, wherein the universal T-cell epitope comprises a universal T-cell epitope of tetanus toxoid, hepatitis B virus surface antigen, influenza hemagluttinin, or bacille Calmette-Guerin.

27. The therapeutic agent of claim 19, wherein the carrier molecule is a polyactide polyglycolide coploymer (PLPG).

28. A pharmaceutical composition comprising the therapeutic agent of claim 19 and a pharmaceutically acceptable component.

29. The pharmaceutical composition of claim 28, wherein the pharmaceutically acceptable component is an adjuvant, a diluent, a stabilizer, a carrier, an auxiliary substance or an excipient.

30. The pharmaceutical composition of claim 29, wherein the adjuvant is alum.

31. The therapeutic agent of one of claims 7 to 15, wherein the conjugate is cross-linked to a carrier molecule.

32. The therapeutic agent of claim 31, wherein the carrier molecule is a protein, peptide, or toxin.

33. The therapeutic agent of claim 31, wherein the peptide comprises polymeric amino acids.

34. The therapeutic agent of claim 33, wherein the peptide comprises polylysine or polyglutamic acid.

35. The therapeutic agent of claim 32, wherein the carrier molecule comprises a helper T cell epitope.

36. The therapeutic agent of claim 35, wherein the helper T cell epitope comprises a universal T-cell epitope.

37. The therapeutic agent of claim 35, wherein the carrier molecule comprising the helper T cell is tetanus toxoid, diphtheria toxoid or hepatitis B virus surface antigen (HBsAg).

38. The therapeutic agent of claim 36, wherein the universal T-cell epitope comprises a universal T-cell epitope of tetanus toxoid, hepatitis B virus surface antigen, influenza hemagluttinin, or bacille Calmette-Guerin.

39. The therapeutic agent of claim 31, wherein the carrier molecule is a polyactide polyglycoloide copolymer (PLPG).

40. A Pharmaceutical composition comprising the therapeutic agent of claim 31 and a pharmaceutically acceptable component.

41. The pharmaceutical composition of claim 40, wherein the pharmaceutically acceptable component is an adjuvant, a diluent, a stabilizer, a carrier, an auxiliary substance or an excipient.

42. The pharmaceutical composition of claim 41, wherein the adjuvant is alum.

* * * * *